United States Patent [19]
Arnaiz et al.

[11] Patent Number: 5,849,759
[45] Date of Patent: Dec. 15, 1998

[54] NAPHTHYL-SUBSTITUTED BENZIMIDAZOLE DERIVATIVES AS ANTI-COAGULANTS

[75] Inventors: Damian O. Arnaiz, Hercules; Brian D. Griedel; Steven T. Sakata, both of Richmond; Kenneth J. Shaw, San Rafael; Zuchun Zhao, El Sobrante, all of Calif.

[73] Assignee: Berlex Laboratories, Inc., Richmond, Calif.

[21] Appl. No.: 570,057

[22] Filed: Dec. 8, 1995

[51] Int. Cl.$^6$ .................. A61K 31/445; C07D 211/52
[52] U.S. Cl. .................. 514/322; 514/394; 514/395; 546/199; 548/304.4; 548/306.1; 548/306.4; 548/307.1; 548/309.4; 548/309.7; 548/310.1
[58] Field of Search .................. 564/225, 229, 564/244; 546/199; 548/306.1, 306.4, 307.1, 304.4, 309.7, 309.4, 310.1; 514/322, 394, 395

[56] References Cited

U.S. PATENT DOCUMENTS

| | | | |
|---|---|---|---|
| 4,634,783 | 1/1987 | Fujii | 549/475 |
| 5,332,822 | 7/1994 | Misra | 546/164 |

FOREIGN PATENT DOCUMENTS

| | | |
|---|---|---|
| 0540051A1 | 10/1992 | European Pat. Off. . |
| 0567966A1 | 4/1993 | European Pat. Off. . |
| 0601459A2 | 12/1993 | European Pat. Off. . |
| 93/15756 | 8/1993 | WIPO . |
| 94/13693 | 6/1994 | WIPO . |
| 94/17817 | 8/1994 | WIPO . |

OTHER PUBLICATIONS

Kaiser B, Hauptmann J. Cardiovascular Drug Reviews, 12(3), 225–236, 1994.

Tidwell, R. et al., "Strategies for Anticoagulation with Synthetic Protease Inhibitors, Xa Inhibitors Versus Thrombin Inhibitors," *Thrombosis Research*, (1980) 19:339–349.

Wagner, G. et al., "Synthese von a–a'–Bis[amidinobenzyliden]–und a–a'Bis–[amidinobenzyl]–cycloalkanonen," *Pharmazie*, (1977) 32,141–145.

Stürzebecher, J. et al., "Cyclic Amides of Nα–arysulfonylaminoacylated 4–amidinophenylalanine—Tight Binding Inhibitors of Thrombin," *Thrombosis Research*, (1983) 29:635–642.

Kikumoto, R. et al., "Selective inhibition of Thrombin by (2R,4R)–4–Methyl–1–[N$^2$[(3–methyl–1,2,3, 4–tetrahydro–8–quinolinyl)–sulfonyl]–L–arginyl)]–2piperidinecarboxylic Acid," *Biochemistry*, (1984) 23:85–90.

Stürzebecher, J. et al., "Synthetic Inhibitors of Serine Proteinases XXIII, Inhibition of Factor Xa by Diamidines", *Thrombosis Research*, (1980) 17:545:548.

*Primary Examiner*—Evelyn Huang
*Attorney, Agent, or Firm*—Carol J. Roth

[57] ABSTRACT

Compounds of formula (I):

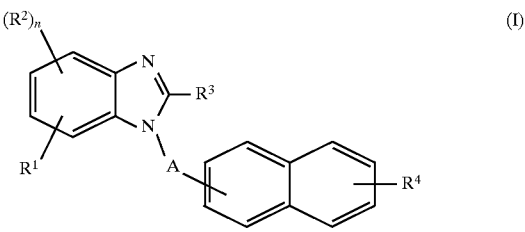

wherein:

n,
A,
$R^1$,
$R^2$,
$R^3$, and $R^4$ have meanings as defined herein, or a pharmaceutically acceptable salt thereof, are useful as anticoagulants.

14 Claims, No Drawings

NAPHTHYL-SUBSTITUTED BENZIMIDAZOLE DERIVATIVES AS ANTI-COAGULANTS

FIELD OF THE INVENTION

The present invention is directed to naphthyl-substituted benzimidazole derivatives and their pharmaceutically acceptable salts, which inhibit certain enzymes in the coagulation cascade, such as factor Xa and factor IIa (thrombin), thereby being useful as anti-coagulants. It also relates to pharmaceutical compositions containing the derivatives or their pharmaceutically acceptable salts, and their methods of use.

BACKGROUND OF THE INVENTION

Factor Xa is a member of the trypsin-like serine protease class of enzymes. A one-to-one binding of factors Xa and Va with calcium ions and phospholipid forms the prothrombinase complex which converts prothrombin to factor IIa (thrombin). Thrombin, in turn, converts fibrinogen to fibrin which polymerizes to form insoluble fibrin.

In the coagulation cascade, the prothrombinase complex is the convergent point of the intrinsic (surface activated) and extrinsic (vessel injury-tissue factor) pathways (*Biochemistry* (1991), Vol. 30, p. 10363; and *Cell* (1988), Vol. 53, pp. 505–518). The model of the coagulation cascade has been refined further with the discovery of the mode of action of tissue factor pathway inhibitor (TFPI) (*Seminars in Hematology* (1992), Vol. 29, pp. 159–161). TFPI is a circulating multi-domain serine protease inhibitor with two serpin domains which competes with factor Va for free factor Xa. Once formed, the binary complex of factor Xa and TFPI becomes a potent inhibitor of the factor VIIa and tissue factor complex.

Factor Xa can be activated by two distinct complexes, by tissue factor—factor VIIa complex on the "Xa burst" pathway and by the factor IXa-VIIIa complex (TENase) of the "sustained Xa" pathway in the coagulation cascade. After vessel injury, the "Xa burst" pathway is activated via tissue factor (TF). Up regulation of the coagulation cascade occurs via increased factor Xa production via the "sustained Xa" pathway. Down regulation of the coagulation cascade occurs with the formation of the factor Xa-TFPI complex, which not only removes factor Xa but also inhibits further factor formation via the "Xa burst" pathway. Consequently, there is a natural regulation of the coagulation cascade by factor Xa.

Published data with the proteins antistasin and tick anti-coagulant peptide (TAP) demonstrate that factor Xa inhibitors are efficacious anti-coagulants (*Thrombosis and Haemostasis* (1992), Vol. 67, pp. 371–376; and *Science* (1990), Vol. 248, pp. 593–596).

The active site of factor Xa can be blocked by either a mechanism-based or a tight binding inhibitor (a tight binding inhibitor differs from a mechanism-based inhibitor by the lack of a covalent link between the enzyme and the inhibitor). Two types of mechanism-based inhibitors are known, reversible and irreversible, which are distinguished by ease of hydrolysis of the enzyme-inhibitor link (*Thrombosis Res* (1992), Vol. 67, pp. 221–231; and *Trends Pharmacol. Sci.* (1987), Vol. 8, pp. 303–307). A series of guanidino compounds are examples of tight-binding inhibitors (*Thrombosis Res.* (1980), Vol. 19, pp. 339–349). Arylsulfonyl-arginine-piperidinecarboxylic acid derivatives have also been shown to be tight-binding inhibitors of thrombin (*Biochem.* (1984), Vol. 23, pp. 85–90), as well as a series of arylamidine-containing compounds, including 3-amidinophenylaryl derivatives (*Thrombosis Res.* (1983), Vol. 29, pp. 635–642) and bis(amidino)benzyl cycloketones (*Thrombosis Res.* (1980), Vol. 17, pp. 545–548). Therapeutic utility of these compounds, however, is limited by their poor selectivity for factor Xa.

Related Disclosures

European Published Patent Application 0 540 051 (Nagahara et al.) describes aromatic amidine derivatives which are stated to be capable of showing a strong anticoagulant effect through reversible inhibition of factor Xa.

The synthesis of α,α'-bis(amidinobenzylidene) cycloalkanones and α,α'-bis(amidino-benzyl) cycloalkanones is described in *Pharmazie* (1977), Vol. 32, No. 3, pp. 141–145. These compounds are disclosed as being serine protease inhibitors.

SUMMARY OF THE INVENTION

This invention is directed to compounds or their pharmaceutically acceptable salts which are anti-coagulants by inhibiting enzymes in the coagulation cascade, such as human factor Xa and factor IIa (thrombin), and are therefore useful as pharmacological agents for the treatment of disease-states characterized by thrombotic activity.

Accordingly, in one aspect, this invention provides compounds of formula (I):

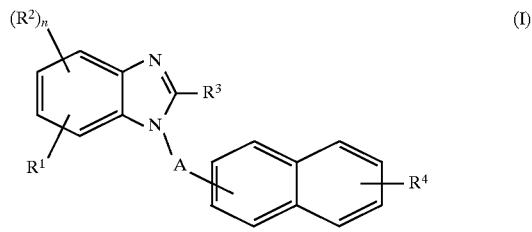

wherein:

n is 0 to 3;

A is a branched or straight chain alkylene, —C(O)— or —S(O)$_2$—;

R$^1$ is hydrogen, —OR$^5$ or —N(R$^5$)R$^6$;

each R$^2$ is independently nitro, alkyl (optionally substituted by halo, aryl, —C(O)OR$^8$, —C(O)N(R$^8$)R$^9$, —N(R$^8$)R$^9$), —OR$^5$, —N(R$^7$)R$^7$, —N(R$^7$)R$^9$, —N(R$^8$)R$^9$, —N(R$^8$)C(O)R$^7$, —C(O)OR$^8$, —C(O)N(R$^7$)R$^9$, —C(O)N(R$^8$)R$^9$, or a heterocyclyl optionally substituted by one or more substituents selected from the group consisting of —C(NH)N(R$^8$)R$^9$, —C(NH)N(H)OR$^8$, —C(NH)N(H)C(O)R$^8$, —C(NH)N(H)C(O)OR$^8$, —C(O)OR$^8$, —C(O)N(R$^8$)R$^9$, —R$^{10}$—C(O)OR$^8$, —R$^{10}$—C(O)N(R$^8$)R$^9$ and —SO$_3$H;

R$^3$ is hydrogen or alkyl optionally substituted by one or more substituents selected from the group consisting of halo, alkenyl, hydroxy, alkoxy, aryl (optionally substituted by alkyl, hydroxy, halo, —N(R$^8$)R$^9$, —C(O)OR$^8$, —C(O)N(R$^8$)R$^9$), aryloxy (optionally substituted by alkyl, hydroxy, halo, —N(R$^8$)R$^9$, —C(O)OR$^8$, —C(O)N(R$^8$)R$^9$), aralkoxy (optionally substituted by alkyl, hydroxy, halo, —N(R$^8$)R$^9$, —C(O)OR$^8$, —C(O)N(R$^8$)R$^9$), haloalkenyl, cycloalkyl, imidazolyl, indolyl, adamantyl (optionally substituted by halo, alkyl, —N(R$^8$)R$^9$, —C(O)OR$^8$ or —C(O)N(R$^8$)R$^9$), —C(O)OR$^8$, —N(R$^8$)R$^9$, —C(O)N(R$^8$)R$^9$, —C(O)(CH$_2$)$_m$OR$^8$ (where m is 1 to 4), —N(R$^8$)C(O)R$^8$, —N(R$^8$)C(O)N(R$^8$)R$^9$, —N(R$^8$)C(NH)N(R$^8$)R$^9$, —OPO$_3$H$_2$ and —SR$^8$;

$R^4$ is —C(NH)—N($R^8$)$R^9$, —C(NH)N(H)O$R^8$, —C(NH)N(H)C(O)$R^8$ or —C(NH)N(H)C(O)O$R^8$;

each $R^5$ is independently:
  hydrogen; or
  alkyl optionally substituted by one or more substituents selected from the group consisting of halo, alkenyl, hydroxy, alkoxy, aryl (optionally substituted by alkyl, hydroxy, halo, —N($R^8$)$R^9$, —C(O)O$R^8$ or —C(O)N($R^8$)$R^9$), aryloxy (optionally substituted by alkyl, hydroxy, halo, —N($R^8$)$R^9$, —C(O)O$R^8$ or —C(O)N($R^8$)$R^9$), aralkoxy (optionally substituted by alkyl, hydroxy, halo, —N($R^8$)$R^9$, —C(O)O$R^8$ or —C(O)N($R^8$)$R^9$), haloalkenyl, cycloalkyl, imidazolyl, indolyl, adamantyl (optionally substituted by halo, alkyl, —N($R^8$)$R^9$, —C(O)O$R^8$ or —C(O)N($R^8$)$R^9$), —C(O)O$R^8$, —N($R^8$)$R^9$, —C(O)N($R^8$)$R^9$, —C(O)(CH$_2$)$_p$O$R^8$ (where p is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —S$R^8$; or
  aryl optionally substituted by alkyl, hydroxy, halo, —N($R^8$)$R^9$, —C(O)O$R^8$, or —C(O)N($R^8$)$R^9$; or
  heterocyclyl optionally substituted by one or more substituents selected from the group consisting of 1-iminoalkyl, —C(O)O$R^8$, —C(O)N($R^8$)$R^9$, —C(NH)N($R^8$)$R^9$, —C(NH)N(H)O$R^8$, —C(NH)N(H)C(O)O$R^8$, —$R^{10}$—C(O)O$R^8$, —$R^{10}$—C(O)N($R^8$)$R^9$ and —SO$_3$H;

$R^6$ is hydrogen, alkyl, —$R^{10}$—C(O)O$R^8$, —$R^{10}$—C(O)N($R^8$)$R^9$, —C(O)$R^7$, or aralkyl (optionally substituted by alkyl, halo, —N($R^8$)$R^9$, —C(O)O$R^8$, or —C(O)N($R^8$)$R^9$);

$R^7$ is a branched or straight chain alkylene substituted by one or more substituents selected from the group consisting of halo, hydroxy, alkoxy, aryl (optionally substituted by alkyl, hydroxy, halo, —N($R^8$)$R^9$, —C(O)O$R^8$), aryloxy, aralkoxy, alkenyl, haloalkenyl, cycloalkyl, imidazolyl, indolyl, adamantyl (optionally substituted by halo, alkyl, hydroxy, —C(O)O$R^8$ or —N($R^8$)$R^9$), —C(O)O$R^8$, —N($R^8$)$R^9$, —C(O)N($R^8$)$R^9$, —C(O)(CH$_2$)$_q$O$R^8$ (where q is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —S$R^8$;

each $R^8$ and $R^9$ is independently hydrogen, alkyl, aryl or aralkyl; and each $R^{10}$ is independently a branched or straight chain alkylene;

or a pharmaceutically acceptable salt thereof.

In another aspect, this invention provides compositions useful in treating a human having a disease-state characterized by thrombotic activity, which composition comprises a therapeutically effective amount of a compound of the invention as described above, or a pharmaceutically acceptable salt thereof, and a pharmaceutically acceptable excipient.

In another aspect, this invention provides a method of treating a human having a disease-state characterized by thrombotic activity, which method comprises administering to a human in need thereof a therapeutically effective amount of a compound of the invention as described above.

In another aspect, this invention provides a method of treating a human having a disease-state alleviated by the inhibition of factor Xa, which method comprises administering to a human in need thereof a therapeutically effective amount of a compound of the invention as described above.

In another aspect, this invention provides a method of treating a human having a disease-state alleviated by the inhibition of factor IIa (thrombin), which method comprises administering to a human in need thereof a therapeutically effective amount of a compound of the invention as described above.

In another aspect, this invention provides a method of inhibiting human factor Xa in vitro or in vivo by the administration of a compound of the invention.

In another aspect, this invention provides a method of inhibiting human factor IIa (thrombin) in vitro or in vivo by the administration of a compound of the invention.

DETAILED DESCRIPTION OF THE INVENTION

Definitions

As used in the specification and appended claims, unless specified to the contrary, the following terms have the meaning indicated:

"Halo" refers to bromo, chloro, fluoro or iodo.

"Alkyl" refers to a straight or branched chain monovalent radical consisting solely of carbon and hydrogen, containing no unsaturation and having from one to six carbon atoms, e.g., methyl, ethyl, n-propyl, isopropyl (1-methylethyl), n-butyl, t-butyl (1,1-dimethylethyl), sec-butyl (1-methylpropyl), n-pentyl, n-hexyl, and the like.

"Alkenyl" refers to a straight or branched chain monovalent radical consisting solely of carbon and hydrogen, containing unsaturation and having from one to six carbon atoms, e.g., ethenyl, n-prop-2-enyl, n-prop-1-enyl, n-but-2-enyl, n-but-3-enyl, 1-methylprop-1-enyl, and the like.

"Alkylene" refers to a straight or branched chain divalent radical consisting solely of carbon and hydrogen, containing no unsaturation and having from one to six carbon atoms, e.g., methylene, ethylene, n-propylene, isopropylene (1-methylethylene), n-butylene, t-butylene (1,1-dimethylethylene), sec-butylene (1-methylpropylene), n-pentylene, n-hexylene, and the like.

"Haloalkenyl" refers to an alkenyl radical, as defined above, substituted by one or more halo atoms, e.g., 1-bromoethenyl, n-1-chloroprop-2-enyl, n-3-chloroprop-1-enyl, n-3-chlorobut-2-enyl, n-4-bromobut-3-enyl, 1-(chloro)methylprop-1-enyl, and the like.

"Alkoxy" refers to a radical of the formula —O$R_a$ where $R_a$ is alkyl as defined above, e.g., methoxy, ethoxy, n-propoxy, t-butoxy, and the like.

"Alkanol" refers to an alkane of one to five carbons which is substituted by a hydroxy radical, e.g., methanol, ethanol, isopropanol, and the like.

"Aryl" refers to the phenyl or naphthyl radical.

"Aralkyl" refers to a radical of the formula —$R_a R_b$ where $R_a$ is alkyl as defined above and $R_b$ is aryl as defined above, e.g., benzyl.

"Aralkoxy" refers to a radical of the formula —O$R_c$ where $R_c$ is aralkyl as defined above, e.g., benzyloxy, (phenyl)ethoxy, and the like.

"Amidino" refers to the radical —C(NH)NH$_2$.

"Heterocyclyl" refers to a stable 5- to 10-membered monocyclic or bicyclic ring radical which is either saturated or unsaturated, and which consists of carbon atoms and from one to three heteroatoms selected from the group consisting of nitrogen, oxygen and sulfur, and wherein the nitrogen, carbon or sulfur atoms may be optionally oxidized, and the nitrogen atom may be optionally quaternized, and including any bicyclic group in which any of the above-defined heterocyclic ring radicals is fused to a benzene molecule. The heterocyclic ring radical may be attached at any heteroatom or carbon atom which results in the creation of a stable structure. Examples of such heterocyclic radicals include, but are not limited to, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, indanyl, isoxazolyl, isoxazolidinyl, morpholinyl, thiazolyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Preferred heterocyclic radicals for the purposes of this invention are imidazolyl, piperidinyl, pyrrolidinyl, and indolyl.

"Cycloalkyl" refers to a 5- to 7-membered ring radical containing solely carbon and hydrogen atoms and no-unsaturation, i.e., cyclopentyl, cyclohexyl, and cycloheptyl.

"Factor IIa" refers to thrombin.

"DEAD" refers to diethyl azodicarboxylate.

"THF" refers to tetrahydrofuran.

"HPLC" refers to high pressure liquid chromotagraphy.

"DMF" refers to dimethylformamide.

"Optional" or "optionally" means that the subsequently described event of circumstances may or may not occur, and that the description includes instances where said event or circumstance occurs and instances in which it does not. For example, "heterocyclyl optionally substituted by one or more substituents selected from the group consisting of 1-iminoalkyl, —C(O)OR$^8$, —C(O)N(R$^8$)R$^9$, —C(NH)N (R$^8$)R$^9$, —C(NH)N(H)OR$^8$, —C(NH)N(H)C(O)OR$^8$, —R$^{10}$—C(O)OR$^8$, —R$^{10}$—C(O)N(R$^8$)R$^9$ and —SO$_3$H" means that the heterocyclic radical, as defined above, may or may not be substituted by the listed substituents and that this description includes both substituted heterocyclic radicals and heterocyclic radicals having no substitution. In addition, it is understood that the various substitutions must be feasibly possible, within the realm of knowledge of a chemist of ordinary skill in the art and result in stable compounds.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethamine, dicyclohexylamine, choline and caffeine.

"Therapeutically effective amount" refers to that amount of a compound of formula (I) which, when administered to a human in need thereof, is sufficient to effect treatment, as defined below, for disease-states alleviated by inhibition of factor Xa or factor IIa. The amount of a compound of formula (I) which constitutes a "therapeutically effective amount" will vary depending on the compound, the disease-state and its severity, and the age of the human to be treated, but can be determined routinely by one of ordinary skill in the art having regard to his own knowledge and to this disclosure.

"Treating" or "treatment" as used herein cover the treatment of a disease-state in a human, which disease-state is alleviated by inhibition of factor Xa or by factor IIa; and include:

(i) preventing the disease-state from occurring in a human, in particular, when such human is predisposed to the disease-state but has not yet been diagnosed as having it;

(ii) inhibiting the disease-state, i.e., arresting its development; or (iii) relieving the disease-state, i.e., causing regression of the disease-state.

The yield of each of the reactions described herein is expressed as a percentage of the theoretical yield.

The compounds of the invention, or their pharmaceutically acceptable salts, may have asymmetric carbon atoms in their structure. The compounds of the invention and their pharmaceutically acceptable salts may therefore exist as single stereoisomers, racemates, and as mixtures of enantiomers and diastereomers. All such single stereoisomers, racemates and mixtures thereof are intended to be within the scope of this invention.

In addition, the compounds of the invention may exist as individual regioisomers or mixtures thereof.

The nomenclature used herein for the compounds of the invention is basically a modified form of the I.U.P.A.C. system, wherein the compounds are named as derivatives of benzimidazole with the following numbering system:

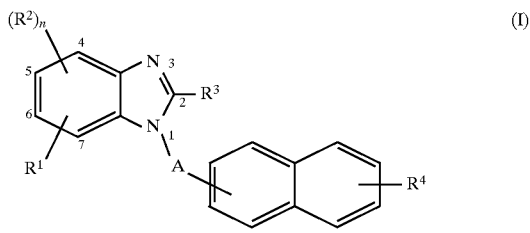

Accordingly, a compound of the invention selected from formula (I) wherein A is methylene, n is 1, R$^1$ is piperidin-4-yloxy substituted on the nitrogen by 1-iminoethyl, R$^2$ is hydrogen, R$^3$ is isopropyl and R$^4$ is —C(NH)NH$_2$, i.e.,

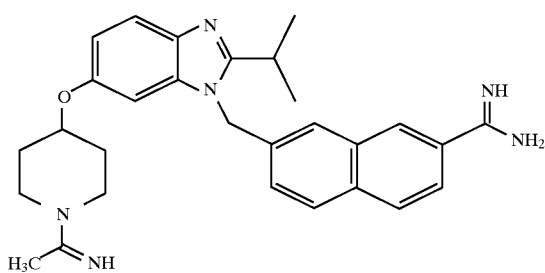

is named herein as 1-(4-amidinonaphth-1-yl)methyl-2-isopropyl-6-(N-(1-iminoethyl)piperidin-4-yloxy)benzimidazole; and wherein its regioisomer, i.e.,

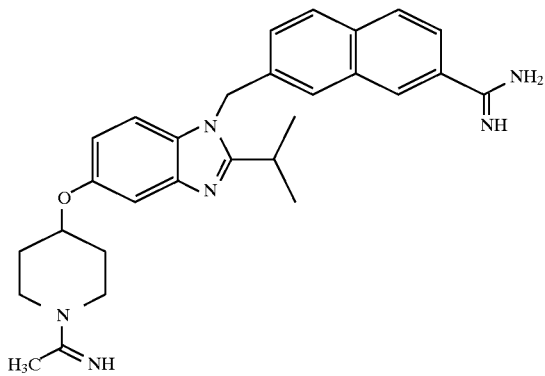

is named herein as 1-(4-amidinonaphth-1-yl)methyl-2-isopropyl-5-(N-(1-iminoethyl)piperidin-4-yloxy)benzimidazole.

Utility and Administration

A. Utility

The compounds of the invention are inhibitors of factor Xa and factor IIa and therefore useful as anti-coagulants in treating disease-states characterized by thrombotic activity based on factor Xa's or factor IIa's role in the coagulation cascade (see Background of the Invention above). A primary indication for the compounds is prophylaxis for long term risk following myocardial infarction. Additional indications are prophylaxis of deep vein thrombosis (DVT) following orthopedic surgery or prophylaxis of selected patients following a transient ischemic attack. The compounds of the invention may also be useful for indications in which coumarin is currently used, such as for DVT or other types of surgical intervention such as coronary artery bypass graft and percutaneous transluminal coronary angioplasty. The compounds are also useful for the treatment of thrombotic complications associated with acute promyelocytic leukemia, diabetes, multiple myelomas, disseminated intravascular coagulation associated with septic shock, purpura fulminanas associated infection, adult respiratory distress syndrome, unstable angina, and thrombotic complications associated with aortic valve or vascular prosthesis. The compounds are also useful for prophylaxis for thrombotic diseases, in particular in patients who have a high risk of developing such disease.

In addition, the compounds of the invention are useful as in vitro diagnostic reagents for inhibiting factor Xa or factor IIa in the coagulation cascade.

B. Testing

The primary bioassays used to demonstrate the inhibitory effect of the compounds of the invention on factor Xa or factor IIa are simple chromogenic assays involving only serine protease, the compound of the invention to be tested, substrate and buffer (see, e.g., Thrombosis Res. (1979), Vol. 16, pp. 245–254). For example, four tissue human serine proteases can be used in the primary bioassay, free factor Xa, prothrombinase, thrombin (factor IIa) and tissue plasminogen activator (tPA). The assay for tPA has been successfully used before to demonstrate undesired side effects in the inhibition of the fibrinolytic process (see, e.g., J. Med. Chem. (1993), Vol. 36, pp. 314–319).

Another bioassay useful in demonstrating the utility of the compounds of the invention in inhibiting factor Xa demonstrates the potency of the compounds against free factor Xa in citrated plasma. For example, the anticoagulant efficacy of the compounds of the invention will be tested using either the prothrombin time (PT), or activated partial thromboplastin time (aPTT) while selectivity of the compounds is checked with the thrombin clotting time (TCT) assay. Correlation of the $K_i$ in the primary enzyme assay with the $K_i$ for free factor Xa in citrated plasma will screen against compounds which interact with or are inactivated by other plasma components. Correlation of the $K_i$ with the extension of the PT is a necessary in vitro demonstration that potency in the free factor Xa inhibition assay translates into potency in a clinical coagulation assay. In addition, extension of the PT in citrated plasma can be used to measure duration of action in subsequent pharmacodynamic studies.

For further information on assays to demonstrate the activity of the compounds of the invention, see R. Lottenberg et al., Methods in Enzymology (1981), Vol. 80, pp. 341–361, and H. Ohno et al., Thrombosis Research (1980), Vol. 19, pp. 579–588.

C. General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state alleviated by the inhibition of factor Xa in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

Preferred Embodiments

Of the compounds of the invention as set forth above in the Summary of the Invention, several groups of compounds are preferred.

One preferred group is that group of compounds of formula (I) wherein n is 0 or 1; A is alkylene; $R^1$ is —$OR^5$ or —$N(R^5)R^6$; each $R^2$ is independently nitro, alkyl (optionally substituted by —$C(O)OR^8$), —$OR^5$, —$N(R^7)R^9$, —$C(O)OR^8$, —$C(O)N(R^8)R^9$ or piperidinyl optionally substituted by —$C(O)OR^8$ or —$R^{10}$—$C(O)OR^8$; $R^3$ is hydrogen or alkyl optionally substituted by one or more substituents selected from the group consisting of halo, —$C(O)OR^8$, or —$C(O)N(R^8)R^9$; $R^4$ is —$C(NH)NH_2$; each $R^5$ is independently hydrogen; or alkyl optionally substituted by one or more substituents selected from the group consisting of —$C(O)OR^8$, —$C(O)N(R^8)R^9$ and phenyl (optionally substituted by —$C(O)OR^8$); or piperidinyl or pyrrolidinyl, each optionally substituted by 1-iminoalkyl, —$C(NH)N(R^8)R^9$, —$R^{10}$—$C(O)OR^8$ or —$SO_3H$; $R^6$ is hydrogen, alkyl, benzyl (optionally substituted by —$C(O)OR^8$), —$R^{10}$—$C(O)OR^8$, —$R^{10}$—$C(O)N(R^8)R^9$ or —$C(O)R^7$; $R^7$ is a branched or straight chain alkylene substituted by one or more substituents selected from the group consisting of —C(O)OR8 and aryl (optionally substituted by —$C(O)OR^8$); each $R^8$ and $R^9$ is independently hydrogen or alkyl; and each $R^{10}$ is independently a branched or straight chain alkylene.

Of this group of compounds, a preferred subgroup of compounds is that subgroup wherein n is 0 or 1; A is methylene: $R^1$ is —$OR^5$ or —$N(R^5)R^6$; $R^2$ is independently nitro, methyl (substituted by —$C(O)OR^8$), —$OR^5$, —$N(R^7)R^9$, —$C(O)OR^8$, —$C(O)N(R^8)R^9$ or piperidinyl optionally substituted by —$C(O)OR^8$ or —$R^{10}$—$C(O)OR^8$; $R^3$ is hydrogen or alkyl optionally substituted by —$C(O)OR^8$ or —$C(O)N(R^8)R^9$; $R^4$ is —$C(NH)NH_2$; each $R^5$ is independently hydrogen; or alkyl optionally substituted by —$C(O)OR^8$, —$C(O)N(R^8)R^9$ or phenyl (optionally substituted by —$C(O)OR^8$); or piperidinyl optionally substituted by 1-iminoalkyl, —$R^{10}$—$C(O)OR^8$ or —$SO_3H$; $R^6$ is hydrogen, alkyl, benzyl (optionally substituted by —$C(O)OR^8$) or —$R^{10}$—$C(O)OR^8$; $R^7$ is a branched or straight chain alkylene substituted by one or more substituents selected from the group consisting of —$C(O)OR^8$ and aryl (optionally substituted by —$C(O)OR^8$); each $R^8$ and $R^9$ is independently hydrogen, methyl or ethyl; and each $R^{10}$ is independently a branched or straight chain alkylene.

Of this subgroup of compounds, a preferred class of compounds is that class wherein n is 0; A is methylene: $R^1$ is —$OR^5$; $R^3$ is hydrogen or alkyl optionally substituted by —$C(O)OR^8$ or —$C(O)N(R^8)R^9$; $R^4$ is —$C(NH)NH_2$; $R^5$ is piperidinyl optionally substituted by 1-iminoalkyl; and $R^8$ and $R^9$ are independently hydrogen, methyl or ethyl.

Of this class of compounds, the following compounds are more preferred:

1-(4-amidinonaphth-1-yl)methyl-2-methyl-6-(N-(1-iminoethyl)piperidin-4-yloxybenzimidazole, 1-(4-amidinonaphth-1-yl)methyl-2-methyl-5-(N-(1-iminoethyl)piperidin-4-yloxybenzimidazole, 1-(4-amidinonaphth-1-yl)methyl-2-methyl-6-(N-(1-iminoethyl)piperidin-3-yloxybenzimidazole, 1-(4-amidinonaphth-1-yl)methyl-2-ethyl-6-(N-(1-iminoethyl)piperidin-4-yloxybenzimidazole, 1-(4-amidinonaphth-1-yl)methyl-2-ethyl-5-(N-(1-iminoethyl)piperidin-4-yloxybenzimidazole, 1-(4-amidinonaphth-1-yl)methyl-2-isopropyl-6-(N-(1-iminoethyl)piperidin-4-yloxybenzimidazole, 1-(4-amidinonaphth-1-yl)methyl-2-isopropyl-5-(N-(1-iminoethyl)piperidin-4-yloxy)benzimidazole, 1-(4-amidinonaphth-1-yl)methyl-2-t-butyl-6-(N-(1-iminoethyl)piperidin-4-yloxy)benzimidazole, 1-(4-amidinonaphth-1-yl)methyl-2-t-butyl-5-(N-(1-iminoethyl)piperidin-4-yloxy)benzimidazole, 1-(4-amidinonaphth-1-yl)methyl-6-(N-(1-iminoethyl)piperidin-4-yloxy)benzimidazole, 1-(4-amidinonaphth-1-yl)methyl-5-(N-(1-iminoethyl)piperidin-4-yloxy)benzimidazole, 1-(4-amidinonaphth-1-yl)methyl-2-propyl-6-(N-(1-iminoethyl)piperidin-4-yloxy)benzimidazole, 1-(4-amidinonaphth-1-yl)methyl-2-propyl-5-(N-(1-iminoethyl)piperidin-4-yloxy)benzimidazole, 1-(4-amidinonaphth-1-yl)methyl-2-propyl-6-(piperidin-4-yloxy)benzimidazole, 1-(4-amidinonaphth-1-yl)methyl-2-propyl-5-(piperidin-4-yloxy)benzimidazole, 1-(4-amidinonaphth-1-yl)methyl-2-isopropyl-6-(piperidin-4-yloxy)benzimidazole, 1-(4-amidinonaphth-1-yl)methyl-2-isopropyl-5-(piperidin-4-yloxy)benzimidazole, 1-(4-amidinonaphth-1-yl)methyl-2-sec-butyl-6-(N-(1-iminoethyl)piperidin-4-yloxy)benzimidazole, 1-(4-amidinonaphth-1-yl)methyl-2-sec-butyl-5-(N-(1-iminoethyl)piperidin-4-yloxy)benzimidazole, 1-(4-amidinonaphth-1-yl)methyl-2-n-butyl-6-(N-(1-iminoethyl)piperidin-4-yloxy)benzimidazole, 1-(4-amidinonaphth-1-yl)methyl-2-n-butyl-5-(N-(1-iminoethyl)piperidin-4-yloxy)benzimidazole, 1-(4-amidinonaphth-1-yl)methyl-2-(2-carboxyethyl)-6-(N-(1-iminoethyl)piperidin-4-yloxy)benzimidazole, 1-(4-amidinonaphth-1-yl)methyl-2-(2-carboxyethyl)-5-(N-(1-iminoethyl)piperidin-4-yloxy)benzimidazole, and 1-(4-amidinonaphth-1-yl)methyl-2-(2-aminocarbonylethyl)-6-(N-(1-iminoethyl)piperidin-4-yloxy)benzimidazole.

Of the subgroup of compounds, another preferred class of compounds is that class wherein n is 0; A is methylene; $R^1$ is —$N(R^5)R^6$; $R^3$ is hydrogen or methyl; $R^4$ is —$C(NH)NH_2$; $R^5$ is piperidinyl optionally substituted by 1-iminoalkyl; $R^6$ is hydrogen, —$R^{10}$—$C(O)OR^8$ or —$C(O)N(R^8)R^9$; $R^8$ and $R^9$ are independently hydrogen or methyl; and $R^{10}$ is a branched or straight chain alkylene.

Of this class of compounds, the following compounds are more preferred:

1-(4-amidinonaphth-1-yl)methyl-6-(N-(1-iminoethyl)piperidin-4-yl)aminobenzimidazole, 1-(4-amidinonaphth-1-yl)methyl-2-methyl-6-(N-(N'-(1-iminoethyl)piperidin-4-yl)-N-((methoxycarbonyl)methyl)amino)benzimidazole, 1-(4-amidinonaphth-1-yl)methyl-2-methyl-6-(N-(N'-(1-iminoethyl)piperidin-4-yl)-N-((aminocarbonyl)methyl)amino)benzimidazole, 1-(4-amidinonaphth-1-yl)methyl-2-methyl-6-(N-(N'-(1-iminoethyl)piperidin-4-yl)-N-(3-carboxypropyl)amino)benzimidazole, 1-(4-amidinonaphth-1-yl)methyl-2-methyl-6-(N-(N'-(1-iminoethyl)piperidin-4-yl)-N-(2-(methoxycarbonyl)propyl)amino)benzimidazole, 1-(4-amidinonaphth-1-yl)methyl-2-methyl-6-(N-(N'-(1-iminoethyl)piperidin-4-yl)-N-(2-(carboxy)propyl)amino)benzimidazole; and 1-(4-amidinonaphth-1-yl)methyl-2-methyl-5-(N-(N'-(1-iminoethyl)piperidin-4-yl)-N-(2-(carboxy)propyl)amino)benzimidazole.

Of the subgroup of compounds, another preferred class of compounds is that class wherein n is 1; A is methylene; $R^1$ is —$OR^5$; $R^2$ is nitro, —$OR^5$, —$N(R^7)R^9$, —$C(O)OR^8$, or piperidinyl (optionally substituted by —$C(O)OR^8$); $R^3$ is methyl or 1-isopropyl; $R^4$ is —$C(NH)NH_2$; each $R^5$ is independently hydrogen or alkyl optionally substituted by —$C(O)OR^8$, —$C(O)N(R^8)R^9$, aryl (optionally substituted by —$C(O)OR^8$), or piperidinyl (optionally substituted by —$R^{10}$—$C(O)OR^8$ or 1-iminoethyl); $R^7$ is a branched or straight chain alkylene substituted by —$C(O)OR^8$ or phenyl (optionally substituted by —$C(O)OR^8$); and each $R^8$ and $R^9$ is independently hydrogen or methyl.

Of this class of compounds, the following compounds are more preferred:

1-(4-amidinonaphth-1-yl)methyl-2-methyl-5-hydroxy-6-(N-(1-iminoethyl)piperidin-4-yloxy)benzimidazole, 1-(4-amidinonaphth-1-yl)methyl-2-methyl-5-(aminocarbonyl)methoxy-6-(N-(1-iminoethyl)piperidin-4-yloxy)benzimidazole, 1-(4-amidinonaphth-1-yl)methyl-2-methyl-5-(carboxy)methoxy-6-(N-(1-iminoethyl)piperidin-4-yloxy)benzimidazole, 1-(4-amidinonaphth-1-yl)methyl-2-methyl-5-(4-(methoxycarbonyl)benzyloxy)-6-(N-(1-iminoethyl)piperidin-4-yloxy)benzimidazole, 1-(4-amidinonaphth-1-yl)methyl-2-methyl-5-(4-(carboxy)benzyloxy)-6-(N-(1-iminoethyl)piperidin-4-yloxy)benzimidazole, 1-(4-amidinonaphth-1-yl)methyl-2-methyl-5-carboxy-6-(N-(1-iminoethyl)piperidin-4-yloxy)benzimidazole, 1-(4-amidinonaphth-1-yl)methyl-2-methyl-5-(3-(methoxycarbonyl)benzyloxy)-6-(N-(1-iminoethyl)piperidin-4-yloxy)benzimidazole, 1-(4-amidinonaphth-1-yl)methyl-2-methyl-5-(3-(carboxy)benzyloxy)-6-(N-(1-iminoethyl)piperidin-4-yloxy)benzimidazole, 1-(4-amidinonaphth-1-yl)methyl-2-methyl-5-(methoxycarbonyl)methoxy-6-(N-(1-iminoethyl)piperidin-4-yloxy)benzimidazole, 1-(4-amidinonaphth-1-yl)methyl-2-methyl-5-(1-(aminocarbonyl)ethoxy)-6-(N-(1-iminoethyl)piperidin-4-yloxy)benzimidazole, 1-(4-amidinonaphth-1-yl)methyl-2-methyl-5-(1-(methoxycarbonyl)ethoxy)-6-(N-(1-iminoethyl)piperidin-4-yloxy)benzimidazole, 1-(4-amidinonaphth-1-yl)methyl-2-methyl-5-(1-(carboxy)ethoxy)-6-(N-(1-iminoethyl)piperidin-4-yloxy)benzimidazole, 1-(4-amidinonaphth-1-yl)methyl-2-isopropyl-4-methoxy-6-(piperidin-4-yloxy)benzimidazole, 1-(4-amidinonaphth-1-yl)methyl-2-isopropyl-7-methoxy-5-(piperidin-4-yloxy)benzimidazole, 1-(4-amidinonaphth-1-yl)methyl-2-isopropyl-4-methoxy-6-(N-(1-iminoethyl)piperidin-4-yloxy)benzimidazole, 1-(4-amidinonaphth-1-yl)methyl-2-isopropyl-7-methoxy-5-(N-(1-iminoethyl)piperidin-4-yloxy)benzimidazole, 1-(4-amidinonaphth-1-yl)methyl-2-methyl-5-(N-(4-carboxy)benzylamino)-6-(N-(1-iminoethyl)piperidin-4-yloxy)benzimidazole, 1-(4-amidinonaphth-1-yl)methyl-2-isopropyl-4-(4-carboxypiperidin-1-yl)-6-(N-(1-iminoethyl)piperidin-4-yloxy)benzimidazole, 1-(4-amidinonaphth-1-yl)methyl-2-isopropyl-4-(carboxy)methoxy-6-(N-(1-iminoethyl)piperidin-4-yloxy)benzimidazole, 1-(4-amidinonaphth-1-yl)methyl-2-isopropyl-7-nitro-6-(N-(1-iminoethyl)piperidin-4-yloxy)benzimidazole, 1-(4-amidinonaphth-1-yl)methyl-2-methyl-7-nitro-6-(N-(1-iminoethyl)piperidin-4-yloxy)benzimidazole, 1-(4-amidinonaphth-1-yl)methyl-2-isopropyl-5-(N-(2-carboxyprop-2-yl)amino)-6-(N-(1-iminoethyl)piperidin-4-yloxy)benzimidazole, 1-(4-amidinonaphth-1-yl)methyl-2-isopropyl-5-(N-(4-carboxy)benzylamino)-6-(N-(1-iminoethyl)piperidin-4-yloxy)benzimidazole, 1-(4-amidinonaphth-1-yl)methyl-2-isopropyl-5-(N-(2-carboxyethyl)amino)-6-(N-(1-iminoethyl)piperidin-4-yloxy)benzimidazole, and 1-(4-amidinonaphth-1-yl)methyl-2-methyl-5-(N-(carboxymethyl)piperidin-4-yloxy)-6-(N-(1-iminoethyl)piperidin-4-yloxy)benzimidazole.

Of the subgroup of compounds, a preferred class of compounds is that class wherein n is 1; A is methylene; $R^1$ is —$N(R^5)R^6$; $R^2$ is —$C(O)OR^8$ or —$C(O)N(R^8)R^9$; $R^3$ is 1-isopropyl; $R^4$ is —$C(NH)NH_2$; $R^5$ is piperidinyl optionally substituted by 1-iminoethyl; $R^6$ is hydrogen; and each $R^8$ and $R^9$ is independently hydrogen or methyl.

Of this class of compounds, the following compounds are more preferred:

1-(4-amidinonaphth-1-yl)methyl-2-isopropyl-4-carboxy-6-(N-(1-iminoethyl)piperidin-4-ylamino)benzimidazole, and 1-(4-amidinonaphth-1-yl)methyl-2-isopropyl-4-aminocarbonyl-6-(N-(1-iminoethyl)piperidin-4-ylamino)benzimidazole.

Preparation of Compounds of The Invention

In the following Reaction Schemes, only one regioisomer is shown as being prepared, although one of ordinary skill in the art, having the full disclosure of this specification, including the Preparations and Examples, would realize that certain steps in the Reaction Schemes result in mixtures of regioisomers, which can be separated and isolated by conventional techniques.

A. Preparation of Compounds of Formulae (Ia) and (Ib).

Compounds of formulae (Ia) and (Ib) are compounds of the invention and are prepared as shown below in Reaction Scheme 1 wherein A is a branched or straight chain alkylene, —C(O)— or —$S(O)_2$—; $R^2$ is alkyl (optionally substituted by halo, aryl, —$C(O)OR^8$, —$C(O)N(R^8)R^9$, —$N(R^8)R^9$, —$OR^5$, —$N(R^7)R^7$, —$N(R^7)R^9$, —$N(R^8)R^9$, —$N(R^8)C(O)R^7$, —$C(O)OR^8$, —$C(O)N(R^7)R^9$, —$C(O)N(R^8)R^9$; $R^3$ is hydrogen or alkyl optionally substituted by one or more substituents selected from the group consisting of halo, alkenyl, hydroxy, alkoxy, aryl (optionally substituted by alkyl, hydroxy, halo, —$N(R^8)R^9$, —$C(O)OR^8$, —$C(O)N(R^8)R^9$), aryloxy (optionally substituted by alkyl, hydroxy, halo, —$N(R^8)R^9$, —$C(O)OR^8$, —$C(O)N(R^8)R^9$), aralkoxy (optionally substituted by alkyl, hydroxy, halo, —$N(R^8)R^9$, —$C(O)OR^8$, —$C(O)N(R^8)R^9$), haloalkenyl, cycloalkyl, imidazolyl, indolyl, adamantyl (optionally substituted by halo, alkyl, —$N(R^8)R^9$, —$C(O)OR^8$ or —$C(O)N(R^8)R^9$), —$C(O)OR^8$, —$N(R^8)R^9$, —$C(O)N(R^8)R^9$, —$C(O)(CH_2)_m OR^8$ (where m is 1 to 4), —$N(R^8)C(O)R^8$, —$N(R^8)C(O)N(R^8)R^9$, —$N(R^8)C(NH)N(R^8)R^9$, —$OPO_3H_2$ and —$SR^8$; $R^5$ is independently hydrogen; or alkyl optionally substituted by one or more substituents selected from the group consisting of halo, alkenyl, hydroxy, alkoxy, aryl (optionally substituted by alkyl, hydroxy, halo, —$N(R^8)R^9$, —$C(O)OR^8$ or —$C(O)N(R^8)R^9$), aryloxy (optionally substituted by alkyl, hydroxy, halo, —$N(R^8)R^9$, —$C(O)OR^8$ or —$C(O)N(R^8)R^9$), aralkoxy (optionally substituted by alkyl, hydroxy, halo, —$N(R^8)R^9$, —$C(O)OR^8$ or —$C(O)N(R^8)R^9$), haloalkenyl, cycloalkyl, imidazolyl, indolyl, adamantyl (optionally substituted by halo, alkyl, —$N(R^8)R^9$, —$C(O)OR^8$ or —$C(O)N(R^8)R^9$), —$C(O)OR^8$, —$N(R^8)R^9$, —$C(O)N(R^8)R^9$, —$C(O)(CH_2)_p OR^8$ (where p is 1 to 4), —$N(R^8)C(O)R^8$, —$N(R^8)C(O)N(R^8)R^9$, —$N(R^8)C(NH)N(R^8)R^9$, —$OPO_3H_2$ and —$SR^8$; or aryl optionally substituted by alkyl, hydroxy, halo, —$N(R^8)R^9$, —$C(O)OR^8$, or —$C(O)N(R^8)R^9$; $R^7$ is a branched or straight chain alkylene substituted by one or more substituents selected from the group consisting of halo, hydroxy, alkoxy, aryl (optionally substituted by alkyl, hydroxy, halo, —$N(R^8)R^9$, —$C(O)OR^8$), aryloxy, aralkoxy, alkenyl, haloalkenyl, cycloalkyl, imidazolyl, indolyl, adamantyl (optionally substituted by halo, alkyl, hydroxy, —$C(O)OR^8$ or —$N(R^8)R^9$), —$C(O)OR^8$, —$N(R^8)R^9$, —$C(O)N(R^8)R^9$, —$C(O)(CH_2)_q OR^8$ (where q is 1 to 4), —$N(R^8)C(O)R^8$, —$N(R^8)C(O)N(R^8)R^9$, —$N(R^8)C(NH)N(R^8)R^9$, —$OPO_3H_2$ and —$SR^8$; each $R^8$ and $R^9$ is as described above in the Summary of the Invention; $R^{11}$ is hydroxy or halo; and X is halo and W is a protecting group for nitrogen such as tert-butoxycarbonyl:

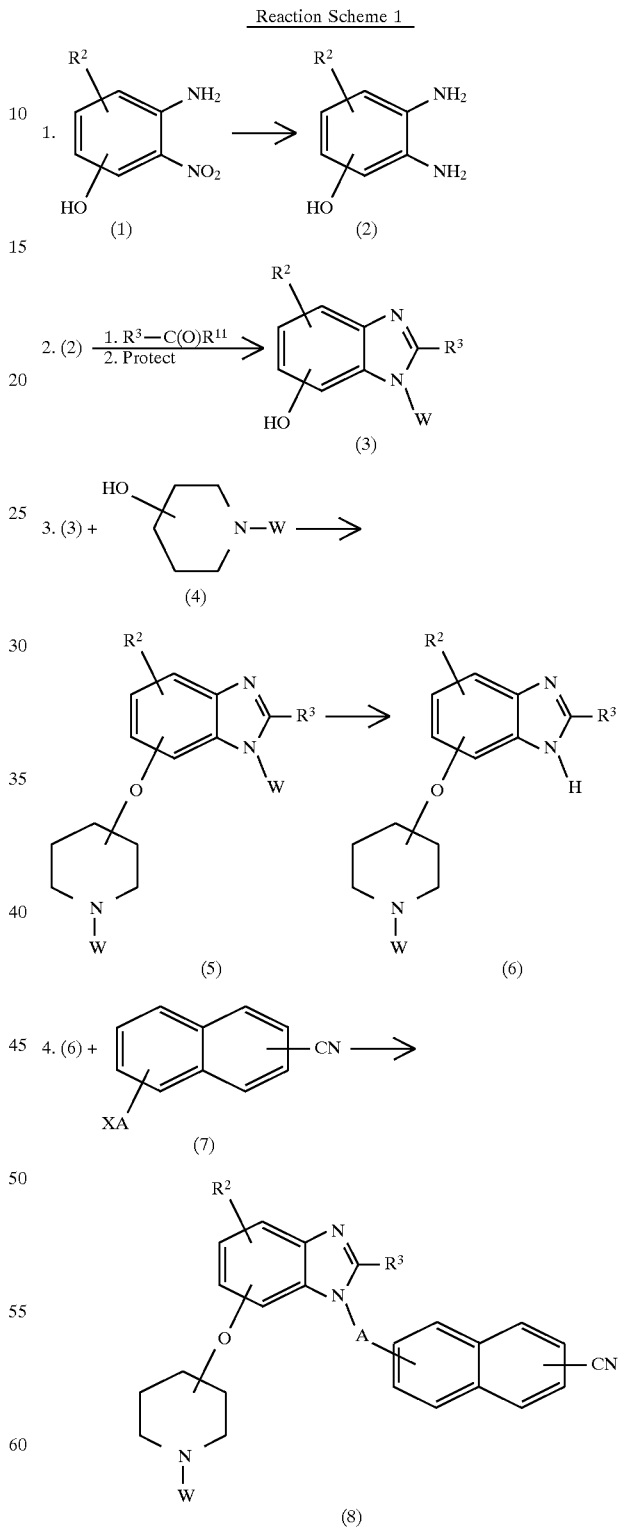

Reaction Scheme 1

-continued
Reaction Scheme 1

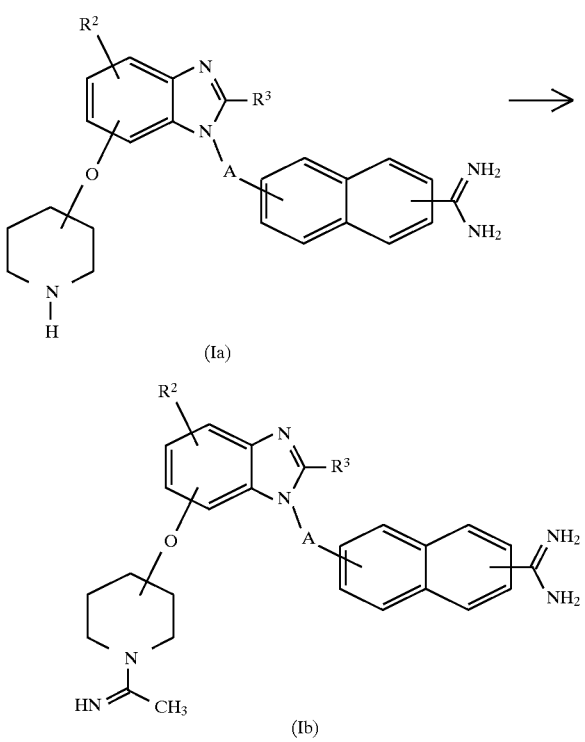

Compounds of formulae (1), (4) and (7) are commercially available, for example, from Aldrich Co., or may be prepared according to methods known to one skilled in the art. Compounds of formula (7) may also be prepared according to the methods disclosed in European Published Patent Application 0 540 051.

In general, compounds of formulae (Ia) and (Ib) are prepared by first treating a compound of formula (1) in a protic solvent, preferably, methanol, with a hydrogenating agent, for example, with palladium on carbon in the presence of hydrogen, for 1 to 24 hours, preferably, for 12 hours, with vigorous shaking. The compound of formula (2) is isolated from the reaction mixture by first treating the reaction mixture with a strong acid, preferably 4N HCl, followed by filtration and concentration.

The compound of formula (2) so formed is then dissolved in an aqueous acidic solvent, such as 4N aqueous HCl, and then an excess molar amount of the compound of formula $R^3$—$C(O)R^{11}$ where $R^{11}$ is hydroxy is added to the solution. The resulting reaction mixture is refluxed for 2 to 16 hours, preferably for 12 hours, and then basified, preferably with potassium bicarbonate, at ambient temperature. The product is isolated from the reaction mixture through extraction and evaporation to yield the unprotected analog of the compound of formula (3). The analog is dissolved in an aprotic solvent, preferably tetrahydrofuran, and treated with di-tert-butyldicarbonate, at ambient temperature, for 2 to 12 hours, preferably for 3 hours. The compound of formula (3) is isolated from the reaction mixture by aqueous extraction, followed by column chromatography.

Alternatively, the compound of formula (2) is dissolved in an aprotic solvent, preferably pyridine, and then treated with the compound of formula $R^3$—$C(O)R^{11}$ where $R^{11}$ is chloro. The resulting reaction mixture is stirred for 4 to 16 hours, preferably for 16 hours, at ambient temperature. The product is isolated from the reaction mixture by aqueous extraction and recrystallization to produce an intermediate amide, which is treated with a mineral acid, preferably 1N HCl. The resulting reaction mixture is refluxed for 2 to 12 hours, preferably for 3 hours, and then basified at ambient temperature. The resulting compound is dissolved in an aprotic solvent, preferably tetrahydrofuran, and treated with di-tert-butyldicarbonate, at ambient temperature, for 2 to 12 hours, preferably for 3 hours. The compound of formula (3) is then isolated from the reaction mixture in a manner similar to that which is described above.

The compound of formula (3) is then dissolved in an aprotic solvent, preferably, tetrahydrofuran, to which is added the compound of formula (4) in the presence of triphenylphosphine and diethylazodicarboxylate (DEAD) in excessive molar amount at ambient temperature. The resulting reaction mixture is stirred for 1 to 14 hours, preferably for 12 hours. Isolation by column chromatography yielded the compound of formula (5), which is then dissolved in a protic solvent, preferably, methanol. The resulting solution is then treated with a base, preferably ammonia, in a sealed flask and stirred for 2 to 16 hours, preferably, for 3 hours, at 45° C. to 70° C., preferably, at 50° C. The compound of formula (6) is then isolated from the reaction mixture through conventional techniques, such as concentration and column chromatography.

The compound of formula (6) is then dissolved in an aprotic solvent, preferably, DMF, and treated with a strong inorganic base, such as sodium hydride. The resulting reaction mixture is stirred for 30 minutes to 3 hours, preferably for 1 hour, at ambient temperature. A compound of formula (7) is then added to the reaction mixture, and the resulting mixture is stirred for 1 to 24 hours, preferably for 20 hours, at ambient temperature. Isolation through conventional techniques, such as aqueous extraction and column chromatography yielded the compound of formula (8).

The compound of formula (8) is then dissolved in an anhydrous alkanol, preferably ethanol and the resulting solution is then treated with an anhydrous mineral acid, preferably HCl, while maintaining the reaction temperatures between about −78° C. and ambient temperature for between 2 hours and 24 hours, and allowing the temperature to rise to ambient temperature while monitoring for reaction completion, for example, through reverse phase HPLC. The solvent is then removed and the resulting residue dissolved in fresh anhydrous alkanol, preferably ethanol. The resulting solution is then treated with anhydrous ammonia at ambient pressure or in a sealed flask, at temperatures from between ambient temperature and 100° C. for about 1 to about 5 hours. The compound of formula (Ia) are then isolated from the reaction mixture by standard techniques, such as concentration and reverse phase HPLC.

Alternatively, instead of treating the resulting solution above with anhydrous ammonia, the resulting solution is treated with a compound of the formula —$NH_2OR^8$ to prepare the corresponding compound of formula (Ia) wherein $R^4$ is —$C(NH)N(H)OR^8$ substituent.

The compound of formula (Ia) may then be dissolved in a protic solvent, preferably methanol, and then, in the presence of a base, preferably triethylamine, be treated with the appropriate imidate, preferably ethyl acetimidate, at ambient temperature, for 1 to 16 hours, preferably for 3 hours. The product, the compound of formula (Ib), is isolated from the reaction mixture by standard techniques, such as concentration and reverse phase HPLC.

Compounds of formulae (Ia) and (Ib) wherein $R^2$ contains —$C(O)N(R^8)R^9$ or —$C(O)OR^8$ where each $R^8$ and $R^9$ are independently alkyl, aryl or aralkyl may be hydrolyzed under acidic conditions to prepare compounds of formula (Ia) and (Ib) where $R^2$ contains —$C(O)OR^8$ where $R^8$ is hydrogen.

Compounds of formula (Ia) and (Ib) where $R^2$ contains —C(O)OR$^8$ where $R^8$ is hydrogen may be amidated or esterified under standard conditions to produce compounds of formulae (Ia) and (Ib) where $R^2$ contains —C(O)OR$^8$ where $R^8$ is alkyl, aryl or aralkyl, or compounds of formulae (Ia) and (Ib) where $R^2$ contains —C(O)N($R^8$)$R^9$ or —C(O)N($R^7$)$R^9$ where $R^8$ and $R^9$ are independently hydrogen, alkyl, aryl or aralkyl and $R^7$ is as defined above in the Summary of the Invention.

Compounds of formulae (Ia) and (Ib) where $R^2$ is nitro may be reduced under standard conditions to produce compounds of formulae (Ia) and (Ib) where $R^2$ is amino, which can further be treated with the appropriate alkylating agent to produce compounds of formulae (Ia) and (Ib) where $R^2$ is —N($R^7$)$R^7$, —N($R^7$)$R^9$, —N($R^8$)$R^9$ or —N($R^8$)C(O)$R^7$ where each $R^8$ and $R^9$ is hydrogen, alkyl, aryl or aralkyl and $R^7$ is as defined above in the Summary of the Invention.

Compounds of formula (Ib) may further be treated with the appropriate acid halides, preferably acid chlorides, or with the appropriate acid anhydrides or equivalents, to yield compounds of the invention wherein $R^4$ is —C(NH)N(H)C(O)$R^8$. Alternatively, compounds of formula (Ib) may further be treated with carbamoyl chlorides, or their equivalents, to yield compounds of the invention where $R^4$ is —C(NH)N(H)C(O)OR$^8$.

B. Preparation of Compounds of Formula (14a)

Compounds of formula (14a) are intermediates in the preparation of the compounds of the invention and are prepared as shown below in Reaction Scheme 2 wherein $R^3$ is hydrogen or alkyl optionally substituted by one or more substituents selected from the group consisting of halo, alkenyl, hydroxy, alkoxy, aryl (optionally substituted by alkyl, hydroxy, halo, —N($R^8$)$R^9$, —C(O)OR$^8$, —C(O)N($R^8$)$R^9$), aryloxy (optionally substituted by alkyl, hydroxy, halo, —N($R^8$)$R^9$, —C(O)OR$^8$, —C(O)N($R^8$)$R^9$), aralkoxy (optionally substituted by alkyl, hydroxy, halo, —N($R^8$)$R^9$, —C(O)OR$^8$, —C(O)N($R^8$)$R^9$), haloalkenyl, cycloalkyl, imidazolyl, indolyl, adamantyl (optionally substituted by halo, alkyl, —N($R^8$)$R^9$, —C(O)OR$^8$ or —C(O)N($R^8$)$R^9$), —C(O)OR$^8$, —N($R^8$)$R^9$, —C(O)N($R^8$)$R^9$, —C(O)(CH$_2$)$_m$OR$^8$ (where m is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —SR$^8$; $R^5$ is hydrogen; or $R^5$ is alkyl optionally substituted by one or more substituents selected from the group consisting of halo, alkenyl, hydroxy, alkoxy, aryl (optionally substituted by alkyl, hydroxy, halo, —N($R^8$)$R^9$, —C(O)OR$^8$ or —C(O)N($R^8$)$R^9$), aryloxy (optionally substituted by alkyl, hydroxy, halo, —N($R^8$)$R^9$, —C(O)OR$^8$ or —C(O)N($R^8$)$R^9$), aralkoxy (optionally substituted by alkyl, hydroxy, halo, —N($R^8$)$R^9$, —C(O)OR$^8$ or —C(O)N($R^8$)$R^9$), haloalkenyl, cycloalkyl, imidazolyl, indolyl, adamantyl (optionally substituted by halo, alkyl, —N($R^8$)$R^9$, —C(O)OR$^8$ or —C(O)N($R^8$)$R^9$), —C(O)OR$^8$, —N($R^8$)$R^9$, —C(O)N($R^8$)$R^9$, —C(O)(CH$_2$)$_p$OR$^8$ (where p is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —SR$^8$; $R^8$, $R^9$ and $R^{10}$ are as defined above in the Summary of the Invention; $R^{11}$ is hydroxy or halo; Y is a protecting group for oxygen, such as tetrabutyldimethylsilyl, and W is a protecting group for nitrogen, such as tert-butoxycarbonyl:

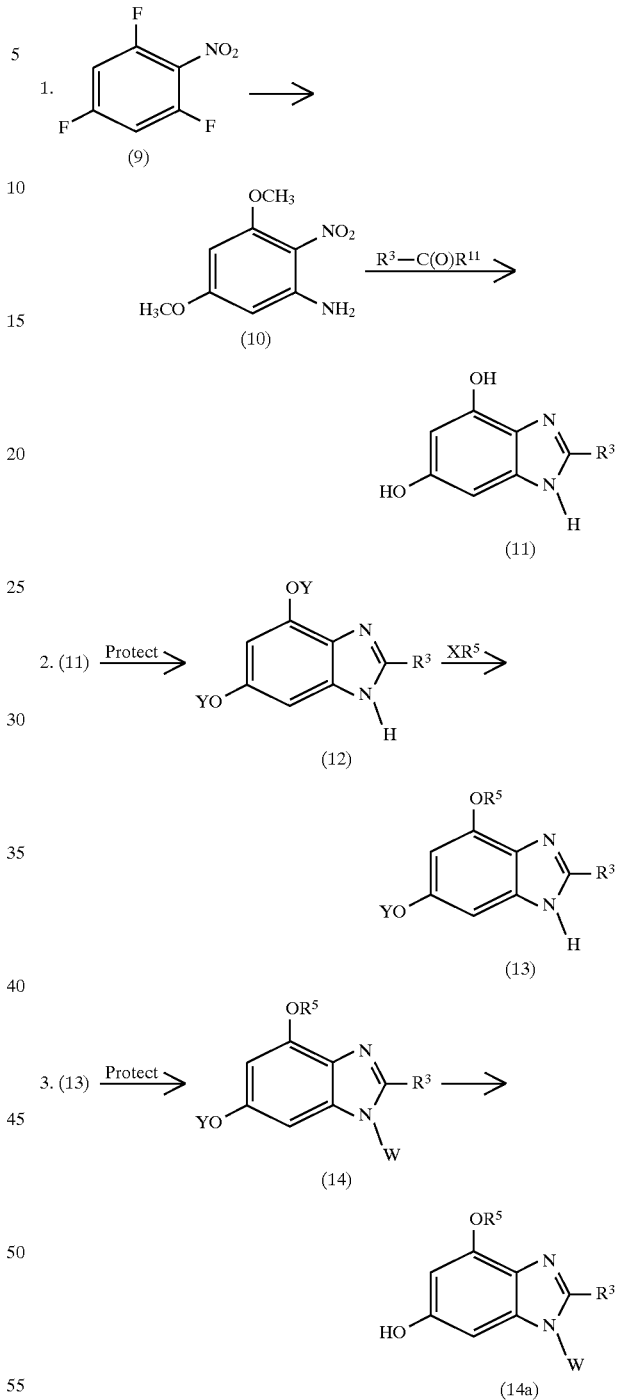

Compounds of formula (9) and the acid chloride used in Step 1 are commercially available, for example, from Lancaster Synthesis, Inc., or may be prepared according to methods known to those skilled in the art.

In general, the compounds of formula (14a) are prepared by first dissolving a compound of formula (9) in an aprotic solvent, preferably tetrahydrofuran, and saturating the solution with ammonia (gas) at 0° C. After the saturation, the reaction mixture is sealed and warmed to ambient temperature and stirred for 3 to 16 hours, preferably for 12 hours. The reaction mixture is filtered and the filtrate is concentrated and dissolved in a protic solvent, preferably methanol, and treated with an excessive molar amount of an alkaline alkoxide, preferably sodium methoxide, and the reaction mixture is stirred at ambient temperature for 1 to 6 hours, preferably 3 hours. The compound of formula (10) was isolated from the reaction mixture through standard isolation techniques, such as extraction and concentration.

The compound of formula (10) is then dissolved in an aprotic basic solvent, such as pyridine, and treated with a slight molar excess of the compound of formula $R^3$—C(O)Cl. The reaction mixture is stirred for 1 to 16 hours, preferably for 1 hour, at room temperature. Isolation through conventional isolation techniques, such as evaporation, aqueous extraction and recrystallization, afforded the corresponding amide. The amide is dissolved in a protic solvent, preferably ethanol, in the presence of a strong acid, for example, 4N HCl, and then reduced under standard reducing conditions, such as palladium on carbon in the presence of hydrogen, to form the corresponding amine, which is isolated from the reaction mixture through standard techniques, such as filtration and concentration. The resulting product is then dissolved in a mineral acid, such as 2N HCl, and refluxed for 3 to 12 hours, preferably 4 hours. The product is isolated through concentration and dissolved in aqueous hydrogen bromide and refluxed for 1 to 16 hours, preferably 3 hours. The product is concentrated and redissolved in $H_2O$ and an inorganic base, such as potassium bicarbonate. The compound of formula (11) is isolated from the reaction mixture by conventional methods, such as aqueous extraction and concentration.

The compound of formula (11) is then dissolved in an aprotic solvent, preferably, DMF, to which a weak base, such as imidazole, is added. To this reaction mixture is added an excessive molar amount of a bulky silyl halide, such as tert-butyldimethylsilyl chloride. The resulting reaction mixture is stirred for 1 to 12 hours, preferably for 1 hour, at ambient temperature. The compound of formula (12) is then isolated from the reaction mixture through standard techniques, such as extraction and concentration.

The compound of formula (12) is then dissolved in an aprotic solvent, such as DMF, and treated with a strong base, such as sodium hydride, at ambient temperature. The reaction is stirred for 1 to 6 hours, preferably for 4 hours, and the compound of formula $XR^5$ is added to the reaction mixture, while stirring, over a period of 1 to 3 hours. The compound of formula (13) is isolated from the reaction mixture by standard techniques, such as extraction and column chromatography.

The benzimidazole nitrogen of the compound of formula (13) is then protected in a manner similar to the process described above for a compound of formula (2) to produce the compound of formula (14). The compound of formula (14) is then dissolved in an aprotic solvent, such as DMF, and cooled to 0° C. Tetra-butyl ammonium fluoride, in an aprotic solvent, is then added to the solution, and the resulting mixture was stirred for 30 minutes to 3 hours, preferably for 1 hour at 0° C. The compound of formula (14a) is then isolated from the reaction mixture through standard techniques, such as aqueous extraction and column chromatography.

The compound of formula (14a) may then be treated in a manner similar as described above for compound of formula (3) to produce compounds of the invention.

In addition, the dimethoxybenzimidazole compound formed in the process of making the compound of formula (11) from the compound of formula (10) may be dissolved in aqueous hydrogen bromide and refluxed for a shorter time period, preferably, for about 3 hours, to produce the corresponding mono-hydroxymethoxy benzimidazole of compound (13), i.e., the compound wherein $R^5$ is methyl and Y is hydrogen. This compound is then treated in the similar manner as described above for the compound of formula (13) to produce compounds of the invention.

C. Preparation of Compounds of Formula (22)

Compounds of formula (22) are intermediates in the preparation of the compounds of the invention and are prepared as shown below in Reaction Scheme 3 wherein $R^3$ is hydrogen or alkyl optionally substituted by one or more substituents selected from the group consisting of halo, alkenyl, hydroxy, alkoxy, aryl (optionally substituted by alkyl, hydroxy, halo, —N(R$^8$)R$^9$, —C(O)OR$^8$, —C(O)N(R$^8$)R$^9$), aryloxy (optionally substituted by alkyl, hydroxy, halo, —N(R$^8$)R$^9$, —C(O)OR$^8$, —C(O)N(R$^8$)R$^9$), aralkoxy (optionally substituted by alkyl, hydroxy, halo, —N(R$^8$)R$^9$, —C(O)OR$^8$, —C(O)N(R$^8$)R$^9$), haloalkenyl, cycloalkyl, imidazolyl, indolyl, adamantyl (optionally substituted by halo, alkyl, —N(R$^8$)R$^9$, —C(O)OR$^8$ or —C(O)N(R$^8$)R$^9$), —C(O)OR$^8$, —N(R$^8$)R$^9$, —C(O)N(R$^8$)R$^9$, —C(O)(CH$_2$)$_m$OR$^8$ (where m is 1 to 4), —N(R$^8$)C(O)R$^8$, —N(R$^8$)C(O)N(R$^8$)R$^9$, —N(R$^8$)C(NH)N(R$^8$)R$^9$, —OPO$_3$H$_2$ and —SR$^8$; R$^8$ and R$^9$ are each independently hydrogen, alkyl, aryl or aralkyl; R$^{10}$ is a branched or straight chain alkylene; R$^{12}$ is alkyl; X is halo; M is an alkaline metal anion and W is a protecting group for nitrogen, such as tert-butoxycarbonyl:

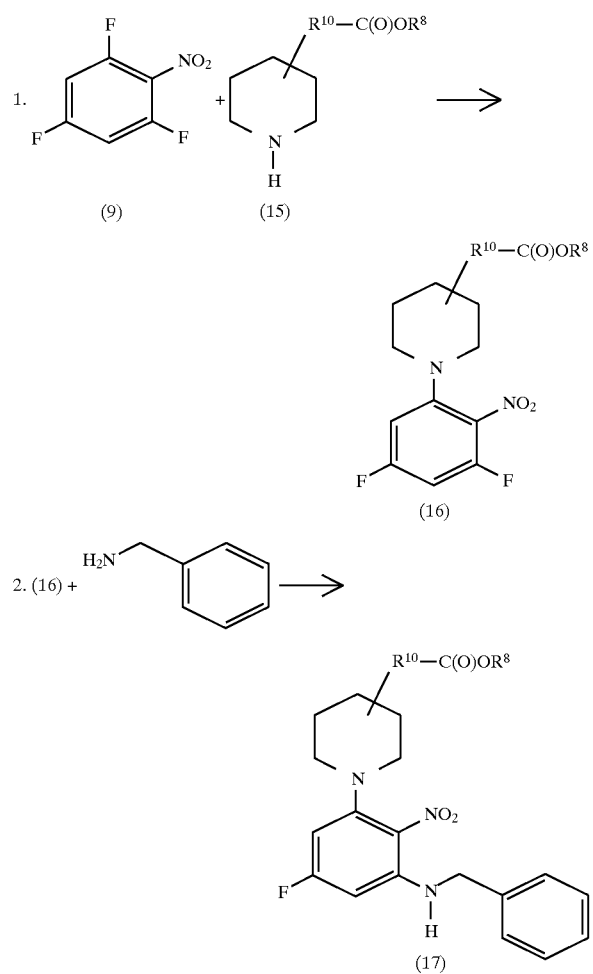

-continued
Reaction Scheme 3

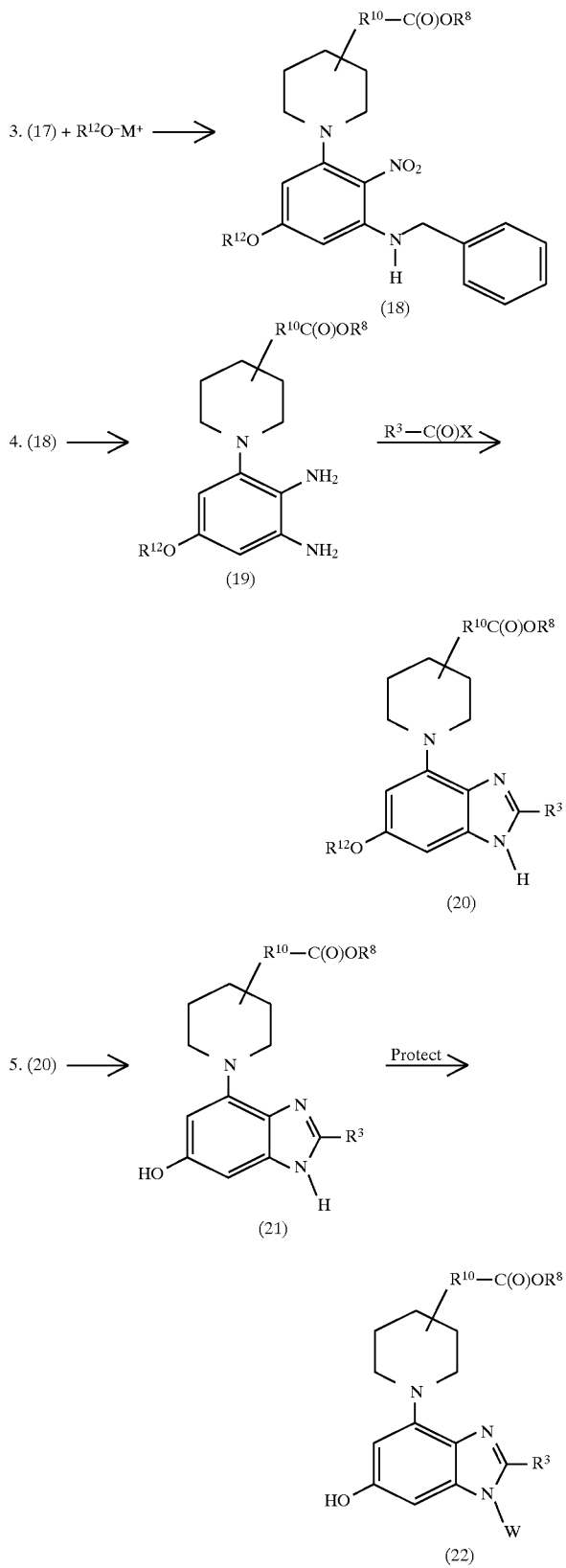

Compounds of formulae (9) and (15), and the acid halide used in Step 4 are commercially available or may be prepared according to methods known to those skilled in the art.

In general, compounds of formula (22) are prepared by first dissolving a compound of formula (9) in an aprotic solvent, preferably acetonitrile, and the resulting solution is chilled to about −10° C. An equivalent molar amount of a compound of formula (15) is then added to the solution in the presence of a base, preferably diisopropylethylamine, and the resulting solution is allowed to warm to ambient temperature. The reaction mixture is stirred for 3 to 12 hours, preferably for 5 hours. Isolation through conventional techniques, such as evaporation of the solvent, extraction and concentration, yields the corresponding compound of formula (16).

The compound of formula (16) is then dissolved in an aprotic solvent, preferably acetonitrile and the resulting solution is chilled to about −10° C. Benzylamine is added slowly to the solution in the presence of a base, preferably diisopropylethylamine, and the resulting reaction mixture is allowed to warm to ambient temperature. The reaction mixture is then refluxed for 24 to 48 hours, preferably for about 24 hours. Conventional isolation techniques, such as removal of the solvent, aqueous organic extraction, and concentration yields the compound of formula (17).

The compound of formula (17) is then dissolved in a protic solvent, preferably a alkanol such as methanol. An excessive molar amount of an alkaline alkoxide corresponding to the alkanol used, such as sodium methoxide, is then added to the reaction mixture under nitrogen. The resulting mixture is refluxed for 1 to 12 hours, preferably for 6 hours, and the reaction allowed to cool to ambient temperature. The solvent is removed and the resulting residue is dissolved in an organic solvent. Conventional isolation techniques, such as aqueous extraction, concentration and chromatography yields the compound of formula (18).

The compound of formula (18) is then dissolved in a protic solvent and treated with a reducing agent, such as palladium on carbon, in the presence of an acid, such as HCl. The resulting mixture is then hydrogenated under pressure and the solids filtered out of the solution to yield the HCl salt of the compound of formula (19).

The salt form of the compound of formula (19) is dissolved in an organic basic solvent, preferably, pyridine. An excessive molar amount of a compound of formula $R^3$—C(O)X is added to the solution at about 0° C. The mixture is allowed to warm to ambient temperature and then stirred for 12–16 hours, preferably for 12 hours. The solvent is removed and conventional isolation techniques, such as extraction an organic solvent and concentration, provides the product which is then dissolved in a strong mineral acid, preferably 4N HCl and the resulting solution is refluxed for 8 to 16 hours, preferably 16 hours. The acid is removed by evaporation and the resulting residue is then neutralized to pH 7 with a mild inorganic base, such as sodium bicarbonate. Standard isolation techniques, such as removal of the resulting water by concentration and trituration with tetrahydrofuran, provides the compound of formula (20).

The compound of formula (20) is then dealkylated in a manner similar to that described above for compounds of formula (11) to produce a compound of formula (21) and N-protected in a manner similar to that described above for compounds of formula (2) to produce the compound of formula (22).

The resulting compound of formula (22) is then treated in a manner similar to that described in Reaction Scheme 1 for compounds of formula (3) to produce compounds of the invention.

D. Preparation of Compounds of Formula (32)

Compounds of formula (32) are intermediates in the preparation of the compounds of the invention and are prepared as shown below for Reaction Scheme 4 wherein A is a branched or straight chain alkylene; $R^3$ is hydrogen or alkyl optionally substituted by one or more substituents selected from the group consisting of halo, alkenyl, hydroxy, alkoxy, aryl (optionally substituted by alkyl, hydroxy, halo, —N($R^8$)$R^9$, —C(O)O$R^8$, —C(O)N($R^8$)$R^9$), aryloxy (optionally substituted by alkyl, hydroxy, halo, —N($R^8$)$R^9$, —C(O)O$R^8$, —C(O)N($R^8$)$R^9$), aralkoxy (optionally substituted by alkyl, hydroxy, halo, —N($R^8$)$R^9$, —C(O)O$R^8$, —C(O)N($R^8$)$R^9$), haloalkenyl, cycloalkyl, imidazolyl, indolyl, adamantyl (optionally substituted by halo, alkyl, —N($R^8$)$R^9$, —C(O)O$R^8$ or —C(O)N($R^8$)$R^9$), —C(O)O$R^8$, —N($R^8$)$R^9$, —C(O)N($R^8$)$R^9$, —C(O)(CH$_2$)$_m$O$R^8$ (where m is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —S$R^8$; $R^5$ is hydrogen; or $R^5$ is alkyl optionally substituted by one or more substituents selected from the group consisting of halo, alkenyl, hydroxy, alkoxy, aryl (optionally substituted by alkyl, hydroxy, halo, —N($R^8$)$R^9$, —C(O)O$R^8$ or —C(O)N($R^8$)$R^9$), aryloxy (optionally substituted by alkyl, hydroxy, halo, —N($R^8$)$R^9$, —C(O)O$R^8$ or —C(O)N($R^8$)$R^9$), aralkoxy (optionally substituted by alkyl, hydroxy, halo, —N($R^8$)$R^9$, —C(O)O$R^8$ or —C(O)N($R^8$)$R^9$), haloalkenyl, cycloalkyl, imidazolyl, indolyl, adamantyl (optionally substituted by halo, alkyl, —N($R^8$)$R^9$, —C(O)O$R^8$ or —C(O)N($R^8$)$R^9$), —C(O)O$R^8$, —N($R^8$)$R^9$, —C(O)N($R^8$)$R^9$, —C(O)(CH$_2$)$_p$O$R^8$ (where p is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —S$R^8$; or $R^5$ is aryl optionally substituted by alkyl, hydroxy, halo, —N($R^8$)$R^9$, —C(O)O$R^8$, or —C(O)N($R^8$)$R^9$; $R^8$, $R^9$ and $R^{10}$ are as defined above in the Summary of the Invention; X is halo; each Y is an oxygen protecting group, such as tert-butyldimethylsilyl; and each W is a nitrogen protecting group such as tert-butoxycarbonyl:

Reaction Scheme 4

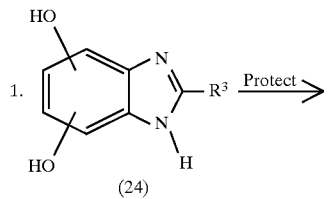

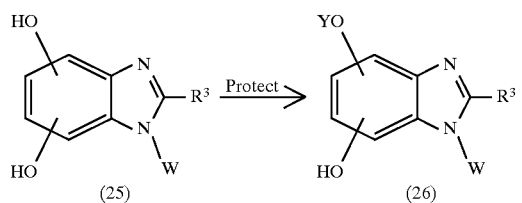

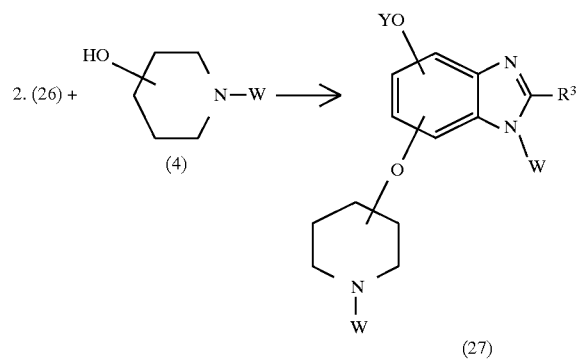

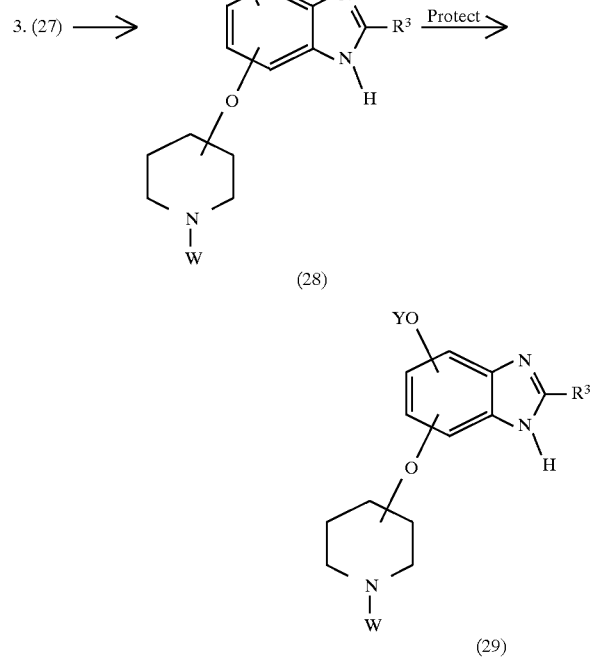

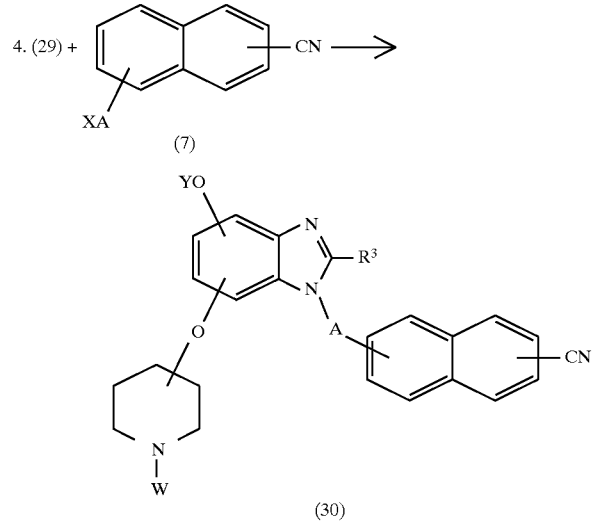

-continued
Reaction Scheme 4

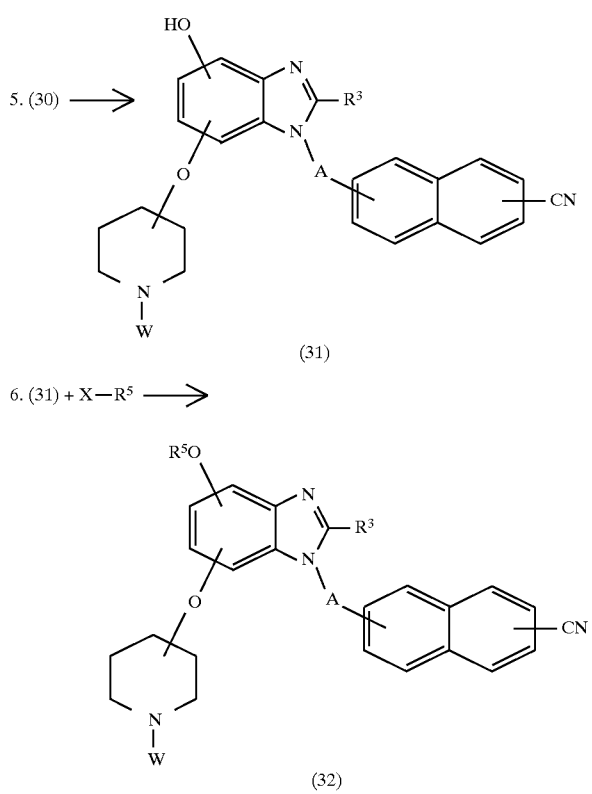

Compounds of formulae (24), (4) and (7) are commercially available or may be prepared by methods known to those skilled in the art or by the methods disclosed herein.

In general, the compounds of formula (32) are prepared by first dissolving a compound of formula (24) in an aprotic solvent, preferably, tetrahydrofuran. The solution is basified to a pH of 7 to 10, preferably, to pH 8, with a mild inorganic base, preferably, sodium bicarbonate, at ambient temperature. An excessive molar amount of a nitrogen-protecting reagent, such as di-tert-butyldicarbonate, is added to the solution and the resulting mixture was stirred at ambient temperature for 0.5 to 24 hours, preferably for 12 hours. The solvent is removed and the resulting residue is diluted and extracted with an organic solvent. Extraction and concentration provides the compound of formula (25).

The compound of formula (25) is then dissolved in an aprotic solvent, preferably, DMF. A mild base, preferably, imidazole, and an oxygen-protecting reagent, such as tert-butyldimethylsilyl chloride, is added to the solution. The resulting mixture is stirred for 30 minutes to 5 hours, preferably for 1 hour, at ambient temperature. The compound of formula (26) is isolated from the reaction mixture by extraction and evaporation.

The compound of formula (26) is then dissolved in an aprotic solvent, preferably, tetrahydrofuran, and then reacted in a manner similar to that described above for compounds of formula (3) to produce the compound of formula (27).

The compound of formula (27) is then dissolved in a protic solvent, preferably, methanol, and then deprotected by ammonolysis at 0° to 50° C., preferably at 20° C., while stirring for 5 to 48 hours, preferably for 12 hours. Conventional isolation techniques, such as concentration and drying provides the compound of formula (28).

The compound of formula (28) is then dissolved in an aprotic solvent, preferably DMF, and O-protected in a manner similar to that described above for the compound of formula (26) to produce the compound of formula (29).

The compound of formula (29) is then treated in a similar manner as that described above for the compounds of formula (6) to provide compounds of formula (30). The compound of formula (30) is then dissolved in an aprotic solvent, preferably, tetrahydrofuran, and treated with a deprotecting agent, such as tetrabutyl ammonium fluoride, at ambient temperature. After stirring the reaction mixture for 30 minutes to an hour, preferably for 30 minutes, the compound of formula (31) is isolated from the reaction mixture through conventional techniques, such as extraction and concentration.

The compound of formula (31) is then dissolved in an aprotic solvent, such as DMF. A strong base, such as sodium hydride, is added to the solution, and the resulting mixture is allowed to stir for 30 minutes to 2 hours, preferably for 30 minutes, at ambient temperature. The compound of formula $XR^5$ is added to the reaction mixture, and the resulting mixture is stirred for 30 minutes to 3 hours, preferably, for 1 hour. The compound of formula (32) is then isolated from the reaction mixture through conventional isolation techniques, such as aqueous extraction, concentration and column chromatography.

The compound of formula (32) is then treated in a similar manner as that described above for compounds of formula (8) to provide compounds of the invention.

E. Preparation of Compounds of Formula (36)

Compounds of formula (36) are intermediates in the preparation of the compounds of the invention and are prepared as shown below in Reaction Scheme 5 wherein A is a straight or branched chain alkylene; $R^3$ is hydrogen or alkyl optionally substituted by one or more substituents selected from the group consisting of halo, alkenyl, hydroxy, alkoxy, aryl (optionally substituted by alkyl, hydroxy, halo, —N($R^8$)$R^9$, —C(O)O$R^8$, —C(O)N($R^8$)$R^9$), aryloxy (optionally substituted by alkyl, hydroxy, halo, —N($R^8$)$R^9$, —C(O)O$R^8$, —C(O)N($R^8$)$R^9$), aralkoxy (optionally substituted by alkyl, hydroxy, halo, —N($R^8$)$R^9$, —C(O)O$R^8$, —C(O)N($R^8$)$R^9$), haloalkenyl, cycloalkyl, imidazolyl, indolyl, adamantyl (optionally substituted by halo, alkyl, —N($R^8$)$R^9$, —C(O)O$R^8$ or —C(O)N($R^8$)$R^9$), —C(O)O$R^8$, —N($R^8$)$R^9$, —C(O)N($R^8$)$R^9$, —C(O)(CH$_2$)$_m$O$R^8$ (where m is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —S$R^8$; $R^8$, $R^9$ and $R^{10}$ are as defined above in the Summary of the Invention; X is halo; Y is a protecting group for oxygen, such as tert-butyldimethylsilyl; and $W^1$ is a protecting group for nitrogen, such as tert-butoxycarbonyl and $W^2$ is a different protecting group for nitrogen, such as benzyloxycarbonyl (CBZ):

Reaction Scheme 5

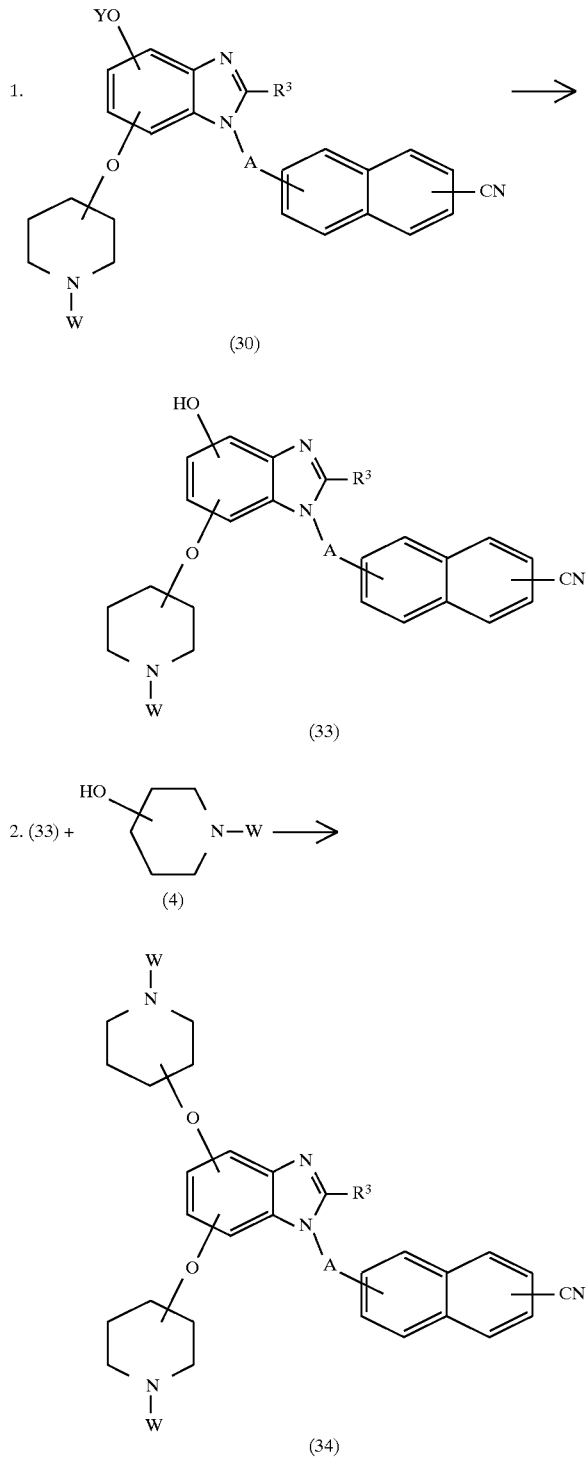

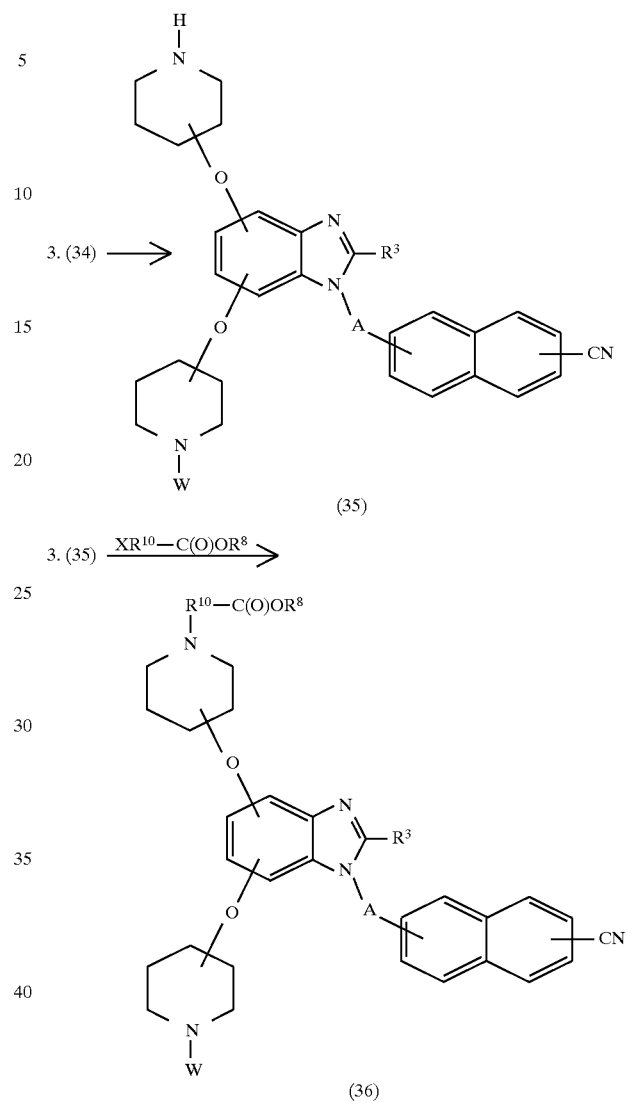

Compounds of formula (30) are prepared according to methods disclosed herein. Compounds of formula (4) and $XR^{10}$—$C(O)OR^8$ are commercially available, or may be prepared according to methods known to those skilled in the art.

In general, compounds of formula (36) are prepared by first dissolving a compound of formula (30) in an aprotic solvent, such as tetrahydrofuran, and then treating the resulting solution in a manner similar to that as described above for compounds of formula (30) to produce a compound of formula (33).

The compound of formula (33) is then treated with a compound of formula of formula (4) in a similar manner as described above for compounds of formula (26) to produce a compound of formula (34).

The compound of formula (34) is then dissolved in a mixture of a protic and an aprotic solvent, such as a 9:1 mixture of methylene chloride and methanol. An organic acid, such as trifluoroacetic acid, is then added to the solution. The resulting reaction mixture is stirred for 3 to 24 hours, preferably for 6 hours, at ambient temperature. The compound of formula (35) is then isolated from the reaction mixture by conventional techniques, such as concentration.

The compound of formula (35) is then dissolved in an aprotic solvent, such as tetrahydrofuran. A compound of formula $XR^{10}$—$C(O)OR^8$ in the presence of a mild base, preferably, potassium carbonate. The resulting reaction mixture is stirred at ambient temperature for 30 minutes to 6 hours, preferably for 1 hour. Conventional isolation techniques, such as extraction with an organic solvent, drying, concentration and chromatography provides a compound of formula (36).

The compound of formula (36) is then treated in a manner similar to that described above for the compound of formula (8) to provide compounds of the invention.

F. Preparation of Compounds of Formula (45)

Compounds of formula (45) are intermediates in the preparation of compounds of the invention and are prepared as shown below in Reaction Scheme 6 wherein A is a branched or straight chain alkylene; $R^2$ is alkyl (optionally substituted by halo, aryl, —C(O)OR$^8$, —C(O)N(R$^8$)R$^9$, —N(R$^8$)R$^9$, —OR$^5$, —N(R$^7$)R$^7$, —N(R$^7$)R$^9$, —N(R$^8$)R$^9$, —N(R$^8$)C(O)R$^7$, —C(O)OR$^8$, —C(O)N(R$^7$)R$^9$, —C(O)N(R$^8$)R$^9$, or a heterocyclyl optionally substituted by one or more substituents selected from the group consisting of —C(NH)N(R$^8$)R$^9$, —C(NH)N(H)OR$^8$, —C(NH)N(H)C(O)R$^8$, —C(NH)N(H)C(O)OR$^8$, —C(O)OR$^8$, —C(O)N(R$^8$)R$^9$, —R$^{10}$—C(O)OR$^8$, —R$^{10}$—C(O)N(R$^8$)R$^9$ and —SO$_3$H; $R^3$ is hydrogen or alkyl optionally substituted by one or more substituents selected from the group consisting of halo, alkenyl, hydroxy, alkoxy, aryl (optionally substituted by alkyl, hydroxy, halo, —N(R$^8$)R$^9$, —C(O)OR$^8$, —C(O)N(R$^8$)R$^9$), aryloxy (optionally substituted by alkyl, hydroxy, halo, —N(R$^8$)R$^9$, —C(O)OR$^8$, —C(O)N(R$^8$)R$^9$), aralkoxy (optionally substituted by alkyl, hydroxy, halo, —N(R$^8$)R$^9$, —C(O)OR$^8$, —C(O)N(R$^8$)R$^9$), haloalkenyl, cycloalkyl, imidazolyl, indolyl, adamantyl (optionally substituted by halo, alkyl, —N(R$^8$)R$^9$, —C(O)OR$^8$ or —C(O)N(R$^8$)R$^9$), —C(O)OR$^8$, —N(R$^8$)R$^9$, —C(O)N(R$^8$)R$^9$, —C(O)(CH$_2$)$_m$OR$^8$ (where m is 1 to 4), —N(R$^8$)C(O)R$^8$, —N(R$^8$)C(O)N(R$^8$)R$^9$, —N(R$^8$)C(NH)N(R$^8$)R$^9$, —OPO$_3$H$_2$ and —SR$^8$; $R^7$, $R^8$, $R^9$ and $R^{10}$ are as defined above in the Summary of the Invention; X is halo; and W is a protecting group for nitrogen, such as tert-butoxycarbonyl:

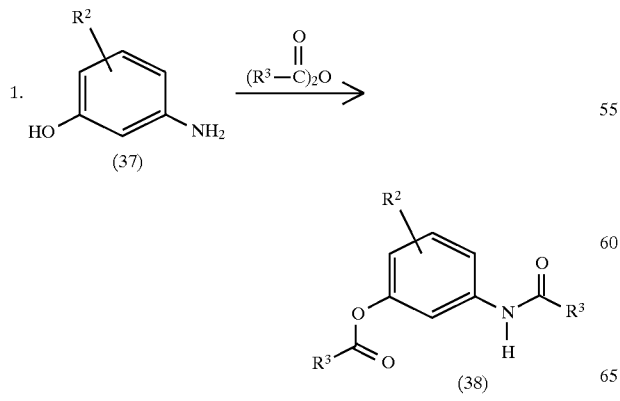

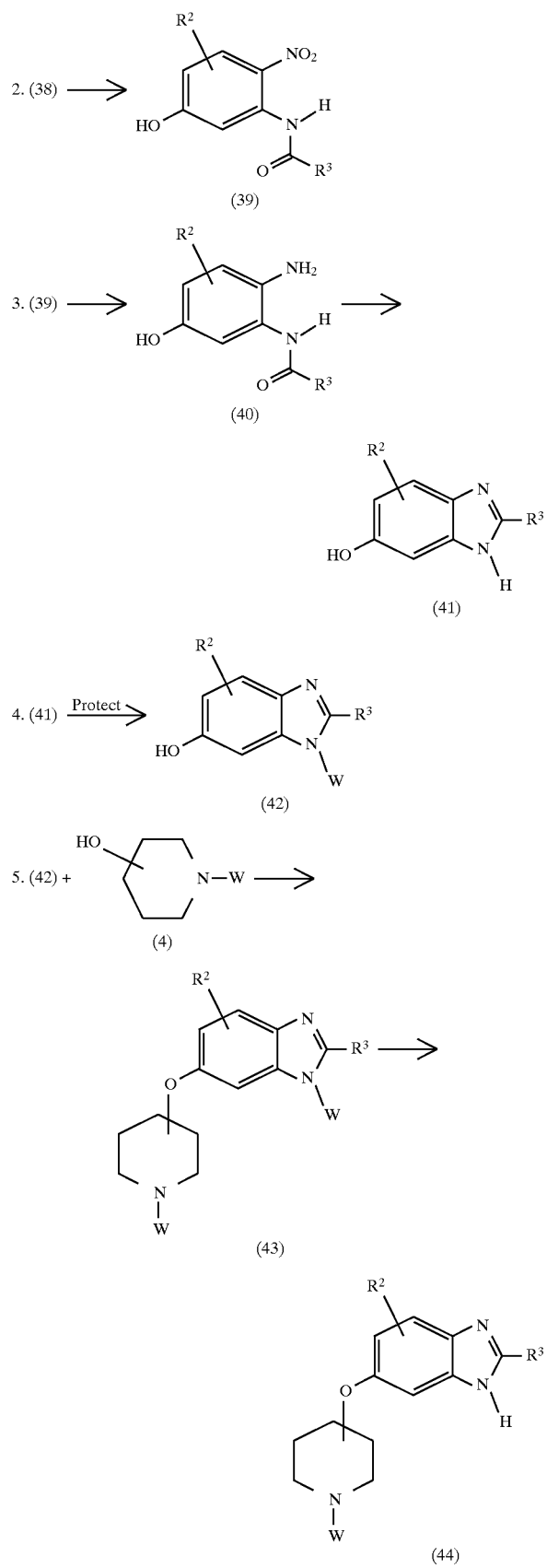

-continued
Reaction Scheme 6

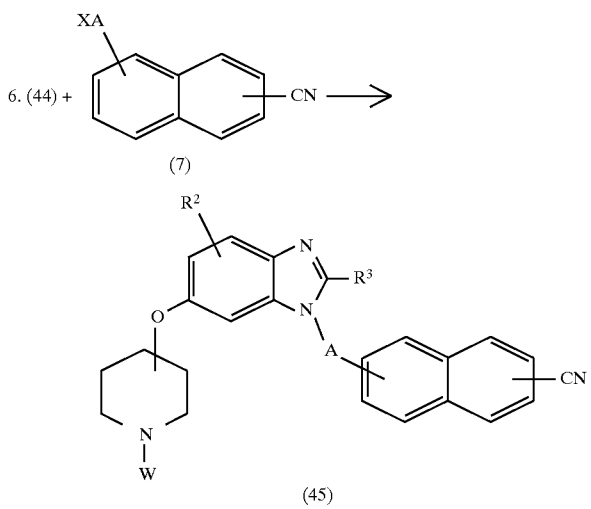

Compounds of formulae (37), (4) and (7) are commercially available, for example, from Aldrich Co., or may be prepared according to methods known to those skilled in the art. Compounds of formula $(R^3—C(O))_2O$ are commercially available, for example, from Aldrich Co., or may be prepared according to methods known to those skilled in the art.

In general, compounds of formula (45) are prepared by first dissolving a compound of formula (37) in an aprotic basic solvent, such as pyridine. The appropriate anhydride is added to the solution at ambient temperature. The resulting reaction mixture is stirred for 1 to 48 hours, preferably, for 12 hours, at ambient temperature. Removal of the solvent affords the compound of formula (38).

The compound of formula (38) is then dissolved in protic acidic solvent, such as trifluoroacetic acid. Concentrated nitric acid is added to the solution at ambient temperature. The resulting mixture is stirred at ambient temperature for 30 minutes to 12 hours, preferably for 2 hours. Isolation through recrystallization gives the compound of formula (39) and its nitro regioisomer.

The compound of formula (39) is then dissolved in a protic solvent, preferably, methanol, and treated with a reducing agent under standard conditions, such as palladium on carbon in the presence of hydrogen under pressure at ambient temperature. The resulting mixture is filtered and the filtrate is concentrated to give the compound of formula (40). The compound of (40) is refluxed for 1 to 3 hours, preferably for 2 hours, in a mild organic acid, such as acetic acid, which corresponds to the anhydride used in Step 1. The acidic solvent is removed and the compound of formula (41) is isolated from the reaction mixture through extraction, drying and concentration.

The compound of formula (41) is then protected in a manner similar to that described above for the compound of formula (2) to produce the compound of formula (42), which is further treated in a manner similar to that described above for the compound of formula (3) to produce compounds of formula (45) and compounds of the invention.

G. Preparation of Compounds of Formulae (Ic) and (Id)

Compounds of formulae (Ic) and (Id) are compounds of the invention and are prepared as shown below in Reaction Scheme 7 wherein A is a straight or branched chain alkylene; $R^2$ is nitro, alkyl (optionally substituted by halo, aryl, —C(O)OR$^8$, —C(O)N(R$^8$)R$^9$, —N(R$^8$)R$^9$), —OR$^5$, —N(R$^7$)R$^7$, —N(R$^7$)R$^9$, —N(R$^8$)R$^9$, —N(R$^8$)C(O)R$^7$, —C(O)OR$^8$, —C(O)N(R$^7$)R$^9$, —C(O)N(R$^8$)R$^9$, or a heterocyclyl optionally substituted by one or more substituents selected from the group consisting of —C(NH)N(R$^8$)R$^9$, —C(NH)N(H)OR$^8$, —C(NH)N(H)C(O)R$^8$, —C(NH)N(H)C(O)OR$^8$, —C(O)OR$^8$, —C(O)N(R$^8$)R$^9$, —R$^{10}$—C(O)OR$^8$, —R$^{10}$—C(O)N(R$^8$)R$^9$ and —SO$_3$H; $R^3$ is hydrogen or alkyl optionally substituted by one or more substituents selected from the group consisting of halo, alkenyl, hydroxy, alkoxy, aryl (optionally substituted by alkyl, hydroxy, halo, —N(R$^8$)R$^9$, —C(O)OR$^8$, —C(O)N(R$^8$)R$^9$), aryloxy (optionally substituted by alkyl, hydroxy, halo, —N(R$^8$)R$^9$, —C(O)OR$^8$, —C(O)N(R$^8$)R$^9$), aralkoxy (optionally substituted by alkyl, hydroxy, halo, —N(R$^8$)R$^9$, —C(O)OR$^8$, —C(O)N(R$^8$)R$^9$), haloalkenyl, cycloalkyl, imidazolyl, indolyl, adamantyl (optionally substituted by halo, alkyl, —N(R$^8$)R$^9$, —C(O)OR$^8$ or —C(O)N(R$^8$)R$^9$), —C(O)OR$^8$, —N(R$^8$)R$^9$, —C(O)N(R$^8$)R$^9$, —C(O)(CH$_2$)$_m$OR$^8$ (where m is 1 to 4), —N(R$^8$)C(O)R$^8$, —N(R$^8$)C(O)N(R$^8$)R$^9$, —N(R$^8$)C(NH)N(R$^8$)R$^9$, —OPO$_3$H$_2$ and —SR$^8$; $R^7$, $R^8$, $R^9$ and $R^{10}$ are as defined above in the Summary of the Invention; X is halo; and W is a protecting group for nitrogen, such as tert-butoxycarbonyl:

Reaction Scheme 7

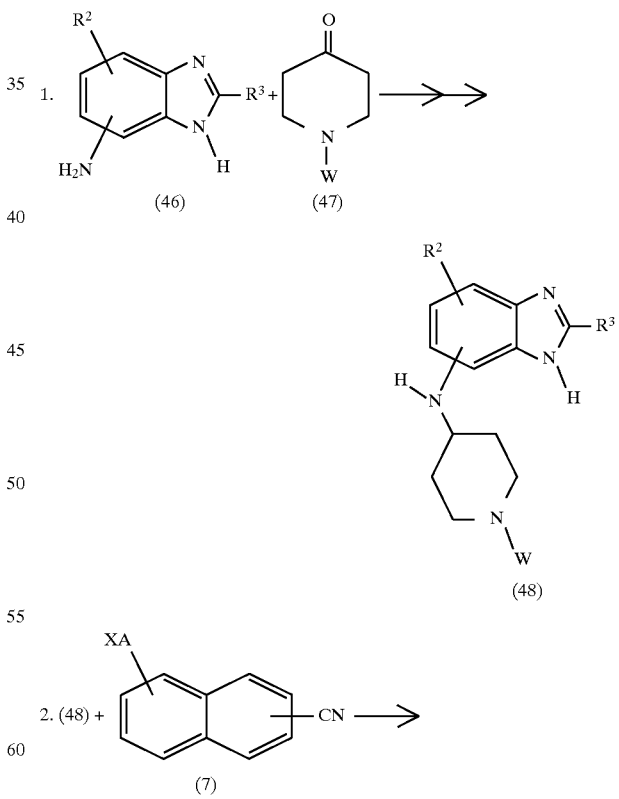

-continued
Reaction Scheme 7

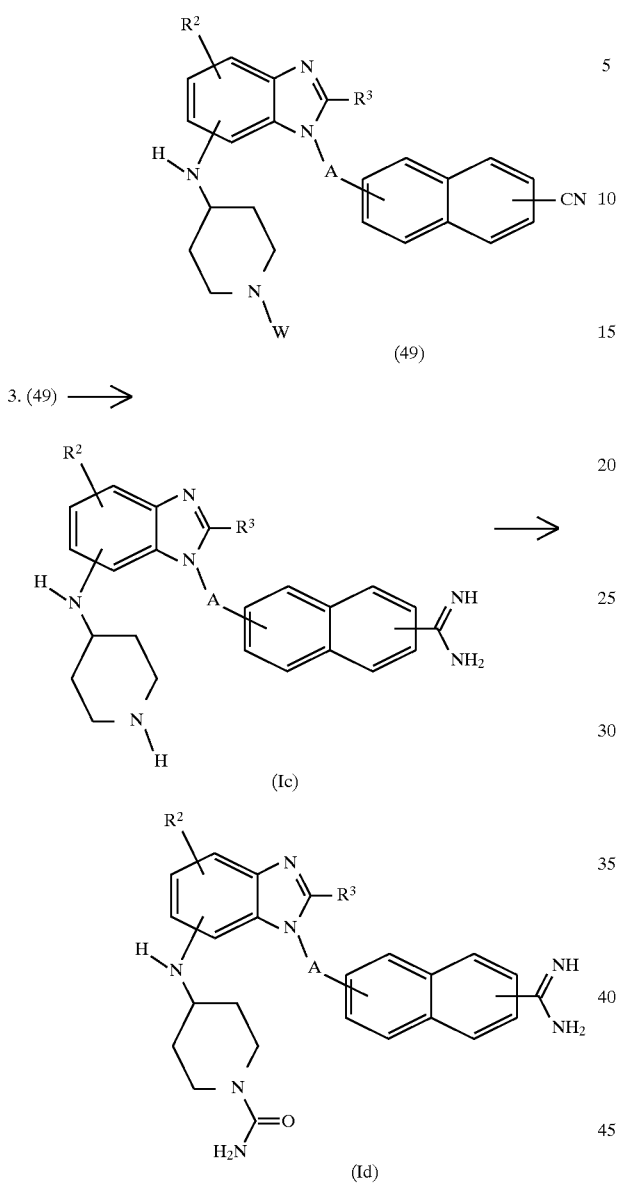

compound of formula (8) to produce the compound of formula (Ic), which is then treated in a manner similar to that described above for the compound of formula (Ia) to produce the compound of formula (Id).

H. Preparation of Compounds of Formula (55)

Compounds of formula (55) are intermediates in the preparation of compounds of the invention and are prepared as shown below in Reaction Scheme 8 wherein $R^3$ is hydrogen or alkyl optionally substituted by one or more substituents selected from the group consisting of halo, alkenyl, hydroxy, alkoxy, aryl (optionally substituted by alkyl, hydroxy, halo, —N($R^8$)$R^9$, —C(O)O$R^8$, —C(O)N($R^8$)$R^9$), aryloxy (optionally substituted by alkyl, hydroxy, halo, —N($R^8$)$R^9$, —C(O)O$R^8$, —C(O)N($R^8$)$R^9$), aralkoxy (optionally substituted by alkyl, hydroxy, halo, —N($R^8$)$R^9$, —C(O)O$R^8$, —C(O)N($R^8$)$R^9$), haloalkenyl, cycloalkyl, imidazolyl, indolyl, adamantyl (optionally substituted by halo, alkyl, —N($R^8$)$R^9$, —C(O)O$R^8$ or —C(O)N($R^8$)$R^9$), —C(O)O$R^8$, —N($R^8$)$R^9$, —C(O)N($R^8$)$R^9$, —C(O)(CH$_2$)$_m$O$R^8$ (where m is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —S$R^8$; $R^6$ is hydrogen, alkyl, —$R^{10}$—C(O)O$R^8$, —$R^{10}$—C(O)N($R^8$)$R^9$, —C(O)$R^7$, or aralkyl (optionally substituted by alkyl, halo, —N($R^8$)$R^9$, —C(O)O$R^8$, or —C(O)N($R^8$)$R^9$); $R^7$, $R^8$, $R^9$ and $R^{10}$ are as defined above in the Summary of the Invention; X is halo; and $W^1$ is a protecting group for nitrogen, such as tert butoxycarbonyl and $W^2$ is a different protecting group for nitrogen, such as tosyl:

Reaction Scheme 8

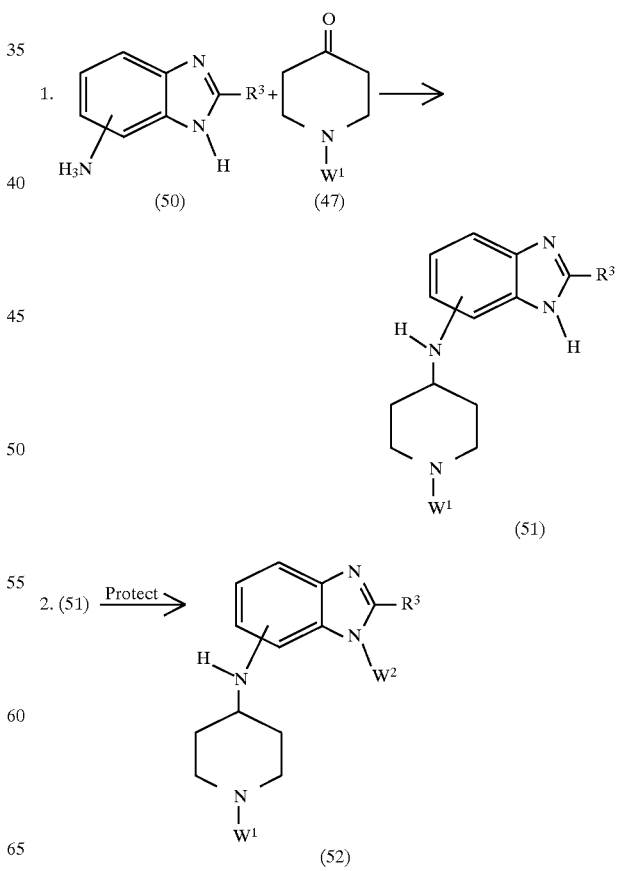

Compounds of formula (46) are prepared according to methods described below in the Preparations. Compounds of formula (47) and (7) are commercially available, for example, from Aldrich Co., or may be prepared according to methods known to those skilled in the art.

In general, the compounds of formulae (Ic) and (Id) are prepared by first dissolving a compound of formula (46) in a protic acidic solvent, such as a mixture of methanol and acetic acid. An excessive molar amount of a compound of formula (47) is then added to the solution at ambient temperature in the presence of a reducing agent, such as NaCNBH$_4$. The reaction mixture is stirred at ambient temperature for 30 minutes to 3 hours, preferably, for 1 hour, and the solvent removed. Conventional isolation techniques, such as aqueous extraction, concentration and column chromatography provides the compound of formula (48).

The compound of formula (48) is then treated in a manner similar to that described above for the compound of formula (6) to produce the compound of formula (49), which is then treated in a manner similar to that described above for the

-continued
Reaction Scheme 8

3. (52) + R⁶—X ⟶
   (53)

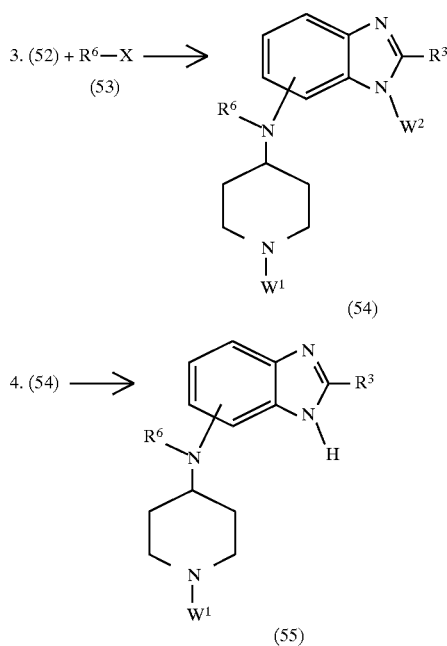

Compounds of formula (50) are prepared according to methods disclosed herein Compounds of formula (47) and R⁶X are commercially available or may be prepared according to methods known to those of ordinary skill in the art.

In general, the compounds of formula (55) are produced by first treating a compound of formula (50) with a compound of formula (47) in a manner similar to that described above for the compound of formula (46) to produce a compound of formula (51). The compound of formula (51) is then dissolved in an aprotic solvent, preferably, DMF, at about 0° C. A strong base, such as sodium hydride, is added to the solution in an excessive molar amount. The solution is stirred for about 30 minutes. A nitrogen-protecting producing group, such as tosyl chloride, is added to the reaction mixture, and the resulting mixture is stirred for 30 minutes to 3 hours, preferably, for 1 hour, at about 0° C. Conventional isolation techniques, such as extraction and concentration yields the compound of formula (52).

The compound of formula (52) is then dissolved in an aprotic solvent, such as DMF, in the presence of a mild base, such as potassium carbonate, and the compound of formula (53), such as methyl iodide. The resulting reaction mixture is stirred for 10 to 24 hours, preferably, for 12 hours, at ambient temperature. Conventional isolation techniques, such as extraction by organic solvent and concentration, yields the compound of formula (54).

When the compound of formula (53) is other than a methyl halide or ethyl bromo acetate and contains an alkylene group, an allyl halide is used to produce the compound of formula (54) and then the compound is reduced to produce the corresponding alkylene-containing R⁶ group.

The compound of formula (54) is then de-protected by dissolving it in a protic solvent, such as methanol, in the presence of a mild nucleophilic agent, such as an alkoxide or a mineral hydroxide, for example, sodium hydroxide. The reaction mixture is stirred for 1 to 3 hours, preferably for 1 hour, at ambient temperature. Conventional isolation techniques, such as evaporation and column chromatography yields the compound of formula (55).

The compound of formula (55) is then further treated in a manner similar to that described above for compounds of formula (6) to produce compounds of the invention.

I. Preparation of Compounds of Formulae (60) and (62)

Compounds of formulae (60) and (62) are intermediates in the preparation of compounds of the invention and are prepared as shown below in Reaction Scheme 9 wherein A is a straight or branched chain alkylene; $R^3$ is hydrogen or alkyl optionally substituted by one or more substituents selected from the group consisting of halo, alkenyl, hydroxy, alkoxy, aryl (optionally substituted by alkyl, hydroxy, halo, —N($R^8$)$R^9$, —C(O)O$R^8$, —C(O)N($R^8$)$R^9$), aryloxy (optionally substituted by alkyl, hydroxy, halo, —N($R^8$)$R^9$, —C(O)O$R^8$, —C(O)N($R^8$)$R^9$), aralkoxy (optionally substituted by alkyl, hydroxy, halo, —N($R^8$)$R^9$, —C(O)O$R^8$, —C(O)N($R^8$)$R^9$), haloalkenyl, cycloalkyl, imidazolyl, indolyl, adamantyl (optionally substituted by halo, alkyl, —N($R^8$)$R^9$, —C(O)O$R^8$ or —C(O)N($R^8$)$R^9$), —C(O)O$R^8$, —N($R^8$)$R^9$, —C(O)N($R^8$)$R^9$, —C(O)(CH$_2$)$_m$O$R^8$ (where m is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —S$R^8$; $R^6$ is hydrogen, alkyl, —$R^{10}$—C(O)O$R^8$, —$R^{10}$—C(O)N($R^8$)$R^9$, —C(O)$R^7$, or aralkyl (optionally substituted by alkyl, halo, —N($R^8$)$R^9$, —C(O)O$R^8$, or —C(O)N($R^8$)$R^9$); $R^7$ is a branched or straight chain alkylene substituted by one or more substituents selected from the group consisting of halo, hydroxy, alkoxy, aryl (optionally substituted by alkyl, hydroxy, halo, —N($R^8$)$R^9$, —C(O)O$R^8$), aryloxy, aralkoxy, alkenyl, haloalkenyl, cycloalkyl, imidazolyl, indolyl, adamantyl (optionally substituted by halo, alkyl, hydroxy, —C(O)O$R^8$ or —N($R^8$)$R^9$), —C(O)O$R^8$, —N($R^8$)$R^9$, —C(O)N($R^8$)$R^9$, —C(O)(CH$_2$)$_q$O$R^8$ (where q is 1 to 4), —N($R^8$)C(O)$R^8$, —N($R^8$)C(O)N($R^8$)$R^9$, —N($R^8$)C(NH)N($R^8$)$R^9$, —OPO$_3$H$_2$ and —S$R^8$; $R^8$, $R^9$ and $R^{10}$ are as defined above in the Summary of the Invention; X is halo; and W is a protecting group for nitrogen, such as tert-butoxycarbonyl:

Reaction Scheme 9

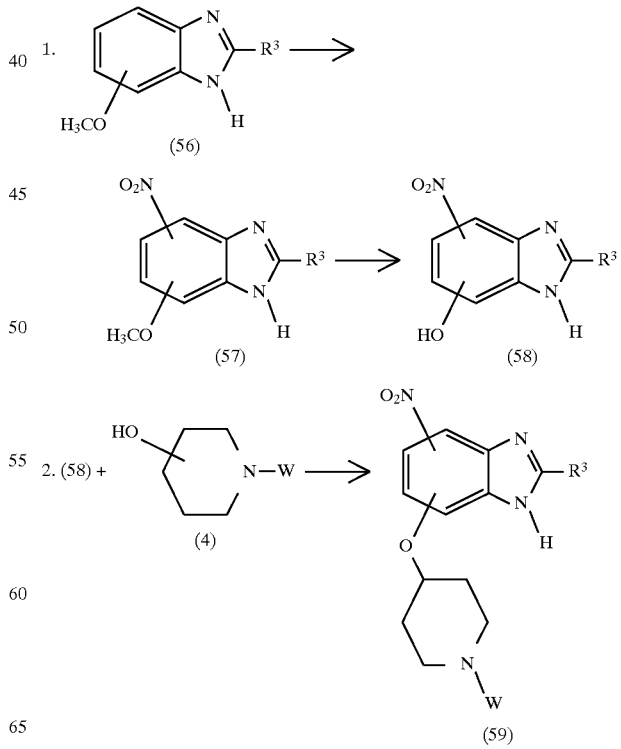

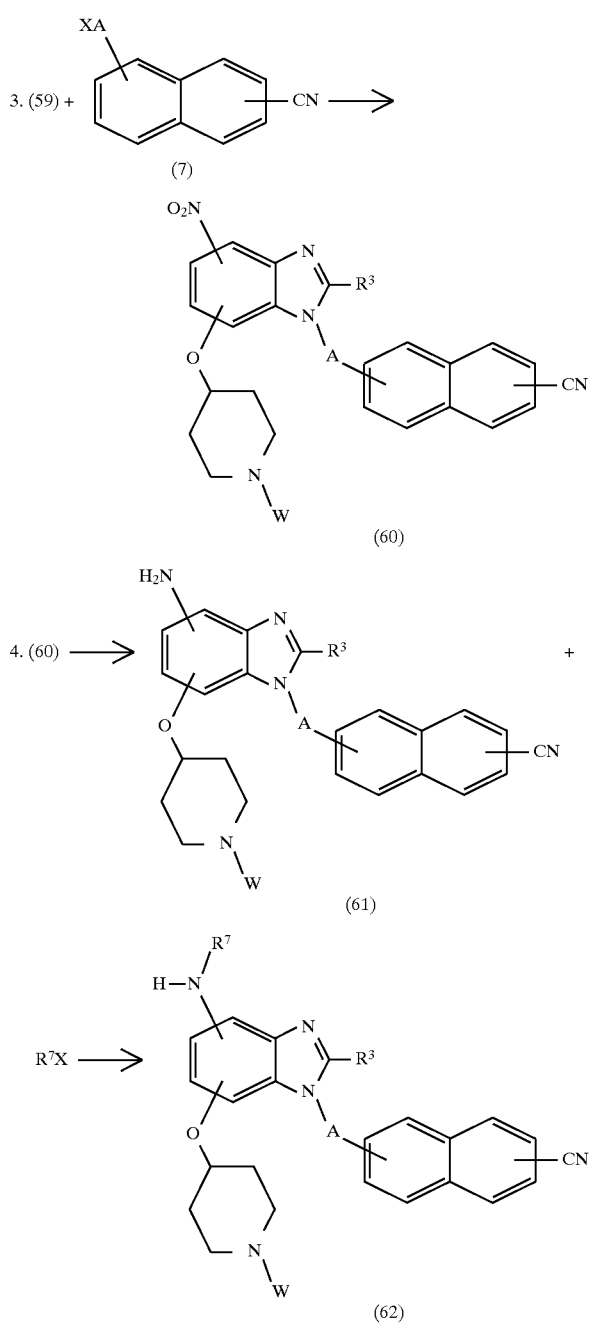

The compound of formula (57) is then de-methylated in a manner similar to that described above for compound of formula (11) to produce the compound of formula (58), which is then treated in a manner similar to that described above for the compound of formula (3) to produce the compound of formula (59).

The compound of formula (59) is then treated in a manner similar to that described above for the compound of formula (7) to produce the compound of formula (60), which is then dissolved in a basic aprotic solvent, such as pyridine. A mild reducing agent, such as tin (III) chloride dihydrate, is then added to the solution. The resulting slurry is then heated to 50° to 60° C., preferably to 50° C., for 10 to 16 hours, preferably for 14 hours. The solvent is removed and the resulting residue dissolved in an organic solvent. Conventional isolation techniques, such a filtration, concentration and chromatography, yields the compound of formula (61).

The compound of formula (61) is then dissolved in an aprotic solvent, preferably, DMF. An excessive molar amount of a compound of formula $R^7X$ is then added to the solution in the presence of a mild base, such as potassium bicarbonate. The reaction mixture is stirred for 24 to 48 hours, preferably for 48 hours, at 20° C. to 55° C., preferably at 20° C. Conventional isolation techniques, such as extraction and chromatography, yields the compound of formula (62).

The compound of formula (62) is then treated in a manner similar to that described above for the compound of formula (8) to produce compounds of the invention.

In addition, the compound of formula (60) may be treated in a manner similar to that described above for the compound of formula (8) to produce compounds of the invention.

In addition, all compounds of the invention that exist in free base form or free acid form may be converted to their pharmaceutically acceptable salts by treatment with the appropriate inorganic or organic acid, or by the appropriate inorganic or organic base. Salts of the compounds of the invention can also be converted to the free base form or to the free acid form or to another salt.

The following specific preparations and examples are provided as a guide to assist in the practice of the invention, and are not intended as a limitation on the scope of the invention.

PREPARATION 1

Compounds of formula (2)

To a solution of 4-amino-3-nitrophenol (25.0 g, 162 mmol) and methanol (300 mL) was added 10% Pd/C (300 mg). The reaction was placed under hydrogen and shaken for 12 hours. Afterward, 4N HCl (50 mL) was added. The mixture was then filtered through celite. The filtrate was concentrated to give 3,4-diaminophenol.

PREPARATION 2

Compounds of formula (3)

A. A solution of 3,4-diaminophenol (5.20 g, 42.0 mmol), isobutyric acid (5.80 mL, 63.0 mmol) and 4N HCl (50 mL) was refluxed for 16 hours. After cooling to ambient temperature, the reaction was neutralized ($KHCO_3$). Filtration afforded a dark solid. The solid was dissolved in THF (100 mL) and $H_2O$ (20 mL). Di-tert-butyldicarbonate (4.09 g, 18.7 mmol) was added to the solution. After stirring for 12 hours, the reaction mixture was poured into $H_2O$ (50 mL). The resulting mixture was extracted with ethyl acetate Compounds of formulae (56), (4), (7) and $R^7X$ are commercially available, for example, from Aldrich Co., or may be prepared according to methods known to those skilled in the art.

In general, the compounds of formula (62) are prepared by first dissolving a compound of formula (56) in a protic solvent, preferably, trifluoroacetic acid, in the presence of nitric acid at ambient temperature. The resulting reaction mixture is stirred for 6 to 16 hours, preferably, for 12 hours. The solvents are removed by evaporation and the residue neutralized to about pH 7 with a mild base, such as sodium bicarbonate. Conventional isolation techniques, such as extraction, concentration and column chromatography yields the compound of formula (57).

(2×150 mL). The organic layers were washed with brine (10 mL), dried (Na$_2$SO$_4$) and concentrated. The resulting oil was chromatographed on SiO$_2$ (50 g) with hexane/ethyl acetate (1:1) to afford 1-tert-butoxycarbonyl-6-hydroxy-2-isopropylbenzimidazole.

B. In a similar manner, the following compounds of formula (3) were made:
1-tert-butoxycarbonyl-6-hydroxybenzimidazole;
1-tert-butoxycarbonyl-6-hydroxy-2-methylbenzimidazole;
1-tert-butoxycarbonyl-6-hydroxy-2-trifluoromethylbenzimidazole;
1-tert-butoxycarbonyl-6-hydroxy-2-ethylbenzimidazole;
1-tert-butoxycarbonyl-6-hydroxy-2-propylbenzimidazole;
1-tert-butoxycarbonyl-6-hydroxy-2-butylbenzimidazole;
1-tert-butoxycarbonyl-6-hydroxy-2-isobutylbenzimidazole; and
1-tert-butoxycarbonyl-6-hydroxy-2-tert-butylbenzimidazole.

C. Alternatively, succinic anhydride (11.2 g, 113 mmol, 2 eq) and 3,4-diaminophenol (7 g, 56 mmoL, 1 eq) were dissolved in 150 mL dry DMF and the mixture was heated to 100° C. for 3 hours. The DMF was removed in vacuo, and the residue was dissolved in 350 mL 4N HCl and refluxed for 14 hours. The reaction was cooled, the water was removed in vacuo and the residue was dissolved in 200 mL methanol and to this was added 20 mL concentrated sulfuric acid. This mixture was refluxed overnight. The methanol was stripped off and the residue neutralized to pH 7 with saturated aqueous sodium bicarbonate. The water was removed in vacuo and the residue was triturated with THF (4×100 mL). The combined THF fractions were concentrated to about 100 mL volume and di-tert-butyldicarbonate (12 g, 56 mmol, 1 eq.) was added. The mixture was stirred overnight at ambient temperature and then concentrated. The crude oil was chromatographed (1:1 ethyl acetate/hexanes) to afford 1-tert-butoxycarbonyl-6-hydroxy-2-(methoxycarbonylethyl)benzimidazole as a colorless solid, 5 g (42%, yield).

PREPARATION 3

Compounds of formula (5)

A. DEAD (0.60 mL, 3.80 mmol) was added to a solution of 1-tert-butoxycarbonyl-6-hydroxy-2-isopropylbenzimidazole (690 mg, 2.30 mmol), 1-tert-butoxycarbonyl-4-hydroxypiperidine (925 mg, 4.60 mmol), triphenylphosphine (904 mg, 3.45 mmol) and THF (5 mL) at 25° C. After stirring for 12 hours, the solvent was removed in vacuo. Chromatography (SiO$_2$, 100 g) of the resulting oil with hexane/ethyl acetate (1:1) afforded 1-tert-butoxycarbonyl-6-(N-(tert-butoxycarbonyl)piperidin-4-yloxy)-2-isopropylbenzimidazole.

B. In a similar manner, the following compounds of formula (5) were made:
1-tert-butoxycarbonyl-6-(N-(tert-butoxycarbonyl)piperidin-4-yloxy)benzimidazole;
1-tert-butoxycarbonyl-6-(N -(tert-butoxycarbonyl)piperidin-4-yloxy)-2-methylbenzimidazole;
1-tert-butoxycarbonyl-6-(N-(tert-butoxycarbonyl)piperidin-4-yloxy)-2-trifluoromethyl-benzimidazole;
1-tert-butoxycarbonyl-6-(N-(tert-butoxycarbonyl)piperidin-4-yloxy)-2-ethylbenzimidazole;
1-tert-butoxycarbonyl-6-(N-(tert-butoxycarbonyl)piperidin-4-yloxy)-2-propylbenzimidazole;
1-tert-butoxycarbonyl-6-(N-(tert-butoxycarbonyl)piperidin-4-yloxy)-2-butylbenzimidazole;
1-tert-butoxycarbonyl-6-(N-(tert-butoxycarbonyl)piperidin-4-yloxy)-2-isobutylbenzimidazole;
1-tert-butoxycarbonyl-6-(N-(tert-butoxycarbonyl)piperidin-4-yloxy)-2-tert-butylbenzimidazole; and
1-tert-butoxycarbonyl-6-(N-(tert-butoxycarbonyl)piperidin-4-yloxy)-2-isopropyl-4-methoxybenzimidazole.

PREPARATION 4

Compounds of formula (8)

A. A solution of 1-tert-butoxycarbonyl-6-(N-(tert-butoxycarbonyl)piperidin-4-yloxy)-2-isopropylbenzimidazole (425 mg, 0.92 mmol) and methanol (10 mL) was cooled in a dry ice/acetone bath and NH$_3$ (g) was bubbled in. The reaction flask was sealed and heated to 50° C. for 12 hours. The solvent was removed in vacuo. The resulting oil was chromatographed on SiO$_2$ (50 g) using ethyl acetate to afford a clear oil (a compound of formula (6)). To a solution of the oil and DMF (15 mL) was added NaH (28.0 mg, 0.70 mmol). The solution was stirred for 1 hour before 7-bromomethyl-2-naphthonitrile (178 mg, 0.72 mmol) was added. After stirring for 20 hours, the reaction was poured into H$_2$O (50 mL). The aqueous layer was extracted with ethyl acetate (2×60 mL). The organic layers were washed with brine (50 mL), dried (Na$_2$SO$_4$) and concentrated. The resulting oil was chromatographed on SiO$_2$ (20 g) with ethyl acetate to afford 6-(N-(tert-butoxycarbonyl)piperidin-4-yloxy)-2-isopropyl-1-(4-cyanonaphth-1-yl)methylbenzimidazole and 5-(N-(tert-butoxycarbonyl)piperidin-4-yloxy)-2-isopropyl-1-(4-cyanonaphth-1-yl)methylbenzimidazole as a 1:1 mixture of compounds.

B. In a similar manner, the following compounds of formula (8) were made:
6-(N-(tert-butoxycarbonyl)piperidin-4-yloxy)-1-(4-cyanonaphth-1-yl)benzimidazole and 5-(N-(tert-butoxycarbonyl)piperidin-4-yloxy)-1-(4-cyanonaphth-1-yl)benzimidazole;
6-(N-(tert-butoxycarbonyl)piperidin-4-yloxy)-1-(4-cyanonaphth-1-yl)-2-methylbenzimidazole and 5-(N-(tert-butoxycarbonyl)piperidin-4-yloxy)-1-(4-cyanonaphth-1-yl)-2-methylbenzimidazole;
6-(N-(tert-butoxycarbonyl)piperidin-4-yloxy)-1-(4-cyanonaphth-1-yl)-2-trifluoromethyl-benzimidazole and 5-(N-(tert-butoxycarbonyl)piperidin-4-yloxy)-1-(4-cyanonaphth-1-yl)-2-trifluoromethylbenzimidazole;
6-(N-(tert-butoxycarbonyl)piperidin-4-yloxy)-1-(4-cyanonaphth-1-yl)-2-ethylbenzimidazole and 5-(N-(tert-butoxycarbonyl)piperidin-4-yloxy)-1-(4-cyanonaphth-1-yl)-2-ethylbenzimidazole;
6-(N-(tert-butoxycarbonyl)piperidin-4-yloxy)-1-(4-cyanonaphth-1-yl)-2-propylbenzimidazole and 5-(N-(tert-butoxycarbonyl)piperidin-4-yloxy)-1-(4-cyanonaphth-1-yl)-2-propylbenzimidazole;
6-(N-(tert-butoxycarbonyl)piperidin-4-yloxy)-1-(4-cyanonaphth-1-yl)-2-butylbenzimidazole and 5-(N-(tert-butoxycarbonyl)piperidin-4-yloxy)-1-(4-cyanonaphth-1-yl)-2-butylbenzimidazole;
6-(N-(tert-butoxycarbonyl)piperidin-4-yloxy)-1-(4-cyanonaphth-1-yl)-2-isobutylbenzimidazole and 5-(N-(tert-butoxycarbonyl)piperidin-4-yloxy)-1-(4-cyanonaphth-1-yl)-2-isobutylbenzimidazole;
6-(N-(tert-butoxycarbonyl)piperidin-4-yloxy)-1-(4-cyanonaphth-1-yl)-2-tert-butylbenzimidazole and 5-(N-(tert-butoxycarbonyl)piperidin-4-yloxy)-1-(4-cyanonaphth-1-yl)-2-tert-butylbenzimidazole;
6-(N-(tert-butoxycarbonyl)piperidin-4-yloxy)-1-(4-cyanonaphth-1-yl)-2-isopropyl-4-methoxybenzimidazole and 5-(N-(tert-butoxycarbonyl)piperidin-4-yloxy)-1-(4- cyanonaphth-1-yl)-2-isopropyl-4-methoxybenzimidazole;

6-(N-(tert-butoxycarbonyl)piperidin-4-yl)amino-1-(4-cyanonaphth-1-yl)benzimidazole;

6-(N-(tert-butoxycarbonyl)piperidin-4-yl)((methoxycarbonyl)methyl)amino-1-(4-cyanonaphth-1-yl)-2-methylbenzimidazole;

6-(N-(tert-butoxycarbonyl)piperidin-4-yl)(3-(methoxycarbonyl)prop-1-yl)amino-1-(4-cyanonaphth-1-yl)-2-methylbenzimidazole;

6-(N-(tert-butoxycarbonyl)piperidin-4-yl)(2-(methoxycarbonyl)prop-1-yl)amino-1-(4-cyanonaphth-1-yl)-2-methylbenzimidazole;

5-(N-(tert-butoxycarbonyl)piperidin-4-yl)(2-(methoxycarbonyl)prop-1-yl)amino-1-(4-cyanonaphth-1-yl)-2-methylbenzimidazole;

6-(N-(tert-butoxycarbonyl)piperidin-4-yl)amino-2-methyl-5-nitro-1-(4-cyanonaphth-1-yl)benzimidazole; and 6-(N-(tert-butoxycarbonyl)piperidin-4-yl)amino-2-isopropyl-5-nitro-1-(4-cyanonaphth-1-yl)benzimidazole.

PREPARATION 5

Compounds of formula (10)

To a solution of 1,3,5-trifluoro-2-nitrobenzene (25.0 g, 141 mmol) and THF (30 mL) cooled in a dry ice/acetone bath was bubbled in $NH_3$ (g). After saturation, the reaction tube was sealed and warmed to ambient temperature. After stirring for 12 h, the reaction mixture was filtered and the filtrate concentrated to afford a yellow oil. The yellow oil was dissolved in methanol (150 mL). Over 1 hour, sodium methoxide (27.0 g, 500 mmol) was added. The reaction was stirred for 3 hours, then $H_2O$ (500 mL) was added. The mixture washed with ethyl acetate (3×700 mL). The organic layers were washed with brine (50 mL), dried ($Na_2SO_2$) and concentrated to afford 3,5-dimethoxy-2-nitroaniline as a red solid.

PREPARATION 6

Compounds of formula (11)

A. To a solution of 3,5-dimethoxy-2-nitroaniline (55.0 g, 321 mmol) and pyridine (400 mL) was added isobutyryl chloride (41.0 mL, 391 mmol). After stirring for 16 hours, the reaction mixture was concentrated in vacuo. The resulting oil was partitioned between $H_2O$ (200 mL) and ethyl acetate (200 mL). The aqueous layer was extracted with more ethyl acetate (2×200 mL). The organic layers were washed with brine (50 mL), dried ($MgSO_4$) and concentrated. The solid was recrystallized from hexane/ethyl acetate at 5° C. to afford yellow crystals. To a slurry of the yellow crystals, 4N HCl (200 mL) and ethanol (250 mL) was added 10% Pd/C (1.30 g). The slurry was placed under 50 psi of $H_2$ (g) and shaken for 4 hours. The mixture was then filtered and concentration of the filtrate afforded a white solid. The white solid was dissolved in 2N HCl (200 mL) and refluxed for 4 hours. The reaction mixture was concentrated. The resulting solid was dissolved in 48% HBr (100 mL) and $H_2O$ (100 mL) and refluxed for 15 hours. The reaction was then cooled to ambient temperature and concentrated. The solids were dissolved in $H_2O$ (200 mL) and neutralized ($KHCO_3$). The aqueous layer was then extracted with n-butanol (3×500 mL). The organic layer was washed with brine (50 mL), treated with activated charcoal and concentrated to afford 4,6-dihydroxy-2-isopropylbenzimidazole, a compound of formula (11).

B. Alternatively, a solution of 4,6-dimethoxy-2-isopropylbenzimidazole (12.70 g, 57.66 mmol) and 48% HBr (100 mL) was refluxed for 3 hours, and then the solution was cooled to ambient temperature and concentrated. The resulting solids were dissolved in $H_2O$ (100 mL) and neutralized ($NaHCO_3$). A brown precipitate formed which was isolated by filtration. The precipitate was dissolved in MeOH (100 mL), treated with charcoal and concentrated to afford 6-hydroxy-2-isopropyl-4-methoxybenzimidazole as a brown solid.

PREPARATION 7

Compounds of formula (12) and (13)

To a mixture of 4,6-dihydroxy-2-isopropylbenzimidazole (36.0 g, 113 mmol), imidazole (35.0 g, 514 mmol) and DMF (200 mL) was added tert-butyldimethylsilyl chloride (40.0 g, 265 mmol). The dark mixture was stirred for 10 hours, then it was partitioned between $H_2O$ (500 mL) and ethyl acetate (500 mL). The aqueous layer was extracted with more ethyl acetate (2×500 mL). The combined organic layers were washed with brine (100 mL), dried ($Na_2SO_4$), treated with activated charcoal and concentrated to afford a dark oil, 4,6-di(tetrabutyldimethylsilyl)oxy-2-isopropylbenzimidazole. The oil (12.2 g, 29 mmol) was dissolved in DMF (150 mL) and treated with NaH (1.76 g, 44.0 mmol). After 4 hours, the solution was placed in an ice bath, then methyl bromoacetate (1.50 mL, 15.8 mmol) was added dropwise. The reaction was stirred for 40 minutes, then a second portion of methyl bromoacetate (1.20 mL, 12.6 mmol) was added. After stirring for 20 more minutes, the reaction mixture was added to $H_2O$ (300 mL). The aqueous layer was extracted with ethyl acetate (3×300 mL). The combined organic layers were washed with brine (50 mL), dried ($Na_2SO_4$) and concentrated to afford a oil. Chromatography ($SiO_2$, 500 g) of the oil with hexane/ethyl acetate (1:1) afforded 2-isopropyl-4-(carboxy)methyl-6-(tetrabutyldimethylsilyl)oxybenzimidazole.

PREPARATION 8

Compounds of formula (14a)

A. To a mixture of 2-isopropyl-4-(carboxy)methoxy-6-(tetrabutyldimethylsilyl)oxybenzimidazole (9.00 g, 18.7 mmol) and THF (100 mL) was added di-tert-butyldicarbonate (23.0 g, 105 mmol). The reaction mixture was refluxed for 7 hours. After cooling to ambient temperature, it was concentrated. The resulting oil was purified by chromatography (500 g $SiO_2$) with hexane/ethyl acetate (2:1) to afford a clear oil. A solution (0.01M) of the clear oil in THF (300 mL) was placed in an ice bath. After a few minutes tetrabutyl ammonium fluoride (8.00 mL of a 1.0M solution, 8 mmol) was added. The reaction mixture was stirred for a few minutes, then the reaction mixture was partitioned between $H_2O$ (300 mL) and ether (300 mL). The aqueous layer was extracted with more ether (2×300 mL). The combined organic layers were washed with brine (50 mL), dried ($Na_2SO_4$) and concentrated to afford a yellow oil. Chromatography (10 g $SiO_2$) using ether afforded 1-tert-butoxycarbonyl-2-isopropyl-4-(carboxy)methoxy-6-hydroxybenzimidazole.

B. Alternatively, to a mixture of 6-hydroxy-2-isopropyl-4-methoxybenzimidazole (3.44 g, 18 mmol), THF (50 mL) and $H_2O$ (50 mL) was added di-tert-butyldicarbonate (8.00 g, 37 mmol). The mixture was refluxed for 16 hours. Afterwards, the reaction mixture was extracted with ethyl acetate (3×50 mL). The organic layers were washed with brine, dried ($Na_2SO_4$) and concentrated. Chromatography ($SiO_2$, 100 g) of the resulting oil with hexane/ethyl acetate (1:1) afforded 1-tert-butoxycarbonyl-6-hydroxy-2-isopropyl-4-methoxybenzimidazole.

PREPARATION 9

Compounds of formula (16)

In a 1 L flask, 2,4,6-trifluoro-2-nitrobenzene (8.2 mL, 70 mmoL, 1.1 eq.) was added to 500 mL of dry acetonitrile and the solution chilled to −10° C. Diisopropylethylamine (33 mL, 191 mmol, 3 eq) and ethyl isonipecotate (10 g, 64 mmoL, 1 eq.) were added slowly (approx. 20 min.) as a combined solution via addition funnel, under nitrogen. The reaction turned yellow almost immediately, and it was warmed to 20° C. slowly. After 5 hours at 20° C., thin layer chromatography showed the reaction to be nearly complete (95/5 hexanes/ethyl acetate). The acetonitrile was removed in vacuo and the resulting yellow oil was dissolved in 1 L of ethyl acetate. This solution was washed with water (3×100 mL), brine (1×300 mL), dried over sodium sulfate, and concentrated to give 20 g of a yellow oil. This material was identified as 6-(4-(ethoxycarbonyl)piperidin-1-yl)-2,4-difluoro-1-nitrobenzene by $^1$H NMR.

PREPARATION 10

Compounds of formula (17)

6-(4-(Ethoxycarbonyl)piperidin-1-yl)-2,4-difluoro-1-nitrobenzene (20 g, 64 mmoL, 1 eq) was dissolved in 300 mL of dry acetonitrile and the solution chilled to −10° C. Diisopropylethylamine (33 mL, 191 mmol, 3 eq) and benzyl amine (7 mL, 64 mmol, 1 eq) were added slowly (approx. 20 min.) as a combined solution via addition funnel, under nitrogen. The reaction turned yellow almost immediately, and it was warmed to 20° C. slowly. After 48 hours at 20° C., thin layer chromatography showed the reaction was only about half complete. The reaction was heated to 50° C. for 24 hours, cooled, the acetonitrile was removed in vacuo and the resulting orange oil was dissolved in 1 L of ethyl acetate. This solution washed with water (3×100 mL), brine (1×300 mL), dried over sodium sulfate, and concentrated to give 20 g of an orange oil. Chromatography (95/5 hexanes/ethyl acetate) gave 12 g (48% yield) of 2-N-benzylamino-6-(4-(ethoxycarbonyl)piperidin-1-yl)-4-fluoro-1-nitrobenzene.

PREPARATION 11

Compounds of formula (18)

2-N-Benzylamino-6-(4-(ethoxycarbonyl)piperidin-1-yl)-4-fluoro-1-nitrobenzene (11 g, 27 mmol, 1 eq) was added to 200 mL of dry methanol and to the mixture was added slowly (approx. 20 min.) sodium methoxide (5.0 g) as a solution in 100 mL methanol, under nitrogen. The reaction was heated to reflux for 6 hours, cooled, the methanol was removed in vacuo and the resulting red solid was dissolved in 1 L of ethyl acetate. This solution washed with water (3×100 mL), brine (1×300 mL), dried over sodium sulfate, and concentrated to give a dark red oil. Chromatography (10–50% ethyl acetate in hexanes) gave 4.3 g (38% yield) of 2-N-benzylamino-6-(4-(methoxycarbonyl)piperidin-1-yl)-4-methoxy-1-nitrobenzene.

PREPARATION 12

Compounds of formula (19)

2-N-Benzylamino-6-(4-(methoxycarbonyl)piperidin-1-yl)-4-methoxy-1-nitrobenzene (4.3 g, 10 mmol, 1 eq) was dissolved in 100 mL methanol and to the mixture was added a few grams of 10% Pd/C (wet Degussa type) followed by 50 mL of 4N HCL. The mixture was hydrogenated at 50 psi for 2 hours, the solids filtered out with Celite; and the filtrate concentrated to give a light tan solid. The HCl salt form of the diamine (quant. yield) was identified as 1,2-diamino-6-(4-(methoxycarbonyl)piperidin-1-yl)-4-methoxybenzene by $^1$H NMR.

PREPARATION 13

Compounds of formula (20)

1,2-Diamino-6-(4-(methoxycarbonyl)piperidin-1-yl)-4-methoxybenzene bis-hydrochloride (3.7 g, 10 mmol, 1 eq) was dissolved in 100 mL dry pyridine and to the mixture was added isobutyryl chloride (2.2 mL, 20 mmoL, 2 eq.) at 0° C. The mixture was allowed to slowly warm to 20° C. and stirred overnight. The pyridine was removed in vacuo and the residue was dissolved in 500 mL of ethyl acetate. This solution was washed with water (3×100 mL), brine (1×300 mL), dried over sodium sulfate, and concentrated to give 3.5 g (87% yield) of a dark brown residue. This material was identified as 1,2-di((1-methylethyl)carbonyl)amino-6-(4-(methoxycarbonyl)piperidin-1-yl)-4-methoxybenzene by $^1$H NMR. The residue (3.5 g, 10 mmol, 1 eq) was dissolved in 100 mL 4N HCl and the mixture was refluxed overnight. The HCl was removed in vacuo and the residue was neutralized to pH 7 with saturated aqueous sodium bicarbonate. The water was removed in vacuo and the residue was triturated with THF (4×100 mL). The combined THF fractions were dried over sodium sulfate and concentrated to give 2.5 g (69% yield) of a dark solid. This material was identified as 2-isopropyl-4-(4-(carboxy)piperidin-1-yl)-6-methoxybenzimidazole by $^1$H NMR.

PREPARATION 14

Compounds of formula (21)

4-(4-(Carboxy)piperidin-1-yl)-6-methoxy-2-isopropylbenzimidazole (2.5 g, 7.4 mmol, 1 eq) was dissolved in 60 mL 48% HBr and the mixture was refluxed for 3 hours. The HBr was removed in vacuo and the residue was dissolved in 200 mL methanol and to this was added 20 mL concentrated sulfuric acid. This mixture was refluxed overnight. The methanol was stripped off and the residue neutralized to pH 7 with saturated aqueous sodium bicarbonate. The water was removed in vacuo and the residue was triturated with THF (4×100 mL). The combined THF fractions were dried over sodium sulfate and concentrated to give 2 g of a dark red solid. This material was identified as 4-(4-(methoxycarbonyl)piperidin-1-yl)-6-hydroxy-2-isopropylbenzimidazole by $^1$H NMR (with some methoxy product still remaining). Chromatography (2.5:1 ethyl acetate/hexanes) gave the desired product as a colorless solid, 800 mg (32%, yield).

PREPARATION 15

Compounds of formula (22)

4-(4-(Methoxycarbonyl)piperidin-1-yl)-6-hydroxy-2-isopropylbenzimidazole (800 mg, 2.4 mmol, 1 eq) was dissolved in 20 mL THF and to the solution was added di-tert-butyldicarbonate (520 mg, 2.4 mmoL, 1 eq.) and the resulting mixture was refluxed. Thin layer chromatography indicated that the reaction was sluggish, therefore several 1 eq. aliquots of di-tert-butyldicarbonate were added over a period of 3 days of reflux. The reaction was cooled, the THF removed in vacuo, and the residue chromatographed (4:1 hexanes/ethylacetate) to give 1-tert-butoxycarbonyl-4-(4-(methoxycarbonyl)piperidin-1-yl)-6-hydroxy-2-isopropylbenzimidazole as a colorless solid, 590 mg (59%, yield).

PREPARATION 16

Compounds of formula (25)

2-Methyl-5,6-dihydroxybenzimidazole (100 g) in THF (1 L) was basified to pH 8 with aqueous $NaHCO_3$, and to the resulting solution was then added di-tert-butyldicarbonate (104 g). After stirring for 3 hours, the THF was removed, and the aqueous residue was diluted and extracted with ethyl acetate. The organic layer was dried and concentrated to afford 1-tert-butoxycarbonyl-2-methyl-5,6-dihydroxybenzimidazole as a white solid.

PREPARATION 17

Compounds of formula (26) and (27)

To 1-tert-butoxycarbonyl-2-methyl-5,6-dihydroxybenzimidazole (12 g) in DMF (100 mL) was added imidazole (6.5 g) and tert-butyldimethylsilyl chloride (7.5 g) with vigorous stirring. After stirring for 1 hour, the reaction was worked up between ethyl acetate/water. The organic layer was dried and concentrated to afford a mixture of 1-tert-butoxycarbonyl-2-methyl-5-(tert-butyldimethylsilyl)oxy-6-hydroxybenzimidazole, 1-tert-butoxycarbonyl-2-methyl-6-(tert-butyldimethylsilyl)oxy-5-hydroxybenzimidazole, and 1-tert-butoxycarbonyl-2-methyl-5,6-di((tert-butyldimethylsilyl)oxy)benzimidazole. To the mixture in THF (150 mL) was first added N-tert-butoxycarbonyl-4-hydroxy-piperidine (12 g), $PPh_3$ (15 g), and then DEAD (10 mL) in a dropwise fashion. After stirring at ambient temperature for 1 hour the solvent was removed and the residue was purified and the regioisomers separated by silica gel chromatography (hexane/ethyl acetate, gradient) to afford 1-tert-butoxycarbonyl-2-methyl-5-(tert-butyldimethylsilyl)oxy-6-(N-(tert-butoxycarbonyl)piperidin-4-yloxy)benzimidazole, 1-tert-butoxycarbonyl-2-methyl-6-(tert-butyldimethylsilyl)oxy-5-(N-(tert-butoxycarbonyl)piperidin-4-yloxy)benzimidazole, and 1-tert-butoxycarbonyl-2-methyl-5,6-di((tert-butyldimethylsilyl)oxy)benzimidazole.

PREPARATION 18

Compounds of formula (28) and (29)

To 1-tert-butoxycarbonyl-2-methyl-5-(tert-butyldimethylsilyl)oxy-6-(N-(tert-butoxycarbonyl)piperidin-4-yloxy)benzimidazole (5 g) in methanol (100 mL) was bubbled in ammonia at 0° C. After stirring for 12 hours at ambient temperature in a sealed vessel the reaction mixture was concentrated and dried to afford 2-methyl-5-hydroxy-6-(N-(tert-butoxycarbonyl)piperidin-4-yloxy) benzimidazole (a compound of formula (28)). To the resulting product in DMF was added imidazole (0.66 g) and (tert-butyldimethylsilyl)chloride (1.5 g). After stirring at ambient temperature for 1 hour the reaction was worked up between ethyl acetate and $H_2O$. The organic layer was dried, concentrated and purified by silica gel chromatography (hexane/ethyl acetate/$CH_2Cl_2$/methanol, gradient) to afford 2-methyl-5-(tert-butyldimethylsilyl)oxy-6-(N-(tert-butoxycarbonyl)piperidin-4-yloxy)benzimidazole.

PREPARATION 19

Compounds of formula (30)

To 2-methyl-5-(tert-butyldimethylsilyl)oxy-6-(N-(tert-butoxycarbonyl)piperidin-4-yloxy)benzimidazole (6.6 g) in DMF (50 mL) was added NaH (0.65 g) at ambient temperature. After stirring at ambient temperature for 30 minutes 7-bromomethyl-2-naphthonitrile (3.88 g) was added. The reaction mixture was stirred at ambient temperature for 1 hour. The reaction was worked up between ethyl acetate and $H_2O$. The organic layer was dried, concentrated and purified by silica gel chromatography (hexane/ethyl acetate/$CH_2Cl_2$/methanol, gradient) to afford 2-methyl-5-(tert-butyldimethylsilyl)oxy-6-(N-(tert-butoxycarbonyl) piperidin-4-yloxy)-1-(4-cyanonaphth-1-yl) methylbenzimidazole and 2-methyl-6-(tert-butyldimethylsilyl)oxy-5-(N-(tert-butoxycarbonyl) piperidin-4-yloxy)-1-(4-cyanonaphth-1-yl) methylbenzimidazole.

PREPARATION 20

Compounds of formula (31)

To 2-methyl-5-(tert-butyldimethylsilyl)oxy-6-(N-(tert-butoxycarbonyl)piperidin-4-yloxy)-1-(4-cyanonaphth-1-yl) methylbenzimidazole (3 g) in THF (50 mL) was added tetrabutyl ammonium fluoride (3 mL, 1M)) at ambient temperature. After stirring at ambient temperature for 30 minutes the solvent was removed. The reaction was worked up between ethyl acetate and $H_2O$. The organic layer was dried and concentrated to afford 2-methyl-5-hydroxy-6-(N-(tert-butoxycarbonyl)piperidin-4-yloxy)-1-(4-cyanonaphth-1-yl)methylbenzimidazole.

PREPARATION 21

Compounds of formula (32)

A. To 2-methyl-5-hydroxy-6-(N-(tert-butoxycarbonyl) piperidin-4-yloxy)-1-(4-cyanonaphth-1-yl) methylbenzimidazole (1.11 g) in DMF (50 mL) was added NaH (0.15 g) at ambient temperature. After stirring at ambient for 30 minutes ethyl bromoacetate (0.4 mL) was added. The reaction was stirred at ambient temperature for 1 hour and was worked up between ethyl acetate and $H_2O$. The organic layer was dried, concentrated and purified by silica gel chromatography (hexane/ethyl acetate/$CH_2Cl_2$/ methanol, gradient) to afford 2-methyl-5-(ethoxycarbonylmethoxy)-6-(N-(tert-butoxycarbonyl) piperidin-4-yloxy)-1-(4-cyanonaphth-1-yl) methylbenzimidazole.

B. In a similar manner, the following compounds of formula (32) were made:

2-methyl-5-(1-(methoxycarbonyl)ethoxy)-6-(N-(tert-butoxycarbonyl)piperidin-4-yloxy)-1-(4-cyanonaphth-1-yl)methylbenzimidazole;

2-methyl-5-(4-(methoxycarbonyl)benzyloxy)-6-(N-(tert-butoxycarbonyl)piperidin-4-yloxy)-1-(4-cyanonaphth-1-yl)methylbenzimidazole; and 2-methyl-5-(3-(methoxycarbonyl)benzyloxy)-6-(N-(tert-butoxycarbonyl)piperidin-4-yloxy)-1-(4-cyanonaphth-1-yl)methylbenzimidazole.

PREPARATION 22

Compounds of formula (33)

To 2-methyl-6-(tert-butyldimethylsilyl)oxy-5-(N-(tert-butoxycarbonyl)piperidin-4-yloxy)-1-(4-cyanonaphth-1-yl)

methylbenzimidazole (3 g) in THF (50 mL) was added Bu$_4$NF (4 mL, 1M)) at ambient temperature. After stirring at ambient temperature for 30 minutes the solvent was removed. The reaction was worked up between ethyl acetate and H$_2$O. The organic layer was dried, concentrated and purified by silica gel chromatography (hexane/ethyl acetate/ CH$_2$Cl$_2$/methanol, gradient) to afford 2-methyl-6-hydroxy-5-(N-(tert-butoxycarbonyl)piperidin-4-yloxy)-1-(4-cyanonaphth-1-yl)methylbenzimidazole.

PREPARATION 23

Compounds of formula (34)

To 2-methyl-6-hydroxy-5-(N-(tert-butoxycarbonyl) piperidin-4-yloxy)-1-(4-cyanonaphth-1-yl) methylbenzimidazole (2.8 g) in THF (50 mL) was first added N-benzyloxycarbonyl-4-hydroxypiperidine (1.7 g), PPh$_3$ (1.9 g), and then DEAD (1.2 mL) in a dropwise fashion. After stirring at ambient temperature for 1 hour the solvent was removed and the residue was separated by silica gel chromatography (hexane/ethyl acetate, gradient) to afford 2-methyl-6-(N-(benzyloxycarbonyl)piperidin-4-yloxy)-5-(N-(tert-butoxycarbonyl)piperidin-4-yloxy)-1-(4-cyanonaphth-1-yl)methylbenzimidazole.

PREPARATION 24

Compounds of formula (35) and (36)

To 2-methyl-6-(N-(benzyloxycarbonyl)piperidin-4-yloxy)-5-(N-(tert-butoxycarbonyl)piperidin-4-yloxy)-1-(4-cyanonaphth-1-yl)methylbenzimidazole (4 g) in CH$_2$Cl$_2$/ methanol (100 mL, 9:1, v/v) was added trifluoroacetic acid (20 mL). After stirring for 6 hours at ambient temperature the reaction was concentrated to afford the trifluoroacetic acid salt of 2-methyl-6-(piperidin-4-yloxy)-5-(N-(tert-butoxycarbonyl)piperidin-4-yloxy)-1-(4-cyanonaphth-1-yl) methylbenzimidazole (a compound of formula (35)). To the resulting product in THF (50 mL) was added ethyl bromoacetate (0.72 mL) and K$_2$CO$_3$ (5 g). After stirring at ambient temperature for 1 hour the reaction was worked up between ethyl acetate and H$_2$O. The organic layer was dried, concentrated and purified by silica gel chromatography (hexane/ ethyl acetate/CH$_2$Cl$_2$/methanol, gradient) to afford 2-methyl-6-(N-(ethoxycarbonyl-methyl)piperidin-4-yloxy)-5-(N-(tert-butoxycarbonyl)piperidin-4-yloxy)-1-(4-cyanonaphth-1-yl)methylbenzimidazole.

PREPARATION 25

Compounds of formula (38)

A. To 5-amino-2-methoxycarbonylphenol (60 g) in pyridine (200 mL) was added acetic anhydride (70 mL) at ambient temperature. After stirring at ambient temperature for 14 hours the solvent was removed to afford 5-acetylamino-2-methoxycarbonyl-1-acetoxybenzene.

B. In a similar manner, the following compound of formula (38) was prepared:
5-(2-methyl-1-oxopropyl)amino-2-methoxycarbonyl-1-(2-methyl-1-oxopropoxy)benzene.

PREPARATION 26

Compounds of formula (39)

A. To 5-acetylamino-2-methoxycarbonyl-1-acetoxybenzene (20 g) in trifluoroacetic acid (150 mL) was added HNO$_3$ (5 mL) at ambient temperature. After stirring at ambient temperature for 2 hours the solvent was removed. The resulting residue was recrystallized from ethyl acetate to afford a mixture of 5-acetylamino-4-nitro-2-methoxycarbonyl-1-hydroxybenzene and 5-acetylamino-6-nitro-2-methoxycarbonyl-1-hydroxybenzene.

B. In a similar manner, the following compounds of formula (39) were made:
5-(2-methyl-1-oxopropyl)amino-4-nitro-2-methoxycarbonyl-1-hydroxybenzene; and
5-(2-methyl-1-oxopropyl)amino-6-nitro-2-methoxycarbonyl-1-hydroxybenzene.

PREPARATION 27

Compounds of formulae (41)

A. To a mixture of 5-acetylamino-4-nitro-2-methoxycarbonyl-1-hydroxybenzene and 5-acetylamino-6-nitro-2-methoxycarbonyl-1-hydroxybenzene (15 g) in methanol (50 mL) was added Pd/C (10 g). The resulting mixture was hydrogenated at 50 psi for 3 hours until H$_2$ intake diminished. The catalyst was filtered off and the filtrate was concentrated to afford a mixture of 5-acetylamino-4-amino-2-methoxycarbonyl-1-hydroxybenzene and 5-acetylamino-6-amino-2-methoxycarbonyl-1-hydroxybenzene. This mixture was then refluxed in acetic acid (200 mL) for 2 hours. After removal of acetic acid the residue was worked up between ethyl acetate and aqueous NaHCO$_3$. The organic layer was dried and concentrated to afford a mixture of 2-methyl-6-hydroxy-5-methoxy-carbonylbenzimidazole and 2-methyl-4-hydroxy-5-methoxycarbonylbenzimidazole.

B. In a similar manner, the following compound of formulae (41) was made:
2-isopropyl-6-hydroxy-5-methoxycarbonylbenzimidazole.

PREPARATION 28

Compounds of formula (42)

To a mixture of 2-methyl-6-hydroxy-5-methoxycarbonylbenzimidazole and 2-methyl-4-hydroxy-5-methoxycarbonylbenzimidazole (7.2 g) in THF (50 mL) was added di-tert-butyldicarbonate (7.6 g) and triethylamine (5 mL). After stirring at 50° C. for 6 hours the solvent was removed and the residue was triturated with ethyl acetate and filtered to afford 1-tert-butoxycarbonyl-2-methyl-6-hydroxy-5-methoxycarbonylbenzimidazole and 1-tert-butoxycarbonyl-2-methyl-4-hydroxy-5-methoxycarbonylbenzimidazole.

PREPARATION 29

Compounds of formula (43)

To a mixture of 1-tert-butoxycarbonyl-2-methyl-5-hydroxy-6-methoxycarbonylbenzimidazole and 1-tert-butoxycarbonyl-2-methyl-6-hydroxy-5-methoxycarbonylbenzimidazole (3.7 g) in THF (50 mL) was first added N-tert-butoxycarbonyl-4-hydroxypiperidine (3.2 g), PPh$_3$ (4.2 g), and then DEAD (2.5 mL) in a dropwise fashion. After stirring at ambient temperature for 4 days the solvent was removed and the residue was separated by silica gel chromatography (hexane/ethyl acetate/CH$_2$Cl$_2$/ methanol, gradient) to afford a mixture of 1-tert-butoxycarbonyl-2-methyl-5-methoxycarbonyl-6-(N-(tert-butoxycarbonyl)piperidin-4-yloxy)benzimidazole and 1-tert-butoxycarbonyl-2-methyl-6-methoxycarbonyl-5-(N-(tert-butoxycarbonyl)piperidin-4-yloxy)benzimidazole.

PREPARATION 30

Compounds of formulae (44) and (45)

To a mixture of 1-tert-butoxycarbonyl-2-methyl-5-methoxycarbonyl-6-(N-(tert-butoxycarbonyl)piperidin-4-yloxy)benzimidazole and 1-tert-butoxycarbonyl-2-methyl-6-methoxycarbonyl-5-(N-(tert-butoxycarbonyl)piperidin-4-yloxy)benzimidazole (2.5 g) in methanol (200 mL) was bubbled in ammonia at 0° C. After stirring for 2 hours at ambient temperature the reaction mixture was concentrated. The resulting residue was purified by silica gel chromatography (hexane/ethyl acetate/$CH_2Cl_2$/methanol, gradient) to afford 2-methyl-5-methoxycarbonyl-6-(N-(tert-butoxycarbonyl)piperidin-4-yloxy)benzimidazole. To this product (0.66 g) in DMF (20 mL) was added NaH (0.075 g) at ambient temperature. After stirring at ambient temperature for 30 minutes 7-bromomethyl-2-naphthonitrile (0.5 g) was added at 0° C. The reaction mixture was stirred at ambient temperature for 0.5 hours. The reaction was worked up between ethyl acetate and $H_2O$. The organic layer was dried and concentrated to afford a mixture of 1-(4-cyanonaphth-1-yl)methyl-2-methyl-5-methoxycarbonyl-6-(N-(tert-butoxycarbonyl)piperidin-4-yloxy)benzimidazole and 1-(4-cyanonaphth-1-yl)methyl-2-methyl-6-methoxycarbonyl-5-(N-(tert-butoxycarbonyl)piperidin-4-yloxy)benzimidazole in a ratio of 2 to 1, respectively.

PREPARATION 31

Compounds of formula (46)

To 3,5-dinitro-1-carboxy-2-chlorobenzene (53 g) in acetonitrile (500 mL) and triethylamine (100 mL) was added benzylamine at 0° C. in a dropwise fashion. The reaction was allowed to warm to ambient temperature and stirred at ambient temperature for 1 hour. The solvent was removed under reduced pressure to afford the crude product, 3,5-dinitro-1-carboxy-2-(benzyl)aminobenzene. The product was dissolved in methanol/12N HCl (400 mL, 3:1, v/v), and was hydrogenated at 60 psi for 3 hours until $H_2$ intake stopped. The solvent was removed under reduced pressure to afford the crude product, 2,3,5-triamino-1-carboxybenzene. To the product in pyridine (400 mL) was added isobutyric anhydride (200 mL), and the reaction mixture was stirred at ambient temperature for 14 hours. The solvent was removed under reduced pressure to afford the crude product, 2,3,5-tri(isopropylcarbonylamino)-1-carboxybenzene. The product was refluxed in methanol/12N HCl (500 mL, 4:1, v/v) for 16 hours to afford the desired product, 2-isopropyl-4-methoxycarbonyl-6-aminobenzimidazole, after removal of the solvents under reduced pressure.

PREPARATION 32

Compounds of formula (48)

To 2-isopropyl-4-methoxycarbonyl-6-aminobenzimidazole in methanol/acetic acid (300 mL, 2:1, v/v) was added N-tert-butoxycarbonyl-4-piperidone (80 g), followed by $NaCNBH_4$ (9 g) at ambient temperature. After stirring at ambient temperature for 1 hour the solvents were removed and the resulting residue was worked up between ethyl acetate and $H_2O$. The organic layer was dried, concentrated, and purified by silica gel chromatography (hexane/ethyl acetate/$CH_2Cl_2$/methanol, gradient) to afford 2-isopropyl-4-methoxycarbonyl-6-(N-(tert-butoxycarbonyl) piperidin-4-ylamino)benzimidazole as a foam.

PREPARATION 33

Compounds of formula (49)

To 2-isopropyl-4-methoxycarbonyl-6-(N-(tert-butoxycarbonyl)piperidin-4-ylamino)benzimidazole (3.3 g) in DMF (200 mL) was added NaH (0.35 g) at ambient temperature. After stirring at ambient temperature for 30 minutes, the reaction flask was cooled to $-10°$ C. and 7-bromomethyl-2-naphthonitrile (2.2 g) was added. The reaction was allowed to warm to ambient temperature and stirred at ambient temperature for 15 hours. The reaction was worked up between ethyl acetate and $H_2O$. The organic layer was dried, concentrated and purified by silica gel chromatography (hexane/ethyl acetate/$CH_2Cl_2$/methanol, gradient) to afford 1-(4-cyanonaphth-1-yl)methyl-2-isopropyl-4-methoxycarbonyl-6-(N-(tert-butoxycarbonyl) piperidin-4-ylamino)benzimidazole, and 1-(4-cyanonaphth-1-yl)methyl-2-isopropyl-7-methoxycarbonyl-5-(N-(tert-butoxycarbonyl)-piperidin-4-ylamino)benzimidazole.

PREPARATION 34

Compounds of formula (51)

To a solution of 5-aminobenzimidazole (5.2 g, 40 mmol), N-tert-butoxycarbonyl-4-piperidone (8.0 g, 40 mmol), and acetic acid (3 mL) in methanol (250 mL) and methylene chloride (50 mL) at 0° C. was added sodium cyanoborohydride (3.77 g, 60 mmol). The solution was stirred for 20 minutes at 0° C. when it was allowed to warm to ambient temperature. After 12 hours, the reaction was worked up with ethyl acetate and water, dried ($MgSO_4$), and chromatographed on silica gel eluting with 7% methanol in methylene chloride to recover 9.47 g (77%) of 5-((N-(tert-butoxycarbonyl)piperidin-4-yl)amino)benzimidazole.

PREPARATION 35

Compounds of formula (52) and (54)

A. To a solution of 5-((N-(tert-butoxycarbonyl)piperidin-4-yl)amino)benzimidazole (1.50 g, 4.75 mmol) in DMF (30 mL) at 0° C. was added NaH (210 mg, 5.2 mmol). The solution was stirred for 0.5 hours when tosyl chloride (1.0 g, 5.2 mmol) was added. The reaction mixture was stirred for 1 hour at 0° C. when it was worked up with ethyl acetate and water, dried ($MgSO_4$), and concentrated to an oil to afford 1-tosyl-5-((N-(tert-butoxycarbonyl)piperidin-4-yl)amino) benzimidazole and its regioisomer, 1-tosyl-6-((N-(tert-butoxycarbonyl)piperidin-4-yl)amino)benzimidazole. The resulting oil was taken up in DMF (30 mL) when it was charged with $K_2CO_3$ (4 g) and methyl iodide (3 mL). After 12 hours at ambient temperature, the reaction mixture was worked up with ethyl acetate and water, dried ($MgSO_4$), and concentrated to an oil. The resulting tosylated product, 1-tosyl-5-((N-(tert-butoxycarbonyl)piperidin-4-yl)(methyl) amino)benzimidazole and the corresponding regioisomer, was taken up in methanol (80 mL) and NaOH (0.3 g, 7.5 mmol) was added. After 1 hour at ambient temperature, the methanol was removed in vacuo and the product recovered via chromatography on silica gel eluting with 5% to 10% methanol in methylene chloride to give 473 mg (30%) 5-((N-(tert-butoxycarbonyl)piperidin-4-yl)(methyl)amino) benzimidazole.

B. In a similar manner, to a solution of 1-tosyl-2-methyl-5-((N-(tert-butoxycarbonyl)piperidin-4-yl)amino) benzimidazole (2.7 g, 5.58 mmol) in DMF (15 mL) was added $K_2CO_3$ (3.85 g, 28 mmol) and methyl 3-bromo-2-methylene-propionate (1 g, 5.58 mmol). The solution was stirred at ambient temperature for 12 hours when it was worked up with ethyl acetate and water, dried ($MgSO_4$), and concentrated to recover a foam (2.5 g) containing 1-tosyl-2-methyl-5-(N-(tert-butoxycarbonyl)piperidin-4-yl)((2- methoxycarbonyl)prop-2-en-1-yl)aminobenzimidazole and trace starting material and DMF.

C. To a solution of the product of Paragraph B above, 1-tosyl-2-methyl-5-(N-(tert-butoxycarbonyl)piperidin-4-yl) (2-(methoxycarbonyl)prop-2-en-1-yl)aminobenzimidazole, (2.5 g) in ethanol (100 mL) and ethyl acetate (30 mL) was charged with Raney nickel (1 mL of a 50% water slurry) and subjected to an atmosphere of hydrogen (20 psi). After 6 hours, the catalyst was filtered off, the solution dried ($MgSO_4$) and concentrated to a solid to recover 1.5 g of 1-tosyl-2-methyl-5-(N-(tert-butoxycarbonyl)piperidin-4-yl) (2-(methoxycarbonyl)prop-1-yl)aminobenzimidazole.

D. To a solution of 1-tosyl-2-methyl-5-(N-(tert-butoxycarbonyl)piperidin-4-yl)aminobenzimidazole (6.1 g, 12.1 mmol) and triethylamine (3.4 mL, 24 mmol) in methylene chloride (30 mL) at 0° C. was added ethyl succinyl chloride (2.1 mL, 14.5 mmol). After 2.5 hours, the solution was filtered and extracted with water and 1M NaOH to recover 1-tosyl-2-methyl-5-(N-(tert-butoxycarbonyl) piperidin-4-yl)((2-(ethoxycarbonyl)ethyl)carbonyl) aminobenzimidazole.

E. In a manner similar to that described above in Paragraph A wherein the compound is treated with sodium hydroxide in methanol, the following compounds of formula (55) were made:
2-methyl-5-(N-(tert-butoxycarbonyl)piperidin-4-yl)(2-(methoxycarbonyl)prop-1-yl)aminobenzimidazole;
2-methyl-5-(N-(tert-butoxycarbonyl)piperidin-4-yl)( (methoxycarbonyl)methyl)aminobenzimidazole;
2-methyl-5-(N-(tert-butoxycarbonyl)piperidin-4-yl)((2-(ethoxycarbonyl)ethyl)carbonyl)aminobenzimidazole; and
2-methyl-5-(N-(tert-butoxycarbonyl)piperidin-4-yl)(3-(methoxycarbonyl)prop-1-yl)aminobenzimidazole.

PREPARATION 36

Compounds of formula (56)

To a solution of 1,2-diamino-4-methoxybenzene (50 g) in pyridine (400 mL) at 0° C. was added isobutyryl chloride (100 mL). After 3 hours, the solvent was removed in vacuo and the solid partitioned between methylene chloride and water. The organic layer was concentrated and taken up in 4N HCl, and then heated to reflux overnight. The solution was concentrated to a solid, neutralized with sodium bicarbonate, then concentrated once again to a solid. The solid was washed with THF to recover 2-isopropyl-5-methoxy-6-nitrobenzimidazole (29 g).

PREPARATION 37

Compounds of formula (57)

A. 2-Isopropyl-5-methoxybenzimidazole (50 g) was dissolved in 150 mL TFA and to the mixture was added 5 mL 90% nitric acid. The reaction was stirred overnight, and the solvents removed in vacuo and the residue neutralized to pH 7 with saturated aqueous sodium bicarbonate. The residue was extracted with ethyl acetate (4×100 mL). The combined ethyl acetate fractions were dried over sodium sulfate and concentrated to give a dark residue. Chromatography (3% methanol/methylene chloride) gave 2-isopropyl-4-nitro-5-methoxybenzimidazole as a yellow solid, 24 g. Also obtained was 25 g of 2-isopropyl-5-nitro-6-methoxybenzimidazole.

B. In a similar manner, the following compound of formula (57) was made:
2-methyl-4-nitro-5-methoxybenzimidazole and 2-methyl-5-nitro-6-methoxy-benzimidazole.

C. Alternatively, to a solution of 2-isopropyl-5-methoxybenzimidazole (50 g) in trifluoroacetic acid (150 mL) at ambient temperature was added fuming $HNO_3$ (15 mL). The reaction was stirred overnight, the solvent removed in vacuo and the residue quenched with potassium carbonate. The aqueous layer was then extracted with ethyl acetate, the organic layer dried and concentrated to recover a mixture of the regioisomers, 2-isopropyl-6-methoxy-5-nitrobenzimidazole and 2-isopropyl-4-nitro-5-methoxybenzimidazole (3:1 ratio) and. The regioisomers were separated by chromatography (3% methanol/methylene chloride) to recover 2-isopropyl-6-methoxy-5-nitrobenzimidazole (24 g).

PREPARATION 38

Compounds of formula (58)

A. A solution of 2-isopropyl-6-methoxy-5-nitrobenzimidazole (17 g) in concentrated HBr (300 mL) was refluxed for 7 hours when the solvent was removed in vacuo. The residue was quenched with potassium carbonate and extracted with ethyl acetate. The organic layer was dried and concentrated to recover 2-isopropyl-6-hydroxy-5-nitrobenzimidazole as well as an HBr addition product (approx. 2:1 ratio).

B. In a similar manner, the following compound of formula (58) was made:
2-methyl-6-hydroxy-5-nitrobenzimidazole;
2-methyl-5-hydroxy-4-nitrobenzimidazole; and
2-isopropyl-5-hydroxy-4-nitrobenzimidazole.

PREPARATION 39

Compounds of formula (59)

A. To a solution of 2-isopropyl-6-hydroxy-5-nitrobenzimidazole and the HBr addition product (15 g), N-tert-butoxycarbonyl-4-hydroxypiperidine (17.7 g), $PPh_3$ (23.1 g), and THF (150 mL) at room temperature was added DEAD (14 mL). After 4 hours, the solvent was removed in vacuo and the product recovered from the crude using chromatography (3% methanol/methylene chloride) to yield 2-isopropyl-5-(N-(tert-butoxycarbonyl)piperidin-4-yloxy)-6-nitrobenzimidazole (16.5 g).

B. In a similar manner, the following compound of formula (59) was made:
2-methyl-6-(N-(tert-butoxycarbonyl)piperidin-4-yloxy)-5-nitrobenzimidazole;
2-methyl-5-(N-(tert-butoxycarbonyl)piperidin-4-yloxy)-4-nitrobenzimidazole; and
2-isopropyl-5-(N-(tert-butoxycarbonyl)piperidin-4-yloxy)-4-nitrobenzimidazole.

PREPARATION 40

Compounds of formula (60)

A. To a solution of 2-isopropyl-6-(N-(tert-butoxycarbonyl)piperidin-4-yloxy)-5- nitrobenzimidazole (16.5 g) in DMF (50 mL) at 0° C. was added NaH (2.45 g). After 40 minutes, 7-bromomethyl-2-naphthonitrile (11 g) was added and the reaction stored in the freezer (−35° C.) overnight. The reaction was worked up with ethyl acetate and water and the organic layer dried and concentrated to an oil. The product was isolated using 2% methanol/methylene chloride on silica gel to give a mixture of 1-(4-cyanonaphth- 1-yl)methyl-2-isopropyl-6-(N-(tert-butoxycarbonyl) piperidin-4-yloxy)-5-nitrobenzimidazole and 1-(4-cyanonaphth-1-yl)methyl-2-isopropyl-5-(N-(tert-butoxycarbonyl)piperidin-4-yloxy)-6-nitrobenzimidazole (2.5:1 ratio, 16.5 g).

B. In a similar manner, the following compound of formula (60) was made:
1-(4-cyanonaphth-1-yl)methyl-2-methyl-6-(N-(tert-butoxycarbonyl)piperidin-4-yloxy)-5-nitrobenzimidazole;
1-(4-cyanonaphth-1-yl)methyl-2-methyl-6-(N-(tert-butoxycarbonyl)piperidin-4-yloxy)-7-nitrobenzimidazole; and
1-(4-cyanonaphth-1-yl)methyl-2-isopropyl-6-(N-(tert-butoxycarbonyl)piperidin-4-yloxy)-7-nitrobenzimidazole.

PREPARATION 41

Compounds of formula (61)

A. 1-(4-Cyanonaphth-1-yl)methyl-2-isopropyl-7-nitro-6-(N-(tert-butoxycarbonyl)piperidin-4-yloxy)benzimidazole (12 g, 21 mmoL, 1 eq.) was dissolved in 400 mL dry pyridine and to this was added tin (II) chloride dihydrate (71 g, 315 mmoL, 15 eq.) which formed a finely divided suspension. The slurry was heated to 50° C. for 14 hours. The pyridine was stripped off, and the salts triturated in 1 L ethyl acetate. The salts were removed by filtration through Celite and the filtrate was concentrated to give a brown oil. Chromatography (3/2 ethyl acetate/hexanes) gave 7.6 g (67% yield) of 1-(4-cyanonaphth-1-yl)methyl-2-isopropyl-7-amino-6-(N-(tert-butoxycarbonyl)piperidin-4-yloxy) benzimidazole as a tan foam.

B. Alternatively, to a solution 1-(4-cyanonaphth-1yl) methyl-2-isopropyl-5-(N-(tert-butoxycarbonyl)piperidin-4-yloxy)-6-nitrobenzimidazole and 1-(4-cyanonaphth-1-yl) methyl-2-isopropyl-6-(N-(tert-butoxycarbonyl)piperidin-4-yloxy)-5-nitrobenzimidazole (16.5 g) in triethylamine (100 mL) and pyridine (50 mL) was added $SnCl_2 \cdot H_2O$ (32.7 g). The reaction was warmed to 60° C. for 3 hours when the solvent was removed in vacuo. The solid was taken up in ethyl acetate and filtered. The ethyl acetate was removed in vacuo and the product isolated using silica gel eluting with 5% methanol/methylene chloride to recover 1-(4-cyanonaphth-1-yl)methyl-2-isopropyl-6-(N-(tert-butoxycarbonyl)piperidin-4-yloxy)-5-aminobenzimidazole (5.7 g).

C. In a similar manner, the following compound of formula (61) was made:
1-(4-cyanonaphth-1-yl)methyl-2-methyl-6-(N-(tert-butoxycarbonyl)piperidin-4-yloxy)-5-aminobenzimidazole.

PREPARATION 42

Compounds of formula (62)

A. 1-(4-cyanonaphth-1-yl)methyl-2-isopropyl-7-amino-6-(N-(tert-butoxycarbonyl)piperidin-4-yloxy) benzimidazole (5.5 g, 10 mmol, 1 eq.) was dissolved in 50 mL dry DMF and to this was added methyl bromoacetate (1.2 mL, 12 mmoL, 1.2 eq.) and then potassium carbonate (1.4 g, 1.2 eq.). The reaction was stirred at 20° C. for 2 days. TLC indicated the reaction to be nearly complete. The reaction mixture was worked up between water and ethyl acetate. The ethyl acetate was removed in vacuo and the product was isolated by chromatography (3/2 hexanes/ethyl acetate) to afford 5 g of 1-(4-cyanonaphth-1-yl)methyl-2-isopropyl-7-((methoxycarbonyl)methyl)amino-6-(N-(tert-butoxycarbonyl)piperidin-4-yloxy)benzimidazole with a small amount of the diaddition product.

B. Alternatively, to a suspension of 1-(4-cyanonaphth-1-yl)methyl-2-isopropyl-6-(N-(tert-butoxycarbonyl)piperidin-4-yloxy)-5-aminobenzimidazole (500 mg), potassium carbonate (642 mg), and DMF was added methyl 4-bromomethylbenzoate (212 mg). After 2 days at ambient temperature, the reaction was worked up with ethyl acetate and water. The organic layer was dried and the product isolated on silica gel using 2% methanol/methylene chloride to recover 1-(4-cyanonaphth-1-yl)methyl-2-isopropyl-6-(N-(tert-butoxycarbonyl)piperidin-4-yloxy)-5-(N-(4-methoxycarbonylbenzyl)amino)benzimidazole (440 mg).

C. In a similar manner, the following compounds of formula (62) were made:
1-(4-cyanonaphth-1-yl)methyl-2-isopropyl-6-(N-(tert-butoxycarbonyl)piperidin-4-yloxy)-5-(N-(2-methoxycarbonylethyl)amino)benzimidazole;
1-(4-cyanonaphth-1-yl)methyl-2-isopropyl-6-(N-(tert-butoxycarbonyl)piperidin-4-yloxy)-5-(N-(1-methoxycarbonyl-1-methylethyl)amino)benzimidazole;
1-(4-cyanonaphth-1-yl)methyl-2-methyl-6-(N-(tert-butoxycarbonyl)piperidin-4-yloxy)-5-(N-(4-methoxycarbonylbenzyl)amino)benzimidazole; and
1-(4-cyanonaphth-1-yl)methyl-2-isopropyl-6-(N-(tert-butoxycarbonyl)piperidin-4-yloxy)-5-(N-(4-methoxycarbonylbenzyl)amino)benzimidazole.

EXAMPLE 1

Compounds of formula (Ia)

A. To a slurry of 1-(4-cyanonaphth-1-yl)methyl-2-isopropyl-6-(N-(tert-butoxycarbonyl)piperidin-4-yloxy) benzimidazole and 1-(4-cyanonaphth-1-yl)methyl-2-isopropyl-5-(N-(tert-butoxycarbonyl)piperidin-4-yloxy) benzimidazole (320 mg, 62 mmol) and ethanol (10 mL) cooled in a dry ice/acetone bath was bubbled HCl (g). After the solution was saturated, the reaction flask was sealed and the temperature maintained at 5° C. for 16 hours. The solvent was removed in vacuo. The residue was dissolved in ethanol (20 mL). The solution was cooled in a dry ice/acetone bath and ammonia (g) was bubbled in. The reaction flask was sealed then heated at 80° C. for 4 hours. The solvent was removed. The mixture was separated by HPLC on a $C^{18}$ Dynamax column with a 5–20% acetonitrile in water gradient with 0.1% trifluoroacetic acid to afford 1-(4-amidinonaphth-1-yl)methyl-2-isopropyl-6-(piperidin-4-yloxy)benzimidazole ditrifluoroacetate salt, 1H NMR (300 MHz, DMSO) δ 9.40 (s, 2H), 9.20 (s, 2H), 8.60 (br s, 2H), 8.40 (s, 1H), 8.18 (d, 1H), 8.14 (d, 1H), 7.90–7.75 (m, 3H), 7.60 (m, 1H), 7.40 (s, 1H), 7.25 (dd, 1H), 6.05 (s, 2H), 4.70 (m, 1H), 3.65 (septuplet, 1H), 3.30–3.20 (m, 2H), 3.15–3.00 (m, 2H), 2.18–2.00 (m, 2H), 1.90–1.80 (m, 2H), 1.40 (d, 6H); and 1-(4-amidinonaphth-1-yl)methyl-2-isopropyl-5-(piperidin-4-yloxy)benzimidazole ditrifluoroacetate salt, 1H NMR (300 MHz, DMSO) δ 9.40 (s, 2H), 9.20 (s, 2H), 8.60 (br s, 2H), 8.40 (s, 1H), 8.18 (d, 1H), 8.14 (d, 1H), 7.90–7.75 (m, 3H), 7.65-7.60 (m, 2H), 7.25 (dd, 1H), 6.05 (s, 2H), 4.70 (m, 1H), 3.65 (septuplet, 1H), 3.30–3.20 (m, 2H), 3.15–3.00 (m, 2H), 2.18–2.00 (m, 2H), 1.85–1.70 (m, 2H), 1.35 (d, 6H).

B. In a similar manner, the following compounds were made:
1-(4-amidinonaphth-1-yl)methyl-2-propyl-6-(piperidin-4-yloxy)benzimidazole, $^1$H NMR (300 MHz, DMSO) δ

9.40 (s, 2H), 9.20 (s, 2H), 8.60 (br s, 1H), 8.40 (s, 1H), 8.18 (d, 1H), 8.10 (s, 1H), 7.95 (s, 1H), 7.85 (d, 1H), 7.75 (d, 1H), 7.65 (d, 1H), 7.40 (s, 1H), 7.20 (dd, 1H), 5.95 (s, 2H), 4.70 (m, 1H), 3.30–3.00 (m, 6H), 2.18–2.00 (m, 2H), 1.85–1.70 (m, 4H), 0.90 (t, 3H);

1-(4-amidinonaphth-1-yl)methyl-2-propyl-5-(piperidin-4-yloxy)benzimidazole, $^1$H NMR (300 MHz, DMSO) δ 9.40 (s, 2H), 9.20 (s, 2H), 8.60 (br s, 2H), 8.40 (s, 1H), 8.18 (d, 1H), 8.14 (d, 1H), 7.90–7.80 (m, 3H), 7.65 (d, 1H), 7.60 (s, 1H), 7.25 (dd, 1H), 6.00 (s, 2H), 4.70 (m, 1H), 3.30–3.00 (m, 6H), 2.18–2.00 (m, 2H), 1.85–1.70 (m, 4H), 0.90 (t, 3H);

1-(4-amidinonaphth-1-yl)methyl-2-isopropyl-4-methoxy-6-(piperidin-4-yloxy)benzimidazole, $^1$H NMR (300 MHz, DMSO) δ 9.40 (s, 2H), 9.20 (s, 2H), 8.60 (br s, 2H), 8.40 (s, 1H), 8.18 (d, 1H), 8.14 (d, 1H), 7.80 (d, 1H), 7.75 (s, 1H), 7.60 (d, 1H), 7.20 (s, 1H), 6.85 (s, 1H), 6.00 (s, 2H), 4.70 (m, 1H), 4.05 (s, 3H), 3.60 (septuplet, 1H), 3.30–3.25 (m, 2H), 3.15–3.05 (m, 2H), 2.18–2.00 (m, 2H), 1.90–1.80 (m, 2H), 1.35 (d, 6H);

1-(4-amidinonaphth-1-yl)methyl-2-isopropyl-7-methoxy-5-(piperidin-4-yloxy)benzimidazole, $^1$H NMR (300 MHz, DMSO) δ 9.40 (s, 2H), 9.20 (s, 2H), 8.60 (br s, 2H), 8.40 (s, 1H), 8.18 (d, 1H), 8.14 (d, 1H), 7.80 (d, 1H), 7.75 (s, 1H), 7.60 (d, 1H), 6.97 (s, 1H), 6.80 (s, 1H), 6.05 (s, 2H), 4.80 (m, 1H), 3.85 (s, 3H), 3.65 (septuplet, 1H), 3.30–3.25 (m, 2H), 3.20–3.05 (m, 2H), 2.18–2.00 (m, 2H), 1.90–1.80 (m, 2H), 1.40 (d, 6H);

1-(4-amidinonaphth-1-yl)methyl-2-methyl-6-(piperidin-4-yloxy)benzimidazole, $^1$H NMR (300 MHz, DMSO) δ 9.40 (s, 2H), 9.20 (s, 2H), 8.60 (br s, 1H), 8.40 (s, 1H), 8.18 (d, 1H), 8.10 (s, 1H), 7.90–7.75 (m, 3H), 7.70 (d, 1H), 7.58 (s, 1H), 7.20 (dd, 1H), 5.95 (s, 2H), 4.70 (m, 1H), 3.30–3.20 (m, 2H), 3.10–3.00 (m, 2H), 2.80 (s, 3H), 2.10–2.00 (m, 2H), 1.85–1.75 (m, 2H);

1-(4-amidinonaphth-1-yl)methyl-2-methyl-5-(piperidin-4-yloxy)benzimidazole, $^1$H NMR (300 MHz, DMSO) δ 9.40 (s, 2H), 9.20 (s, 2H), 8.60 (br s, 1H), 8.40 (s, 1H), 8.18 (d, 1H), 8.10 (s, 1H), 7.99 (s, 1H), 7.95 (d, 1H), 7.75 (d, 1H), 7.65 (d, 1H), 7.40 (s, 1H), 7.20 (dd, 1H), 5.95 (s, 2H), 4.80 (m, 1H), 3.30–3.20 (m, 2H), 3.10–3.00 (m, 2H), 2.90 (s, 3H), 2.10–2.00 (m, 2H), 1.95–1.85 (m, 2H);

1-(4-amidinonaphth-1-yl)methyl-6-(piperidin-4-yloxy)benzimidazole, $^1$H NMR (300 MHz, DMSO) δ 9.80 (s, 1H), 9.40 (s, 2H), 9.20 (s, 2H), 8.60 ( br s, 2H), 8.40 (s, 1H), 8.20–8.00 (m, 3H), 7.90–7.75 (m, 3H), 7.60 (s, 1H), 7.25 (dd, 1H), 6.00 (s, 2H), 4.70 (m, 1H), 3.30–3.20 (m, 2H), 3.20–3.00 (m, 2H), 2.20–2.00 (m, 2H), 1.85–1.75 (m, 2H);

1-(4-amidinonaphth-1-yl)methyl-5-(piperidin-4-yloxy)benzimidazole, $^1$H NMR (300 MHz, DMSO) δ 9.80 (s, 1H), 9.40 (s, 2H), 9.20 (s, 2H), 8.60 (br s, 2H), 8.40 (s, 1H), 8.20–8.00 (m, 3H), 7.90–7.75 (m, 3H), 7.45 (s, 1H), 7.20 (dd, 1H), 6.00 (s, 2H), 4.80 (m, 1H), 3.30–3.20 (m, 2H), 3.20-3.00 (m, 2H), 2.20–2.00 (m, 2H), 1.90–1.70 (m, 2H);

1-(4-amidinonaphth-1-yl)methyl-2-methyl-5-(aminocarbonyl)methoxy-6-(piperidin-4-yloxy)benzimidazole, 1-(4-amidinonaphth-1-yl)methyl-2-methyl-6-(aminocarbonyl)methoxy-5-(piperidin-4-yloxy)benzimidazole, 1-(4-amidinonaphth-1-yl)methyl-2-methyl-6-(carboxy)methoxy-5-(piperidin-4-yloxy)benzimidazole, 1-(4-amidinonaphth-1-yl)methyl-2-methyl-6-(piperidin-3-yloxy)benzimidazole, 1-(4-amidinonaphth-1-yl)methyl-2-(2-aminocarbonylethyl)-6-(piperidin-4-yloxy)benzimidazole, 1-(4-amidinonaphth-1-yl)methyl-2-(2-carboxyethyl)-6-(piperidin-4-yloxy)benzimidazole, 1-(4-amidinonaphth-1-yl)methyl-2-ethyl-6-(piperidin-4-yloxy)benzimidazole, $^1$H NMR (300 MHz, DMSO) δ 9.40 (s, 2H), 9.20 (s, 2H), 8.50 (br s, 1H), 8.40 (s, 1H), 8.20–8.05 (m, 2H), 7.90–7.80 (m, 3H), 7.65 (d, 1H), 7.60 (s, 1H) 7.25 (dd, 1H), 6.00 (s, 2H), 4.70 (m, 1H), 3.30–3.00 (m, 6H), 2.10–2.00 (m, 2H), 1.90–1.70 (m, 2H), 1.35 (t, 3H);

1-(4-amidinonaphth-1-yl)methyl-2-ethyl-5-(piperidin-4-yloxy)benzimidazole, $^1$H NMR (300 MHz, DMSO) δ 9.40 (s, 2H), 9.20 (s, 2H), 8.60 (br s, 1H), 8.40 (s, 1H), 8.15 (d, 1H), 8.10 (d, 1H), 7.90 (s, 1H), 7.85 (d, 1H), 7.75 (d, 1H), 7.60 (d, 1H), 7.40 (s, 1H), 7.20 (dd, 1H), 6.00 (s, 2H), 4.70 (m, 1H), 3.30–3.00 (m, 6H), 2.10–2.00 (m, 2H), 1.90–1.70 (m, 2H), 1.35 (t, 3H);

1-(4-amidinonaphth-1-yl)methyl-2-methyl-5-(carboxy)methoxy-6-(piperidin-4-yloxy)benzimidazole, 1-(4-amidinonaphth-1-yl)methyl-6-(N-(piperidin-4-yl)-N-(4-methoxycarbonylbenzyl)amino)benzimidazole, 1-(4-amidinonaphth-1-yl)methyl-6-(N-(piperidin-4-yl)-N-(4-carboxybenzyl)amino)benzimidazole, and 1-(4-amidinonaphth-1-yl)methyl-2-methyl-6-(N-(piperidin-4-yl)-N-(2-(methoxycarbonyl)ethyl)amino)benzimidazole.

EXAMPLE 2

Compounds of formula (Ib)

A. To a solution of 1-(4-amidinonaphth-1-yl)methyl-2-isopropyl-6-(piperidin-4-yloxy)benzimidazole and 1-(4-amidinonaphth-1-yl)methyl-2-isopropyl-5-(piperidin-4-yloxy)benzimidazole as a 1:1 mixture of compounds (288 mg, 0.65 mmol) and methanol (5 mL) was added triethylamine (0.54 mL, 3.90 mmol) and ethylacetimidate (320 mg, 2.60 mmol). After stirring for 16 hours, the reaction was concentrated. The mixture was separated on HPLC on a C$^{18}$ Dynamax column with a 1–20% acetonitrile in water gradient with 0.1% trifluoroacetic acid to afford 1-(4-amidinonaphth-1-yl)methyl-2-isopropyl-6-(N-(1-iminoethyl)piperidin-4-yloxy)benzimidazole ditrifluoroacetate salt; $^1$H NMR (300 MHz, DMSO) δ 9.40 (s, 2H), 9.20 (s, 2H), 9.15 (s, 1H), 8.60 (s, 1H), 8.40 (s, 1H), 8.20–8.10 (m, 2H), 7.90–7.70 (m, 3H), 7.60–7.50 (m, 2H), 7.24 (d, 1H), 6.00 (s, 2H), 4.80 (m, 1H), 3.80–3.40 (m, 5H), 2.28 (s, 3H), 2.05 (m, 2H), 1.80 (m, 2H), 1.30 (d, 6H); and 1-(4-amidinonaphth-1-yl)methyl-2-isopropyl-5-(N-(1-iminoethyl)piperidin-4-yloxy)benzimidazole ditrifluoroacetate salt; $^1$H NMR (300 MHz, DMSO) δ 9.40 (s, 2H), 9.20 (s, 2H), 9.10 (s, 1H), 8.60 (s, 1H), 8.40 (s, 1H), 8.20–8.00 (m, 2H), 7.90–7.75 (m, 3H), 7.60 (dd, 1H), 7.40 (s, 1H), 7.25 (dd, 1H), 6.00 (s, 2H), 4.80 (m, 1H), 3.80–3.65 (m, 3H), 3.55 (m, 2H), 2.30 (s, 3H), 2.10 (m, 2H), 1.80 (m, 2H), 1.40 (d, 6H).

B. In a similar manner, the following compounds were made:

1-(4-amidinonaphth-1-yl)methyl-2-methyl-6-(N-(1-iminoethyl)piperidin-4-yloxy)benzimidazole, $^1$H NMR (300 MHz, DMSO) δ 9.40 (s, 2H), 9.30 (s., 2H), 9.15 (s, 1H), 8.60 (s, 1H), 8.40 (s, 1H), 8.20–8.05 (m, 2H), 7.90–7.75 (m, 3H), 7.65 (d, 1H), 7.60 (s, 1H), 7.25 (dd, 1H), 6.00 (s, 2H), 4.80 (m, 1H), 3.80–3.65 (m, 2H), 3.60–3.50 (m, 2H), 2.90 (s, 3H), 2.25 (s, 3H), 2.10–2.00 (m, 2H), 1.80–1.65 (m, 2H).

1-(4-amidinonaphth-1-yl)methyl-2-methyl-5-(N-(1-iminoethyl)piperidin-4-yloxy)benzimidazole, $^1$H NMR (300 MHz, DMSO) δ 9.40 (s, 2H), 9.20 (s, 2H), 9.10 (s, 1H), 8.60 (s, 1H), 8.40 (s, 1H), 8.20–8.00 (m, 2H), 7.95 (s, 1H), 7.80 (d, 1H), 7.70 (d, 1H), 7.65 (d, 1H), 7.40 (s, 1H), 7.20 (dd, 1H), 5.95 (s, 2H), 4.80 (m, 1H), 3.85–3.65 (m, 2H), 3.60–3.50 (m, 2H), 2.90 (s, 3H), 2.25 (s, 3H), 2.10–2.00 (m, 2H), 1.95–1.85 (m, 2H);

1-(4-amidinonaphth-1-yl)methyl-2-methyl-6-(N-(1-iminoethyl)piperidin-3-yloxy)benzimidazole, $^1$H-NMR (300 MHz, DMSO) δ 9.50 (s, 2H), 9.45 (s,2H), 9.30 (d, 1H), 8.80 (s, 1H), 8.40 (s, 1H), 8.20 (dd, 2H), 7.80 (dd, 2H), 7.60 (dd, 2H), 7.20 (d, 1H), 5.90 (s, 2H), 4.80 (m, 1H), 3.90–3.40 (m, 4H), 2.80 (s, 3H), 1.95–1.50 (m, 6H);

1-(4-amidinonaphth-1-yl)methyl-2-ethyl-6-(N-(1-iminoethyl)piperidin-4-yloxy)benzimidazole, $^1$H NMR (300 MHz, DMSO) δ 9.40 (s, 2H), 9.30 (s, 2H), 9.15 (s, 1H), 8.60 (s, 1H), 8.40 (s, 1H), 8.20–8.05 (m, 2H), 7.90–7.75 (m, 3H), 7.65 (d, 1H), 7.60 (s, 1H), 7.25 (dd, 1H), 6.00 (s, 2H), 4.80 (m, 1H), 3.80–3.65 (m, 2H), 3.60–3.50 (m, 2H), 3.20 (q, 2H), 2.25 (s, 3H), 2.10–2.00 (m, 2H), 1.80–1.65 (m, 2H), 1.25 (t, 3H);

1-(4-amidinonaphth-1-yl)methyl-2-ethyl-5-(N-(1-iminoethyl)piperidin-4-yloxy)benzimidazole, $^1$H NMR (300 MHz, DMSO) δ 9.40 (s, 2H), 9.20 (s, 2H), 9.18 (s, 1H), 8.60 (s, 1H), 8.40 (s, 1H), 8.15 (d, 1H), 8.10 (d, 1H), 7.90 (s, 1H), 7.85 (d, 2H), 7.65 (d, 1H), 7.40 (s, 1H), 7.20 (dd, 1H), 6.00 (s, 2H), 4.80 (m, 1H), 3.80–3.65 (m, 2H), 3.60–3.50 (m, 2H), 3.25 (q, 2H), 2.30 (s, 3H), 2.10–2.00 (m, 2H), 1.90–1.70 (m, 2H), 1.40 (t, 3H);

1-(4-amidinonaphth-1-yl)methyl-2-t-butyl-6-(N-(1-iminoethyl)piperidin-4-yloxy)benzimidazole, $^1$H NMR (500 MHz, DMSO) δ 9.40 (s, 2H), 9.20 (s, 2H), 9.18 (s, 1H), 8.60 (s, 1H), 8.40 (s, 1H), 8.18 (d, 1H), 8.10 (d, 1H), 7.80–7.77 (m, 2H), 7.70 (d, 1H), 7.59 (s, 1H), 7.25–7.20 (m, 2H), 6.00 (s, 2H), 4.60 (m, 1H), 3.70–3.60 (m, 2H), 3.50–3.40 (m, 2H), 2.30 (s, 3H), 2.00–1.90 (m, 2H), 1.75–1.60 (m, 2H), 1.48 (s, 9H);

1-(4-amidinonaphth-1-yl)methyl-2-t-butyl-5-(N-(1-iminoethyl)piperidin-4-yloxy)benzimidazole, $^1$H NMR (500 MHz, DMSO) δ 9.40 (s, 2H), 9.10 (m, 3H), 8.60 (s, 1H), 8.30 (s, 1H), 8.18 (d, 1H), 8.10 (d, 1H), 7.80 (d, 1H), 7.70–7.60 (m, 2H), 7.45 (d, 1H), 7.40 (s, 1H), 7.20 (d, 1H), 6.00 (s, 2H), 4.60 (m, 1H), 3.80–3.70 (m, 2H), 3.60–3.50 (m, 2H), 2.30 (s, 3H), 2.20–2.00 (m, 2H), 1.90–1.60 (m, 2H), 1.60 (s, 9H);

1-(4-amidinonaphth-1-yl)methyl-6-(N-(1-iminoethyl)piperidin-4-yloxy)benzimidazole, 1H NMR (300 MHz, DMSO) δ 9.70 (s, 1H), 9.45 (s, 2H), 9.30 (s, 2H), 9.20 (s, 1H), 8.60 (s, 1H), 8.40 (s, 1H), 8.25–8.18 (m, 2H), 8.10 (s, 1H), 7.90–7.80 (m, 3H), 7.60 (s, 1H), 7.30 (dd, 1H), 6.00 (s, 2H), 4.80 (m, 1H), 3.85–3.70 (m, 2H), 3.60–3.50 (m, 2H), 2.35 (s, 3H), 2.15–2.05 (m, 2H), 1.95–1.85 (m, 2H);

1-(4-amidinonaphth-1-yl)methyl-5-(N-(1-iminoethyl)piperidin-4-yloxy)benzimidazole, $^1$H NMR (300 MHz, DMSO) δ 9.80 (s, 1H), 9.40 (s, 2H), 9.20 (s, 2H), 9.10 (s, 1H) 8.60 (s, 1H), 8.40 (s, 1H), 8.15–8.00 (m, 3H), 7.90–7.75 (m, 3H), 7.45 (s, 1H), 7.20 (dd, 1H), 6.00 (s, 2H), 4.80 (m, 1H), 3.80–3.70 (m, 2H), 3.60–3.45 (m, 2H), 2.30 (s, 3H), 2.20–2.00 (m, 2H), 1.90–1.70 (m, 2H);

1-(4-amidinonaphth-1-yl)methyl-2-propyl-6-(N-(1-iminoethyl)piperidin-4-yloxy)benzimidazole, $^1$H NMR (300 MHz, DMSO) δ 9.40 (s, 2H), 9.20 (s, 2H), 9.18 (s, 1H), 8.60 (s, 1H), 8.40 (s, 1H), 8.18 (d, 1H), 8.14 (d, 1H), 7.90–7.80 (m, 3H), 7.65 (d, 1H), 7.60 (s, 1H), 7.25 (dd, 1H), 6.00 (s, 2H), 4.80 (m, 1H), 3.80–3.65 (m, 2H), 3.60–3.40 (m, 2H), 3.20 (t, 2H), 2.30 (s, 3H), 2.18–2.00 (m, 2H), 1.85–1.70 (m, 4H), 0.90 (t, 3H);

1-(4-amidinonaphth-1-yl)methyl-2-propyl-5-(N-(1-iminoethyl)piperidin-4-yloxy)benzimidazole, $^1$H NMR (300 MHz, DMSO) δ 9.40 (s, 2H), 9.20 (s, 2H), 9.18 (s, 1H), 8.60 (s, 1H), 8.40 (s, 1H), 8.15 (d, 1H), 8.10 (d, 1H), 7.90 (s, 1H), 7.80 (d, 1H), 7.70 (d, 1H), 7.63 (s, 1H), 7.40 (s, 1H), 7.20 (dd, 1H), 6.00 (s, 2H), 4.80 (m, 1H), 3.80–3.65 (m, 2H), 3.62–3.50 (m, 2H), 3.23 (t, 2H), 2.30 (s, 3H), 2.20–2.00 (m, 2H), 1.85–1.70 (m, 4H), 1.00 (t, 3H);

1-(4-amidinonaphth-1-yl)methyl-2-sec-butyl-6-(N-(1-iminoethyl)piperidin-4-yloxy)benzimidazole, $^1$H NMR (300 MHz, DMSO) δ 9.40 (s, 2H), 9.20 (s, 2H), 9.18 (s, 1H), 8.60 (s, 1H), 8.40 (s, 1H), 8.18 (d, 1H), 8.10 (d, 1H), 7.90–7.77 (m, 3H), 7.65 (d, 1H), 7.59 (s, 1H), 7.25 (dd, 1H), 6.00 (s, 2H), 4.80 (m, 1H), 3.80–3.70 (m, 2H), 3.60–3.50 (m, 2H), 3.10 (d, 2H), 2.30 (s, 3H), 2.18–2.00 (m, 3H), 1.85–1.70 (m, 2H), 0.90 (d, 6H);

1-(4-amidinonaphth-1-yl)methyl-2-sec-butyl-5-(N-(1-iminoethyl)piperidin-4-yloxy)benzimidazole, $^1$H NMR (300 MHz, DMSO) δ 9.40 (s, 2H), 9.20 (s, 2H), 9.18 (s, 1H), 8.60 (s, 1H), 8.40 (s, 1H), 8.18 (d, 1H), 8.10 (d, 1H), 7.90 (s, 1H), 7.85 (d, 1H), 7.70 (d, 1H), 7.60 (d, 1H), 7.45 (s, 1H), 7.20 (d, 1H), 6.00 (s, 2H), 4.80 (m, 1H), 3.80–3.70 (m, 2H), 3.60–3.50 (m, 2H), 3.10 (d, 2H), 2.30 (s, 3H), 2.18–2.00 (m, 3H), 1.85–1.70 (m, 2H), 0.95 (d, 6H);

1-(4-amidinonaphth-1-yl)methyl-2-n-butyl-6-(N-(1-iminoethyl)piperidin-4-yloxy)benzimidazole, $^1$H NMR (300 MHz, DMSO) δ 9.40 (s, 2H), 9.20 (s, 2H), 9.18 (s, 1H), 8.60 (s, 1H), 8.40 (s, 1H), 8.18 (d, 1H), 8.10 (d, 1H), 7.90–7.80 (m, 3H), 7.70–7.60 (m, 2H), 7.25 (dd, 1H), 6.00 (s, 2H), 4.80 (m, 1H), 3.80–3.70 (m, 2H), 3.60–3.50 (m, 2H), 3.20 (t, 2H), 2.30 (s, 3H), 2.18–2.00 (m, 2H), 1.85–1.60 (m, 4H), 1.40 (m, 2H), 0.90 (t, 3H);

1-(4-amidinonaphth-1-yl)methyl-2-n-butyl-5-(N-(1-iminoethyl)piperidin-4-yloxy)benzimidazole, $^1$H NMR (300 MHz, DMSO) δ 9.40 (s, 2H), 9.20 (s, 2H), 9.18 (s, 1H), 8.60 (s, 1H), 8.40 (s, 1H), 8.18 (d, 1H), 8.10 (d, 1H), 7.90 (s, 1H), 7.83 (d, 1H), 7.75 (d, 1H), 7.60 (d, 1H), 7.40 (s, 1H), 7.20 (d, 1H), 6.00 (s, 2H), 4.80 (m, 1H), 3.80–3.70 (m, 2H), 3.60–3.50 (m, 2H), 3.25 (t, 2H), 2.30 (s, 3H), 2.18–2.00 (m, 2H), 1.85–1.65 (m, 4H), 1.40 (m, 2H), 0.95 (t, 3H);

1-(4-amidinonaphth-1-yl)methyl-2-(2-carboxyethyl)-6-(N-(1-iminoethyl)piperidin-4-yloxy)benzimidazole, $^1$H-NMR 9.45 (s, 2H), 9.39 (s, 2H), 9.20 (s, 1H), 8.60 (s, 1H), 8.40 (s, 1H), 8.10 (dd, 2H), 7.80 ( d, 1H), 7.70 (dd, 3H), 7.45 (s, 1H), 7.10 (d, 1H), 5.90 (s, 2H), 4.70 (m, 1H), 3.70 (m, 2H), 3.50 (m, 2H), 3.30 (t, 2H), 3.10 (m, 1H), 2.90 (t, 2H), 2.30 (s, 3H), 2.10 (m, 2H), 1.75 (m, 2H);

1-(4-amidinonaphth-1-yl)methyl-2-(2-carboxyethyl)-5-(N-(1-iminoethyl)piperidin-4-yloxy)benzimidazole, $^1$H-NMR 9.45 (s, 2H), 9.40 (s, 2H), 9.20 (s, 1H), 8.85 (s, 1H), 8.40 (s, 1H), 8.10 (dd, 2H), 7.80 (m, 2H), 7.65 (dd, 2H), 7.40 (s, 1H), 7.10 (d, 1H), 5.95 (s, 2H), 4.85 (m, 1H), 3.80 (m, 2H), 3.50 (m, 2H), 3.25 (m, 2H), 3.10 (m, 1H), 2.95 (m, 2H), 2.30 (s, 3H), 2.10 (m, 2H), 1.75 (m, 2H);

1-(4-amidinonaphth-1-yl)methyl-2-(2-aminocarbonylethyl)-6-(N-(1-iminoethyl)piperidin-4-yloxy)benzimidazole, $^1$H-NMR 9.42 (s, 2H), 9.35 (s, 2H), 9.20 (s, 1H), 8.60 (s, 1H), 8.40 (s, 1H), 8.10 (dd, 2H), 7.85 (d, 1H), 7.70 (m, 3H), 7.50 (s, 1H), 7.45 (s, 1H), 7.10 (d, 1H), 7.00 (s, 1H), 5.90 (s, 2H), 4.70 (m, 1H), 3.70 (m, 2H), 3.50 (m, 2H), 3.20 (m, 3H), 2.80 (t, 2H), 2.00 (m, 2H), 1.70 (m, 2H);

1-(4-amidinonaphth-1-yl)methyl-2-methyl-6-(N-(N'-(1-iminoethyl)piperidin-4-yl)-N-((methoxycarbonyl)methyl)amino)benzimidazole, $^1$H NMR (300 MHz, DMSO) δ 1.70 (m, 4H), 2.25 (s, 3H), 2.80 (s, 3H), 3.20 (m, 2H), 3.50 (s, 3H), 3.90 (m, 1H), 4.10 (m, 2H), 4.15 (s, 2H). 5.90 (s, 2H), 7.00 (s, 1H), 7.05 (d, 1H), 7.60 (d, 1H), 7.70 (d, 1H), 7.80 (d, 1H), 7.90 (s, 1H), 8.10 (d, 1H), 8.15 (d, 1H), 8.40 (s, 1H), 8.50 (s, 1H), 9.10 (s, 1H), 9.15 (s, 2H), 9.40 (s, 2H);

1-(4-amidinonaphth-1-yl)methyl-2-methyl-6-(N-(N'-(1-iminoethyl)piperidin-4-yl)-N-((aminocarbonyl)methyl)amino)benzimidazole, $^1$H NMR (300 MHz, DMSO) δ 1.80 (m, 4H), 2.25 (s, 3H), 2.80 (s, 3H), 3.25 (m, 2H), 3.80 (s, 2H), 3.95 (m, 1H), 4.15 (m, 2H), 5.90 (s, 2H), 7.00 (d, 1H), 7.10 (s, 1H), 7.40 (br s, 1H), 7.60 (d, 1H), 7.70 (d, 1H), 7.83 (d, 1H), 7.95 (s, 1H), 8.10 (d, 1H), 8.15 (d, 1H), 8.40 (s, 1H), 8.55 (s, 1H), 9.10 (s, 1H), 9.15 (s, 2H), 9.40 (s, 2H);

1-(4-amidinonaphth-1-yl)methyl-2-methyl-6-(N-(N'-(1-iminoethyl)piperidin-4-yl)-N-(3-carboxypropyl)amino)benzimidazole, $^1$H NMR (300 MHz, DMSO) δ 1.60 (m, 2H), 1.80 (m, 4H), 2.20 (m, 2H), 2.25 (s, 3H), 2.80 (s, 3H), 3.20 (m, 4H), 3.95 (m, 1H), 4.10 (m, 2H), 5.90 (s, 2H), 7.15 (m, 1H), 7.65 (d, 1H), 7.70 (d, 1H), 7.80 (d, 1H), 7.95 (s, 1H), 8.10 (d, 1H), 8.15 (d, 1H), 8.40 (s, 1H), 8.58 (s, 1H), 9.10 (m, 3H), 9.20 (s, 2H);

1-(4-amidinonaphth-1-yl)methyl-2-methyl-6-(N-(N'-(1-iminoethyl)piperidin-4-yl)-N-(2-(methoxycarbonyl)propyl)amino)benzimidazole, $^1$H NMR (300 MHz, DMSO) δ 0.80 (d, 3H), 1.60 (m, 4H), 2.20 (s, 3H), 2.40 (m, 1H), 2.80 (s, 3H), 3.10 (m, 3H), 3.30 (m, 1H), 3.40 (s, 3H), 3.90 (m, 2H), 4.05 (m, 1H), 5.85 (d, 1H), 5.90 (d, 1H), 7.10 (d, 1H), 7.20 (d, 1H), 7.60 (d, 1H), 7.65 (d, 1H), 7.80 (d, 1H), 7.90 (s, 1H), 8.05 (d, 1H), 8.10 (d, 1H), 8.35 (s, 1H), 8.50 (m, 1H), 9.05 (br s, 1H), 9.10 (s, 2H), 9.40 (s, 2H);

1-(4-amidinonaphth-1-yl)methyl-2-methyl-6-(N-(N'-(1-iminoethyl)piperidin-4-yl)-N-(2-(carboxy)propyl)amino)benzimidazole, $^1$H NMR (300 MHz, DMSO) δ 0.85 (d, 3H), 1.70 (m, 4H), 2.20 (s, 3H), 2.30 (m, 1H), 2.85 (s, 3H), 3.10 (m, 3H), 3.40 (m, 1H), 3.90 (m, 2H), 4.10 (m, 1H), 5.85 (d, 1H), 5.90 (d, 1H), 7.15 (d, 1H), 7.15 (d, 1H), 7.60 (d, 1H), 7.65 (d, 1H), 7.80 (d, 1H), 7.95 (s, 1H), 8.05 (d, 1H), 8.10 (d, 1H), 8.40 (s, 1H), 8.50 (s, 1H), 9.05 (br s, 1H), 9.10 (s, 2H), 9.40 (s, 2H);

1-(4-amidinonaphth-1-yl)methyl-2-methyl-5-(N-(N'-(1-iminoethyl)piperidin-4-yl)-N-(2-(carboxy)propyl)amino)benzimidazole, $^1$H NMR (300 MHz, DMSO) δ 1.00 (d, 3H), 1.70 (m, 4H), 2.20 (s, 3H), 2.50 (m, 1H), 2.90 (s, 3H), 3.10 (m, 3H), 3.40 (m, 1H), 3.90 (m, 2H), 4.10 (m, 1H), 5.85 (s, 2H), 7.15 (d, 1H), 7.20 (d, 1H), 7.55 (d, 1H), 7.60 (d, 1H), 7.80 (d, 1H), 7.95 (s, 1H), 8.00 (d, 1H), 8.05 (d, 1H), 8.40 (s, 1H), 8.50 (s, 1H), 9.05 (br s, 1H), 9.10 (s, 2H), 9.40 (s, 2H);

1-(4-amidinonaphth-1-yl)methyl-2-methyl-5-hydroxy-6-(N-(1-iminoethyl)piperidin-4-yloxy)benzimidazole, $^1$H NMR (DMSO, 300 MHz) δ 9.50 (s, 4H), 9.20 (s, 1H), 8.65 (s, 1H), 8.40–7.20 (m, 9H), 5.92 (s, 1H), 5.88 (s, 1H), 4.80 (m, 0.5H), 4.70 (m, 0.5H), 3.80–3.45 (m, 4H), 2.90 (s, 1.5H), 2.80 (s, 1.5H), 2.30 (s, 3H), 2.10–1.70 (m, 4H) (a mixture of two regioisomers);

1-(4-amidinonaphth-1-yl)methyl-2-methyl-5-(aminocarbonyl)methoxy-6-(N-(1-iminoethyl)piperidin-4-yloxy)benzimidazole, $^1$H NMR (DMSO, 300 MHz) δ 9.46 (s, 4H), 9.21 (s, 1H), 8.70 (s, 1H), 8.40–7.38 (m, 10H), 5.92 (s, 1H), 5.88 (s, 1H), 4.82 (m, 0.5H), 4.76 (m, 0.5H), 4.62 (s, 1H), 4.52 (s, 1H), 3.80–3.40 (m, 4H), 2.80 (s, 1.5H), 2.78 (s, 1.5H), 2.25 (s, 1.5H), 2.23 (s, 1.5H), 2.16–1.75 (m, 4H) (a mixture of two regioisomers);

1-(4-amidinonaphth-1-yl)methyl-2-methyl-5-(carboxy)methoxy-6-(N-(1-iminoethyl)piperidin-4-yloxy)benzimidazole, $^1$H NMR (DMSO, 300 MHz) δ 9.60 (s, 2H), 9.50 (s, 2H), 9.20 (s, 1H), 8.70 (s, 1H), 8.40–7.40 (m, 9H), 5.96 (s, 2H), 4.90 (s, 1H), 4.80 (s, 1H), 4.70 (m, 1H), 3.80–3.50 (m, 4H), 2.80 (s, 3H), 2.30 (s, 3H), 2.15–1.70 (m, 4H) (a mixture of regioisomers);

1-(4-amidinonaphth-1-yl)methyl-2-methyl-5-(4-(methoxycarbonyl)benzyloxy)-6-(N-(1-iminoethyl)piperidin-4-yloxy)benzimidazole, $^1$H NMR (DMSO, 300 MHz) δ 9.42 (s, 2H), 9.30 (s, 2H), 9.18 (s, 1H), 8.60 (s, 1H), 8.40–7.40 (m, 12H), 5.90 (s, 2H), 5.35 (s, 2H), 4.70 (m, 1H), 3.90 (s, 3H), 3.80–3.40 (m 4H), 2.70 (s, 3H), 2.30 (s, 3H), 2.10–1.70 (m, 4H);

1-(4-amidinonaphth-1-yl)methyl-2-methyl-5-(4-(carboxy)benzyloxy)-6-(N-(1-iminoethyl)piperidin-4-yloxy)benzimidazole, $^1$H NMR (DMSO, 300 MHz) δ 9.42 (s,2H), 9.30 (s,2H), 9.18 (s,1H), 8.60 (s, 1H), 8.18–7.40 (m, 12H), 5.90 (s, 2H), 5.30 (s, 2H), 4.70 (m, 1H), 3.80–3.40 (m, 4H), 2.70 (s, 3H), 2.30 (s, 3H), 2.10–1.70 (m, 4H);

1-(4-amidinonaphth-1-yl)methyl-2-methyl-5-carboxy-6-(N-(1-iminoethyl)piperidin-4-yloxy)benzimidazole, $^1$H NMR (DMSO, 300 MHz) δ 9.40 (s, 4H), 9.20 (s, 1H), 8.63 (s,1H), 8.40–7.60 (m, 9H), 6.00 (s, 2H), 4.90 (m, 1H), 3.70 (m, 4H), 2.70 (s, 3H), 2.30 (s, 3H), 2.05–1.80 (m, 4H);

1-(4-amidinonaphth-1-yl)methyl-2-methyl-5-(carboxy)methoxy-6-(N-(1-iminoethyl)piperidin-4-yloxy)benzimidazole, 1-(4-amidinonaphth-1-yl)methyl-2-methyl-5-((aminocarbonyl)methoxy-6-(N-(1-iminoethyl)piperidin-4-yloxy)benzimidazole, $^1$H NMR (DMSO, 300 MHz) δ 9.60 (s, 2H), 9.30 (s, 2H), 9.12 (s, 1H), 8.60 (s, 1H), 8.40–7.30 (m, 10H), 5.90 (s, 2H), 4.70 (m, 1H), 4.60 (s, 2H), 3.80–3.40 (m, 4H), 2.70 (s, 3H), 2.30 (s, 3H), 2.12–1.80 (m, 4H);

1-(4-amidinonaphth-1-yl)methyl-2-methyl-5-(3-(methoxycarbonyl)benzyloxy)-6-(N-(1-iminoethyl)piperidin-4-yloxy)benzimidazole, $^1$H NMR (DMSO, 300 MHz) δ 9.65 (s, 2H), 9.30 (s, 2H), 9.16 (s, 1H), 8.60 (s, 1H), 8.40–7.40 (m, 12H), 5.90 (s, 2H), 5.30 (s, 2H), 4.70 (m, 1H), 3.90 (s, 3H), 3.80–3.40 (m, 4H), 2.70 (s, 3H), 2.36 (s, 3H), 2.20–1.80 (m, 4H);

1-(4-amidinonaphth-1-yl)methyl-2-methyl-5-(3-(carboxy)benzyloxy)-6-(N-(1-iminoethyl)piperidin-4-yloxy)benzimidazole, $^1$H NMR (DMSO, 300 MHz) δ 9.40 (s, 2H), 9.10 (s, 1H), 9.05 (s, 2H), 8.60 (s, 1H), 8.40–7.40 (m, 12H), 5.90 (s, 2H), 5.35 (s, 2H), 4.70 (m, 1H), 3.80–3.45 (m, 4H), 2.70 (s, 3H), 2.25 (s, 3H), 2.05–1.70 (m, 4H);

1-(4-amidinonaphth-1-yl)methyl-2-methyl-5-(methoxycarbonyl)methoxy-6-(N-(1-iminoethyl)piperidin-4-yloxy)benzimidazole, $^1$H NMR (DMSO, 300 MHz) δ 9.45 (s, 2H), 9.10 (s, 3H), 8.60 (s, 1H), 8.40–7.40 (m, 8H), 5.90 (s, 2H), 5.00 (s, 2H), 4.70 (m, 1H), 3.70 (s, 3H), 3.60 (m, 4H), 2.80 (s, 3H), 2.30 (s, 3H), 2.10–1.80 (m, 4H);

1-(4-amidinonaphth-1-yl)methyl-2-methyl-5-(1-(aminocarbonyl)ethoxy)-6-(N-(1-iminoethyl)piperidin-4-yloxy)benzimidazole, $^1$H NMR (DMSO, 300 MHz) δ 9.40 (s, 2H), 9.20 (s, 3H), 8.60 (s, 1H), 8.40–7.30 (m, 10H), 5.95 (s, 2H,), 4.70 (m, 2H), 3.80–3.50 (m, 4H), 2.80 (s, 3H), 2.30 (s, 3H), 2.10–1.80 (m, 4H), 1.50 (d, 3H);

1-(4-amidinonaphth-1-yl)methyl-2-methyl-5-(1-(methoxycarbonyl)ethoxy)-6-(N-(1-iminoethyl)piperidin-4-yloxy)benzimidazole, $^1$H NMR (DMSO, 300 MHz) δ 9.45 (s, 2H), 9.30 (s, 2H), 9.20 (s, 1H), 8.60 (s, 1H), 8.40–7.35 (m, 8H), 5.90 (s, 2H), 5.10 (m, 1H), 4.70 (m, 1H), 3.90 (s, 3H), 3.70 (m, 4H), 2.76 (s, 3H), 2.30 (s, 3H), 2.10–1.80 (m, 4H), 1.60 (d, 3H);

1-(4-amidinonaphth-1-yl)methyl-2-methyl-5-(1-(carboxy)ethoxy)-6-(N-(1-iminoethyl)piperidin-4-yloxy)benzimidazole, $^1$H NMR (DMSO, 300 MHz) δ 9.45 (s, 2H), 9.35 (s, 2H), 9.18 (s, 1H), 8.60 (s, 1H), 8.40–7.30 (m, 8H), 5.96 (s, 2H), 5.00 (m, 1H), 4.70 (m, 1H), 3.60 (m, 4H), 2.78 (s, 3H), 2.30 (s, 3H), 2.10–1.80 (m, 4H), 1.60 (d, 3H);

1-(4-amidinonaphth-1-yl)methyl-2-isopropyl-4-methoxy-6-(N-(1-iminoethyl)piperidin-4-yloxy)benzimidazole, $^1$H NMR (300 MHz, DMSO) δ 9.40 (s, 2H), 9.20 (s, 2H), 9.18 (s, 1H), 8.60 (s, 1H), 8.40 (s, 1H), 8.18 (d, 1H), 8.14 (d, 1H), 7.85 (d, 1H), 7.75 (s, 1H), 7.60 (d, 1H), 7.25 (s, 1H), 6.80 (s, 1H), 6.00 (s, 2H), 4.80 (m, 1H), 4.10 (s, 3H), 3.80–3.65 (m, 2H), 3.60–3.45 (m, 3H), 2.30 (s, 3H), 2.18–2.00 (m, 2H), 1.90–1.80 (m, 2H), 1.35 (d, 6H);

1-(4-amidinonaphth-1-yl)methyl-2-isopropyl-7-methoxy-5-(N-(1-iminoethyl)piperidin-4-yloxy)benzimidazole, $^1$H NMR (300 MHz, DMSO) δ 9.40 (s, 2H), 9.20 (s, 3H), 8.60 (br s, 1H), 8.40 (s, 1H), 8.20–8.10 (m, 3H), 7.90–7.80 (m, 3H), 7.65 (d, 1H), 7.00 (s, 1H), 6.80 (s, 1H), 6.10 (s, 2H), 4.90 (m, 1H), 3.90–3.55 (m, 6H), 2.35 (s, 3H), 2.20–2.10 (m, 2H), 2.00–1.80 (m, 2H), 1.40 (d, 6H);

1-(4-amidinonaphth-1-yl)methyl-2-methyl-5-(N-(4-carboxy)benzylamino)-6-(N-(1-iminoethyl)piperidin-4-yloxy)benzimidazole, (approx 1:1 mixture of regioisomers) $^1$H NMR (300 MHz, DMSO) δ 1.85 (m, 2H), 2.00 (m, 2H), 2.25 (s, 3H), 2.60 (s, 1.5H), 2.75 (s, 1.5H), 3.60 (m, 2H), 3.80 (m, 2H), 4.40 (s, 1H), 4.50 (s, 1H), 4.80 (m, 0.5H), 4.90 (m, 0.5H), 5.65 (s, 1H), 5.85 (s, 1H), 6.50 (s, 0.5H), 6.60 (s, 0.5H), 7.25 (d, 1H), 7.30 (s, 1H), 7.40 (m, 1H), 7.50 (s, 0.5H), 7.60 (d, 1H), 7.70 (d, 1H), 7.75 (d, 1H), 7.85 (d, 0.5H), 7.90 (d, 1H), 8.00 (d, 1H), 8.05 (d, 1H), 8.10 (d, 1H), 8.35 (d, 1H), 8.60 (s, 1H), 9.10 (s, 2H), 9.15 (s, 1H), 9.35 (s, 2H);

1-(4-amidinonaphth-1-yl)methyl-2-isopropyl-4-(4-carboxypiperidin-1-yl)-6-(N-(1-iminoethyl)piperidin-4-yloxy)benzimidazole, $^1$H-NMR 9.38 (s, 2H), 9.05 (s, 3H), 8.50 (s, 1H), 8.38 (s, 1H), 8.05 (dd, 2H), 7.80 (d, 1H), 7.70 (s, 1H), 7.58 (d, 1H), 7.25 (s, 1H), 6.70 (s, 1H), 5.95 (s, 2H), 4.70 (m, 1H), 3.65 (m, 2H), 3.50 (m, 4H), 2.85 (t, 2H), 2.40 (m, 2H), 2.20 (s, 3H), 1.95 (m, 5H), 1.70 (m, 2H), 1.30 (d, 6H);

1-(4-amidinonaphth-1-yl)methyl-2-isopropyl-4-(carboxy)methoxy-6-(N-(1-iminoethyl)piperidin-4-yloxy)benzimidazole, $^1$H-NMR 9.38 (s, 2H), 9.05 (s, 2H), 8.75 (s, 1H), 8,40 (s, 1H), 8.05 (dd, 2H), 7,80 (d, 1H), 7.70 (s, 1H), 7.60 (d, 1H), 7.25 (s, 1H), 6.75 (s, 1H), 5.95 (s, 2H), 5.00 (s, 2H), 4.70 (m, 1H), 3.80–3.40 (m, 5H), 2.20 (s, 3H), 2.00 (m, 2H), 1.85 (m, 2H), 1.30 (d, 6H);

1-(4-amidinonaphth-1-yl)methyl-2-isopropyl-7-nitro-6-(N-(1-iminoethyl)piperidin-4-yloxy)benzimidazole, $^1$H-NMR 9.38 (s, 2H), 9.15 (s, 1H), 9.05 (s, 2H), 8.80 (s, 1H), 8.35 (s, 1H), 8.10 (d, 1H), 8.05 (d, 1H), 7.95 (d, 1H), 7.80 (d, 1H), 7.70 (s, 1H), 7.60 (d, 1H), 7.50 (d, 1H), 5.95 (s, 2H), 5.00 ( m, 1H), 3.60–3.45 (m, 5H), 2.25 (s, 3H), 2.00 (m, 2H), 1.30 (d, 6H), 1.30 (d, 6H);

1-(4-amidinonaphth-1-yl)methyl-2-methyl-7-nitro-6-(N-(1-iminoethyl)piperidin-4-yloxy)benzimidazole, $^1$H NMR (DMSO, 300 MHz) δ 9.45 (s, 2H), 9.38 (s, 2H), 9.20 (s, 1H), 8.65 (s, 1H), 8.42–7.30 (m, 8H), 5.81 (s, 2H), 4.90 (m, 1H), 3.60 (m, 4H), 2.60 (s, 3H), 2.23 (s, 3H), 2.10 (m, 2H), 1.80 (m, 2H);

1-(4-amidinonaphth-1-yl)methyl-2-isopropyl-5-(N-(2-carboxyprop-2-yl)amino)-6-(N-(1-iminoethyl)piperidin-4-yloxy)benzimidazole, $^1$H NMR (300 MHz, DMSO) δ 1.25 (d, 6H), 1.55 (s, 6H), 1.80 (m, 2H), 2.00 (m, 2H), 2.25 (s, 3H), 3.50 (m, 3H), 3.70 (m, 2H), 4.80 (m, 1H), 5.95 (s, 2H), 6.70 (s, 1H), 7.60 (m, 1H), 7.70 (s, 1H), 7.80 (d, 1H), 8.05 (d, 1H), 8.10 (d, 1H), 8.40 (s, 1H), 8.60 (s, 1H), 9.10 (s, 2H), 9.15 (s, 1H), 9.40 (s, 2H);

1-(4-amidinonaphth-1-yl)methyl-2-isopropyl-5-(N-(4-carboxy)benzylamino)-6-(N-(1-iminoethyl)piperidin-4-yloxy)benzimidazole, $^1$H NMR (300 MHz, DMSO) δ 1.20 (d, 6H), 1.90 (m, 2H), 2.00 (m, 2H), 2.20 (s, 3H), 3.45 (sept, 1H), 3.60 (m, 2H), 3.80 (m, 2H), 4.55 (s, 2H), 4.93 (m, 1H), 5.95 (s, 2H), 6.45 (s, 1H), 7.45 (d, 2H), 7.57 (s, 1H), 7.60 (d, 1H), 7.65 (s, 1H), 7.80 (d, 1H), 7.90 (d, 2H), 8.05 (d, 1H), 8.10 (d, 1H), 8.37 (s, 1H), 8.60 (s, 1H), 9.10 (s, 2H), 9.15 (s, 1H), 9.18 (s, 2H);

1-(4-amidinonaphth-1-yl)methyl-2-isopropyl-5-(N-(2-carboxyethyl)amino)-6-(N-(1-iminoethyl)piperidin-4-yloxy)benzimidazole, $^1$H NMR (300 MHz, DMSO) δ 1.20 (d, 6H), 1.80 (m, 2H), 1.95 (m, 2H), 2.20 (s, 3H), 2.55 (m, 2H), 3.40 (m, 2H), 3.50 (m, 3H), 3.70 (m, 2H), 4.80 (m, 1H), 5.95 (s, 2H), 6.85 (s, 1H), 7.50 (m, 2H), 7.65 (s, 1H), 7.75 (d, 1H), 8.00 (d, 1H), 8.05 (d, 1H), 8.30 (s, 1H), 8.50 (s, 1H), 9.10 (s, 3H), 9.30 (s, 2H);

1-(4-amidinonaphth-1-yl)methyl-2-methyl-5-(N-(carboxymethyl)piperidin-4-yloxy)-6-(N-(1-iminoethyl)piperidin-4-yloxy)benzimidazole, $^1$H NMR (DMSO, 300 MHz) δ 10.40 (s, 1H), 9.70 (s, 2H), 9.45 (s, 3H), 8.98 (s, 1H), 8.70–7.80 (m, 8H), 6.24 (s, 2H), 5.00 (m, 2H), 4.48 (s, 2H), 4.0–3.40 (m, 8H), 3.20 (s, 3H), 2.60 (s, 3H), 2.40–2.00 (m, 8H);

1-(4-amidinonaphth-1-yl)methyl-6-(N-(N'-(1-iminoethyl)piperidin-4-yl)-N-((4-methoxycarbonyl)benzyl)amino)benzimidazole, 1-(4-amidinonaphth-1-yl)methyl-6-(N-(N'-(1-iminoethyl)piperidin-4-yl)-N-((4-carboxy)benzyl)amino)benzimidazole, 1-(4-amidinonaphth-1-yl)methyl-2-trifluoromethyl-6-(N-(1-iminoethyl)piperidin-4-yloxy)benzimidazole, $^1$H NMR (300 MHz, DMSO) δ 9.40 (s, 2H), 9.20–9.15 (m, 3H), 8.60 (s, 1H), 8.45 (s, 1H), 8.20–8.10 (m, 3H), 8.00 (d, 1H), 7.80 (d, 2H), 7.43 (s, 1H), 7.20 (d, 1H), 5.40 (s, 2H), 4.85–4.75 (m, 1H), 4.20 (dd, 2H), 3.60–3.40 (dt, 2H), 2.80–2.60 (m, 2H, obscured by DMSO signal), 2.40 (s, 3H), 2.15–2.00 (m, 2H);

1-(4-amidinonaphth-1-yl)methyl-6-(N-(N'-(1-iminoethyl)piperidin-4-yl)-N-((2-(ethoxycarbonyl)ethyl)carbonyl)amino)benzimidazole, and 1-(4-amidinonaphth-1-yl)methyl-6-(N-(N'-(1-iminoethyl)piperidin-4-yl)-N-((2-(carboxy)ethyl)carbonyl)amino)benzimidazole.

EXAMPLE 3

Compounds of formula (Ic)

To a mixture of 1-(4-cyanonaphth-1-yl)methyl-2-isopropyl-4-methoxycarbonyl-6-(N-(tert-butoxycarbonyl)piperidin-4-ylamino)benzimidazole, 1-(4-cyanonaphth-1-yl)methyl-2-isopropyl-7-methoxycarbonyl-5-(N-(tert-butoxycarbonyl)piperidin-4-ylaminobenzimidazole, and 2-isopropyl-4-methoxycarbonyl-6-(N-(tert-butoxycarbonyl)piperidin-4-yl)((4-cyanonaphth-1-yl)methyl)aminobenzimidazole [4 g, 50% 1-(4-cyanonaphth-1-yl)methyl-2-isopropyl-4-methoxycarbonyl-6-(N-(tert-butoxycarbonyl)piperidin-4-ylamino)benzimidazole] in ethanol (150 mL) cooled in an ice water bath was bubbled HCl (g). After the solution was saturated, the reaction flask was sealed and the temperature maintained at ambient temperature for 16 hours. The solvent was removed under reduced pressure. The residue was dissolved in ethanol (50 mL). The solution was cooled in a dry ice/acetone bath and ammonia (g) was bubbled in. The reaction flask was sealed and then heated at 70° C. for 4 hours. The solvent was removed. The mixture was separated by HPLC on a C18 Dynamax column with a 3–25% acetonitrile in water gradient with 0.1% trifluoroacetic acid to afford 1-(4-amidinonaphth-1-yl)methyl-2-isopropyl-4-aminocarbonyl-6-(piperidin-4-ylamino)-benzimidazole as a white solid after concentration and freeze-drying removal of the solvent.

EXAMPLE 4

Compounds of formulae (Id)

A. To 1-(4-amidinonaphth-1-yl)methyl-2-isopropyl-4-aminocarbonyl-6-(piperidin-4-ylamino)benzimidazole (1 g) in methanol (50 mL) was added triethylamine (3 mL) and ethylacetimidate (1 g). After stirring for 3 hours, the reaction was concentrated. The residue was purified by HPLC on a C18 Dynamax column with a 3–25% acetonitrile in water gradient with 0.1% trifluoroacetic acid to afford 1-(4-amidinonaphth-1-yl)methyl-2-isopropyl-4-aminocarbonyl-6-(N-(1-iminoethyl)piperidin-4-ylamino)benzimidazole, $^1$H NMR (DMSO, 300 MHz) δ 9.70 (s, 2H), 9.58 (s, 2H), 9.40 (s, 1H), 9.35 (s, 1H), 8.82 (s, 1H), 8.62–7.20 (m, 9H), 6.10 (s, 2H), 4.10–3.50 (m, 6H), 2.50 (s, 3H), 2.26 (m, 2H), 1.70 (m, 2H), 1.60 (d, 6H), as white solid after freeze drying removal of the solvent.

B. In a similar manner, the following compound of formula (Id) was made:

1-(4-amidinonaphth-1-yl)methyl-6-(N-(1-iminoethyl) piperidin-4-aminobenzimidazole, $^1$H NMR (300 MHz, DMSO) δ 1.40 (m, 2H), 2.00 (m, 2H), 2.25 (s, 3H), 3.30 (m, 2H), 3.60 (m, 2H), 3.80 (m, 1H), 3.95 (m, 1H), 5.90 (s, 2H), 6.90 (s, 1H), 7.00 (d, 1H), 7.60 (d, 1H), 7.80 (d, 1H), 7.85 (d, 1H), 8.00 (s, 1H), 8.10 (d, 1H), 8.15 (d, 1H), 8.40 (s, 1H), 8.55 (s, 1H), 9.15 (br s, 3H), 9.40 (s, 2H), 9.55 (s, 1H).

EXAMPLE 5

1-(4-Amidinonaphth-1-yl)methyl-2-isopropyl-4-aminocarbonyl-6-(N-(1-iminoethyl)piperidin-4-ylamino) benzimidazole (2 g) was heated at 80° C. in 12N HCl for 12 hours. The solvent was removed under reduced pressure. To the resulting residue in methanol (80 mL) was added triethylamine (10 mL) and ethylacetimidate (2 g). After stirring for 12 hours, the reaction mixture was concentrated. The residue was purified by HPLC on a C18 Dynamax column with a 3–25% acetonitrile in water gradient with 0.1% trifluoroacetic acid to afford 1-(4-amidinonaphth-1-yl) methyl-2-isopropyl-4-carboxy-6-(N-(1-iminoethyl) piperidin-4-ylamino)benzimidazole, $^1$H NMR (DMSO, 300 MHz) δ 9.70 (s, 2H), 9.60 (s, 2H), 9.40 (s, 1H), 8.93 (s, 1H), 8.65–7.40 (m, 8H), 6.30 (s, 2H), 4.20–3.50 (m, 6H), 2.55 (s, 3H), 2.30 (m, 2H), 1.70 (m, 2H), 1.60 (d, 6H), as a white solid after freeze-drying removal of the solvent.

EXAMPLE 6

This example illustrates the preparation of representative pharmaceutical compositions for oral administration containing a compound of the invention, or a pharmaceutically acceptable salt thereof, e.g.,1-(4-amidinonaphth-1-yl) methyl-2-n-butyl-5-(N-(1-iminoethyl)piperidin-4-yloxy) benzimidazole:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of the invention | 20.0% |
| | Magnesium stearate | 0.9% |
| | Starch | 8.6% |
| | Lactose | 79.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of the invention | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 7

This example illustrates the preparation of a representative pharmaceutical formulation for parenteral administration containing a compound of the invention, or a pharmaceutically acceptable salt thereof, e.g., 1-(4-amidinonaphth-1-yl)methyl-2-t-butyl-5-(N-(1-iminoethyl)piperidin-4-yloxy)benzimidazole:

| Ingredients | |
| --- | --- |
| Compound of the invention | 0.02 g |
| Propylene glycol | 20.0 g |
| Polyethylene glycol 400 | 20.0 g |
| Polysorbate 80 | 1.0 g |
| 0.9% saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2μ membrane filter and packaged under sterile conditions.

EXAMPLE 8

This example illustrates the preparation of a representative pharmaceutical composition in suppository form containing a compound of the invention, or a pharmaceutically acceptable salt thereof, e.g., 1-(4-amidinonaphth-1-yl)methyl-2-methyl-6-(N-(N'-(1-iminoethyl)piperidin-4-yl)-N-((aminocarbonyl)methyl)amino)benzimidazole:

| Ingredients | % wt./wt. |
| --- | --- |
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 9

This example illustrates the preparation of a representative pharmaceutical formulation for insufflation containing a compound of the invention, or a pharmaceutically acceptable salt thereof, e.g., 1-(4-amidinonaphth-1-yl)methyl-2-propyl-5-(N-(1-iminoethyl)piperidin-4-yloxy)benzimidazole:

| Ingredients | % wt./wt. |
| --- | --- |
| Micronized compound of the invention | 1.0% |
| Micronized lactose | 99.0% |

The ingredients are milled, mixed, and packaged in an insufflator equipped with a dosing pump.

EXAMPLE 10

This example illustrates the preparation of a representative pharmaceutical formulation in nebulized form containing a compound of the invention, or a pharmaceutically acceptable salt thereof, e.g., 1-(4-amidinonaphth-1-yl)methyl-2-methyl-5-(1-(methoxycarbonyl)ethoxy)-6-(N-(1-iminoethyl)piperidin-4-yloxy)benzimidazole:

| Ingredients | % wt./wt. |
| --- | --- |
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 11

This example illustrates the preparation of a representative pharmaceutical formulation in aerosol form containing a compound of the invention, or a pharmaceutically acceptable salt thereof, e.g., 1-(4-amidinonaphth-1-yl)methyl-2-isopropyl-4-carboxy-6-(N-(1-iminoethyl)piperidin-4-ylamino)benzimidazole:

| Ingredients | % wt./wt. |
| --- | --- |
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 12

(In vitro assay for Factor Xa and Thrombin)

This assay demonstrates the activity of the compounds of the invention towards factor Xa, thrombin and tissue plasminogen activator. The activities were determined as an initial rate of cleavage of the peptide p-nitroanilide by the enzyme. The cleavage product, p-nitroaniline, absorbs at 405 nm with a molar extinction coefficient of $9920 M^{-1} cm^{-1}$.

Reagents and Solutions:
Dimethyl sulfoxide (DMSO) (Baker analyzed grade).
Assay buffer:
  50 mM TrisHCl, 150 mM NaCl, 2.5 mM $CaCl_2$, and 0.1% polyethylene glycol 6000, pH 7.5.
Enzymes (Enzyme Research Lab.):
  1. Human factor Xa stock solution: 0.281 mg/mL in assay buffer, stored at −80° C. (working solution (2X): 106 ng/mL or 2 nM in assay buffer, prepared prior to use).
  2. Human thrombin stock solution: Stored at −80° C. (working solution (2X): 1200 ng/mL or 40 nM in assay buffer, prepare prior to use).
  3. Human tissue plasminogen activator (tPA) (Two chains, Sigma) stock solution: 1 mg/mL, stored at −80° C. (working solution (2X): 1361 ng/mL in assay buffer, prepare prior to use).
Chromogenic substrates (Pharmacia Hepar Inc.):
  1. S2222 (FXa assay) stock solution: 6 mM in $dH_2O$, store at 4° C. (working solution (4X): 656 μM in assay buffer).
  2. S2302 (Thrombin assay) stock solution: 10 mM in $dH_2O$, stored at 4° C. (working solution (4X): 1200 μM in assay buffer).
  3. S2288 (tPA assay) stock solution: 10 mM in $dH_2O$, stored at 4° C. (working solution (4X): 1484 μM in assay buffer). (All substrate working solutions were prepared on assay day 5.)
Standard inhibitor compound stock solution:
  5 mM in DMSO, stored at −20° C.
Test compounds (compounds of the invention) stock solutions:
  10 mM in DMSO, stored at −20° C.
Assay procedure:
  Assays were performed in 96-well microtiter plates in a total volume of 200 μl. Assay conducted in final concentration of 50 mM TrisHCl, 150 mM NaCl, 2.5 mM $CaCl_2$, 0.1% polyethylene glycol 6000, pH 7.5, in the absence or presence of the standard inhibitor or the test compounds and enzyme and substrate at following concentrations: (1) 1 nM factor Xa and 164 μM S2222; (2) 20 nM thrombin and 300 μM S2302; and (3) 10 nM tPA and 371 μM S2288. Concentrations of the standard inhibitor compound in the assay were from 5 μM to 0.021 μM in 1 to 3 dilution. Concentration of the test compounds in the assay typically were from 10 μM to 0.041 μM in 1 to 3 dilution. For potent test compounds, the concentrations used in the factor Xa assay were further diluted 100 fold (100 nM to 0.41 nM) or 1000 fold (10 nM to 0.041 nM). All substrate concentrations used are equal to their $K_m$ values under the present assay conditions. Assays were performed at ambient temperature.

The first step in the assay was the preparation of 10 mM test compound stock solutions in DMSO (for potent test compounds, 10 mM stock solutions were further diluted to 0.1 or 0.01 mM for the factor Xa assay), followed by the preparation of test compound working solutions (4X) by a serial dilutions of 10 mM stock solutions with Biomek 1000 (or Multiprobe 204) in 96 deep well plates as follows:

(a) Prepare a 40 μM working solution by diluting the 10 mM stock 1 to 250 in assay buffer in 2 steps: 1 to 100, and 1 to 2.5.

(b) Make another five serial dilutions (1:3) of the 40 μM solution (600 μl for each concentration). A total of six diluted test compound solutions were used in the assay.

Standard inhibitor compound (5 mM stock) or DMSO (control) went through the same dilution steps as those described above for test compounds.

The next step in the assay was to dispense 50 μl of the test compound working solutions (4X) (from 40 uM to 0.164 uM), in duplicate, to microtiter plates with Biomek or MP204. To this was added 100 μl of enzyme working solution (2X) with Biomek or MP204. The resulting solutions were incubated at ambient temperature for 10 minutes.

To the solutions was added 50 μl of substrate working solution (4X) with Biomek or MP204.

The enzyme kinetics were measured at 405 nm, at 10 seconds interval, for five minutes in a THERMOmax plate reader at ambient temperature.

Calculation of $K_i$ of the test compounds:

Enzyme rates were calculated as mOD/min based on the first two minutes readings. The $IC_{50}$ values were determined by fitting the data to the log-logit equation (linear) or the Morrison equation (non-linear) with an EXCEL spreadsheet. Ki values were then obtained by dividing the $IC_{50}$ by 2. Routinely, Ki(factor Xa) values lower than 3 nM were calculated from the Morrison equation.

Compounds of the invention, when tested in this assay, demonstrated the ability to inhibit human factor Xa and human thrombin.

EXAMPLE 13

(In vitro assay for Human Prothrombinase)

This assay demonstrates the ability of the compounds of the invention to inhibit prothrombinase. Prothrombinase (PTase) catalyzes the activation of prothrombin to yield fragment 1.2 plus thrombin with meizothrombin as the intermediate. This assay is an end point assay. Activity of the prothrombinase is measured by activity of thrombin (one of the reaction products) or by the amount of thrombin formed/time based on a thrombin standard curve (nM vs mOD/min). For determination of $IC_{50}$ (PTase) of the compounds of the invention, PTase activity was expressed by thrombin activity (mOD/min).

Materials:
Enzymes:

1. Human factor Va (Haematologic Technologies Inc., Cat# HCVA-0110) working solution: 1.0 mg/mL in 50% glycerol, 2 mM $CaCl_2$, stored at −20° C.

2. Human factor Xa (Enzyme Res. Lab. cat# HFXa1011) working solution: 0.281 mg/mL in assay buffer (without BSA), stored at −80° C.

3. Human prothrombin (FII) (Enzyme Res. Lab., Cat# HP1002) working solution: Diluted FII to 4.85 mg/mL in assay buffer (without BSA), stored at −80° C.

Phospholipid (PCPS) vesicles:

PCPS vesicles (80%PC, 20%PS) were prepared by modification of the method reported by Barenholz et al., *Biochemistry* (1977), Vol. 16, pp. 2806–2810.

Phosphatidyl serine (Avanti Polar Lipids, Inc., Cat#840032):

10 mg/mL in chloroform, purified from brain, stored −20° C. under nitrogen or argon.

Phosphatidyl Choline (Avanti Polar Lipids, Inc., Cat# 850457):

50 mg/ml in chloroform, synthetic 16:0–18:1 Palmitoyl-Oleoyl, stored at −20° C. under nitrogen or argon.

Spectrozyme-TH (American Diagnostica Inc., Cat# 238L, 50 μmoles, stored at room temperature) working solution: Dissolved 50 μmoles in 10 mL $dH_2O$.

BSA (Sigma Chem Co., Cat# A-7888, FractionV, RIA grade).

Assay buffer: 50 mM TrisHCl, pH 7.5, 150 mM NaCl, 2.5 mM $CaCl_2$, 0.1% PEG 6000 (BDH), 0.05% BSA (Sigma, Fr.V, RIA grade).

For one plate assay, prepare the following working solutions:

1. Prothrombinase complex:

(a) 100 μM PCPS (27.5 μl of PCPS stock (4.36 mM) diluted to final 1200 μl with assay buffer.

(b) 25 nM Human factor Va: 5.08 μl of Va stock (1 mg/mL) was diluted to final 1200 μl with assay buffer.

(c) 5 pM Human factor Xa: Dilute Xa stock (0.281 mg/mL) 1:1,220,000 with assay buffer. Prepare at least 1200 μl.

Combine equal volumes (1100 μl) of each component in the order of PCPS, factor Va and factor Xa. Let stand at ambient temperature for 5 to 10 minutes and use immediately, or store in ice (bring to ambient temperature before use).

2. 6 μM Human prothrombin (FII): dilute 124 μL of FII stock (4.85 mg/mL) to final 1400 μL with assay buffer.

3. 20 mM EDTA/Assay buffer: 0.8 mL of 0.5M EDTA (pH 8.5) plus 19.2 mL assay buffer.

4. 0.2 mM Spectrozyme-TH/EDTA buffer: 0.44 mL of SPTH stock (5 mM) plus 10.56 mL of 20 mM EDTA/assay buffer.

5. Test compounds (compounds of the invention):

Prepare a working solution (5X) from 10 mM stock (DMSO) and make a series of 1:3 dilution. Compounds were assayed at 6 concentrations in duplicate.

Assay conditions and procedure:

Prothrombinase reaction was performed in final 50 μL of mixture containing PTase (20 uM PCPS, 5 nM hFVa, and 1 pM hFXa), 1.2 uM human factor II and varied concentration of the test compounds (5 μM to 0.021 μM or lower concentration range). Reaction was started by addition of PTase and incubated for 6 minutes at room temperature. Reaction was stopped by addition of EDTA/buffer to final 10 mM. Activity of thrombin (product) was then measured in the presence of 0.1 mM of Spectrozyme-TH as substrate at 405 nm for 5 minutes (10 second intervals), at ambient temperature, in a THEROmax microplate reader. Reactions were performed in 96-well microtiter plates.

In the first step of the assay, 10 μl of diluted test compound (5X) or buffer was added to the plates in duplicate.

Then 10 μl of prothombin (hFII) (5X) was added to each well. Next 30 μl PTase was added to each well, mix for about 30 seconds. The plates were then incubated at ambient temperature for 6 minutes.

In the next step, 50 μl of 20 mM EDTA (in assay buffer) was added to each well to stop the reaction. The resulting solutions were then mixed for about 10 seconds. Then 100 μl of 0.2 mM spectrozyme was added to each well. The thrombin reaction rate was then measured at 405 nm for 5 minutes (at 10 second intervals) in a Molecular Devices microplate reader.

Calculations:

Thrombin reaction rate was expressed as mOD/minute using OD readings from the five minute reaction. $IC_{50}$ values were calculated with the log-logit curve fit program.

The compounds of the invention demonstrated the ability to inhibit prothrombinase when tested in this assay.

EXAMPLE 14

(In vivo assay)

The following assay demonstrates the ability of the compounds to act as anti-coagulants.

Male rats (250–330 g) were anesthetized with sodium pentobarbital (90 mg/kg, i.p.) and prepared for surgery. The left carotid artery was cannulated for the measurement of blood pressure as well as for taking blood samples to monitor clotting variables (prothrombin time (PT) and activated partial thromboplastin time (aPTT)). The tail vein was cannulated for the purpose of administering the test compounds (i.e., the compounds of the invention and standards) and the thromboplastin infusion. The abdomen was opened via a mid-line incision and the abdominal vena cava was isolated for 2–3 cm distal to the renal vein. All venous branches in this 2–3 cm segment of the abdominal vena cava were ligated. Following all surgery, the animals were allowed to stabilize prior to beginning the experiment. Test compounds were administered as an intravenous bolus (t=0). Three minutes later (t=3), a 5-minute infusion of thromboplastin was begun. Two minutes into the infusion (t=5), the abdominal vena cava was ligated at both the proximal and distal ends. The vessel was left in place for 60 minutes, after which it was excised from the animal, slit open, the clot (if any) carefully removed, and weighed. Statistical analysis on the results was performed using a Wilcoxin-matched-pairs signed rank test.

The compounds of the invention, when tested in this assay, demonstrated the ability to inhibit the clotting of blood.

While the present invention has been described with reference to the specific embodiments thereof, it should be understood by those skilled in the art that various changes may be made and equivalents may be substituted without departing from the true spirit and scope of the invention. In addition, many modifications may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of formula (I):

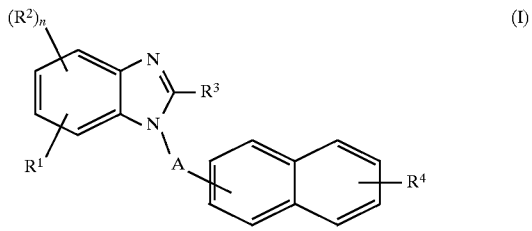

wherein:

n is 0 or 1;

A is alkylene;

$R^1$ is —$OR^5$ or —$N(R^5)R^6$;

$R^2$ is independently nitro, alkyl (optionally substituted by —$C(O)OR^8$), —$OR^5$, —$N(R^7)R^9$, —$C(O)OR^8$, —$C(O)N(R^8)R^9$ or piperidinyl optionally substituted by —$C(O)OR^8$ or —$R^{10}$—$C(O)OR^8$;

$R^3$ is hydrogen or alkyl optionally substituted by one or more substituents selected from the group consisting of halo, —$C(O)OR^8$, or —$C(O)N(R^8)R^9$;

$R^4$ is —$C(NH)NH_2$;

each $R^5$ is independently:
  hydrogen; or
  alkyl optionally substituted by one or more substituents selected from the group consisting of —$C(O)OR^8$, —$C(O)N(R^8)R^9$ and phenyl (optionally substituted by —$C(O)OR^8$); or
  piperidinyl or pyrrolidinyl, each optionally substituted by 1-iminoalkyl, —$C(NH)N(R^8)R^9$, —$R^{10}$—$C(O)OR^8$ or —$SO_3H$;

$R^6$ is hydrogen, alkyl, benzyl (optionally substituted by —$C(O)OR^8$), —$R^{10}$—$C(O)OR^8$, —$R^{10}$—$C(O)N(R^8)R^9$ or —$C(O)R^7$;

$R^7$ is a branched or straight chain alkylene substituted by one or more substituents selected from the group consisting of —$C(O)OR^8$ and aryl (optionally substituted by —$C(O)OR^8$);

each $R^8$ and $R^9$ is independently hydrogen or alkyl; and each $R^{10}$ is independently a branched or straight chain alkylene, or a pharmaceutically acceptable salt thereof.

2. The compound of claim 1 wherein:

n is 0 or 1;

$R^1$ is —$OR^5$ or —$N(R^5)R^6$;

$R^2$ is independently nitro, methyl (substituted by —$C(O)OR^8$), —$OR^5$, —$N(R^7)R^9$, —$C(O)OR^8$, —$C(O)N(R^8)R^9$ or piperidinyl optionally substituted by —$C(O)OR^8$ or —$R^{10}$—$C(O)OR^8$;

$R^3$ is hydrogen or alkyl optionally substituted by —$C(O)OR^8$ or —$C(O)N(R^8)R^9$;

$R^4$ is —$C(NH)NH_2$;

each $R^5$ is independently:
  hydrogen; or
  alkyl optionally substituted by —$C(O)OR^8$, —$C(O)N(R^8)R^9$ or phenyl (optionally substituted by —$C(O)OR^8$); or
  piperidinyl optionally substituted by 1-iminoalkyl, —$R^{10}$—$C(O)OR^8$ or —$SO_3H$;

$R^6$ is hydrogen, alkyl, benzyl (optionally substituted by —$C(O)OR^8$) or —$R^{10}$—$C(O)OR^8$:

$R^7$ is a branched or straight chain alkylene substituted by one or more substituents selected from the group consisting of —C(O)OR$^8$ and aryl (optionally substituted by —C(O)OR$^8$);

each R$^8$ and R$^9$ is independently hydrogen, methyl or ethyl; and each R$^{10}$ is independently a branched or straight chain alkylene.

3. The compound of claim 2 wherein:

n is 0;

A is methylene;

R$^1$ is —OR$^5$;

R$^3$ is hydrogen or alkyl optionally substituted by —C(O)OR$^8$ or —C(O)N(R$^8$)R$^9$;

R$^4$ is —C(NH)NH$_2$;

R$^5$ is piperidinyl optionally substituted by 1-iminoalkyl; and

R$^8$ and R$^9$ are independently hydrogen, methyl or ethyl.

4. The compound of claim 3 selected from the group consisting of:

1-(4-amidinonaphth-1-yl)methyl-2-methyl-6-(N-(1-iminoethyl)piperidin-4-yloxybenzimidazole;

1-(4-amidinonaphth-1-yl)methyl-2-methyl-5-(N-(1-iminoethyl)piperidin-4-yloxybenzimidazole;

1-(4-amidinonaphth-1-yl)methyl-2-methyl-6-(N-(1-iminoethyl)piperidin-3-yloxybenzimidazole;

1-(4-amidinonaphth-1-yl)methyl-2-ethyl-6-(N-(1-iminoethyl)piperidin-4-yloxybenzimidazole;

1-(4-amidinonaphth-1-yl)methyl-2-ethyl-5-(N-(1-iminoethyl)piperidin-4-yloxybenzimidazole;

1-(4-amidinonaphth-1-yl)methyl-2-isopropyl-6-(N-(1-iminoethyl)piperidin-4-yloxybenzimidazole;

1-(4-amidinonaphth-1-yl)methyl-2-isopropyl-5-(N-(1-iminoethyl)piperidin-4-yloxy)benzimidazole;

1-(4-amidinonaphth-1-yl)methyl-2-t-butyl-6-(N-(1-iminoethyl)piperidin-4-yloxy)benzimidazole;

1-(4-amidinonaphth-1-yl)methyl-2-t-butyl-5-(N-(1-iminoethyl)piperidin-4-yloxy)benzimidazole;

1-(4-amidinonaphth-1-yl)methyl-6-(N-(1-iminoethyl)piperidin-4-yloxy)benzimidazole;

1-(4-amidinonaphth-1-yl)methyl-5-(N-(1-iminoethyl)piperidin-4-yloxy)benzimidazole;

1-(4-amidinonaphth-1-yl)methyl-2-propyl-6-(N-(1-iminoethyl)piperidin-4-yloxy)benzimidazole;

1-(4-amidinonaphth-1-yl)methyl-2-propyl-5-(N-(1-iminoethyl)piperidin-4-yloxy)benzimidazole;

1-(4-amidinonaphth-1-yl)methyl-2-propyl-6-(piperidin-4-yloxy)benzimidazole;

1-(4-amidinonaphth-1-yl)methyl-2-propyl-5-(piperidin-4-yloxy)benzimidazole;

1-(4-amidinonaphth-1-yl)methyl-2-isopropyl-6-(piperidin-4-yloxy)benzimidazole;

1-(4-amidinonaphth-1-yl)methyl-2-isopropyl-5-(piperidin-4-yloxy)benzimidazole;

1-(4-amidinonaphth-1-yl)methyl-2-sec-butyl-6-(N-(1-iminoethyl)piperidin-4-yloxy)benzimidazole;

1-(4-amidinonaphth-1-yl)methyl-2-sec-butyl-5-(N-(1-iminoethyl)piperidin-4-yloxy)benzimidazole;

1-(4-amidinonaphth-1-yl)methyl-2-n-butyl-6-(N-(1-iminoethyl)piperidin-4-yloxy)benzimidazole;

1-(4-amidinonaphth-1-yl)methyl-2-n-butyl-5-(N-(1-iminoethyl)piperidin-4-yloxy)benzimidazole;

1-(4-amidinonaphth-1-yl)methyl-2-(2-carboxyethyl)-6-(N-(1-iminoethyl)piperidin-4-yloxy)benzimidazole;

1-(4-amidinonaphth-1-yl)methyl-2-(2-carboxyethyl)-5-(N-(1-iminoethyl)piperidin-4-yloxy)benzimidazole; and 1-(4-amidinonaphth-1-yl)methyl-2-(2-aminocarbonylethyl)-6-(N-(1-iminoethyl)piperidin-4-yloxy)benzimidazole.

5. The compound of claim 2 wherein:

n is 0;

A is methylene;

R$^1$ is —N(R$^5$)R$^6$;

R$^3$ is hydrogen or methyl;

R$^4$ is —C(NH)NH$_2$;

R$^5$ is piperidinyl optionally substituted by 1-iminoalkyl;

R$^6$ is hydrogen, —R$^{10}$—C(O)OR$^8$ or —C(O)N(R$^8$)R$^9$;

R$^8$ and R$^9$ are independently hydrogen or methyl; and

R$^{10}$ is a branched or straight chain alkylene.

6. The compound of claim 5 selected from the group consisting of:

1-(4-amidinonaphth-1-yl)methyl-6-(N-(1-iminoethyl)piperidin-4-yl)aminobenzimidazole;

1-(4-amidinonaphth-1-yl)methyl-2-methyl-6-(N-(N'-(1-iminoethyl)piperidin-4-yl)-N-((methoxycarbonyl)methyl)amino)benzimidazole;

1-(4-amidinonaphth-1-yl)methyl-2-methyl-6-(N-(N'-(1-iminoethyl)piperidin-4-yl)-N-((aminocarbonyl)methyl)amino)benzimidazole;

1-(4-amidinonaphth-1-yl)methyl-2-methyl-6-(N-(N'-(1-iminoethyl)piperidin-4-yl)-N-(3-carboxypropyl)amino)benzimidazole;

1-(4-amidinonaphth-1-yl)methyl-2-methyl-6-(N-(N'-(1-iminoethyl)piperidin-4-yl)-N-(2-(methoxycarbonyl)propyl)amino)benzimidazole;

1-(4-amidinonaphth-1-yl)methyl-2-methyl-6-(N-(N'-(1-iminoethyl)piperidin-4-yl)-N-(2-(carboxy)propyl)amino)benzimidazole; and 1-(4-amidinonaphth-1-yl)methyl-2-methyl-5-(N-(N'-(1-iminoethyl)piperidin-4-yl)-N-(2-(carboxy)propyl)amino)benzimidazole.

7. The compound of claim 2 wherein:

n is 1;

A is methylene;

R$^1$ is —OR$^5$;

R$^2$ is nitro, —OR$^5$, —N(R$^7$)R$^9$, —C(O)OR$^8$, or piperidinyl (optionally substituted by —C(O)OR$^8$);

R$^3$ is methyl or 1-isopropyl;

R$^4$ is —C(NH)NH$_2$;

each R$^5$ is independently hydrogen or alkyl optionally substituted by —C(O)OR$^8$, —C(O)N(R$^8$)R$^9$, phenyl (optionally substituted by —C(O)OR$^8$), or piperidinyl (optionally substituted by —R$^{10}$—C(O)OR$^8$ or 1-iminoethyl);

R$^7$ is a branched or straight chain alkylene substituted by —C(O)OR$^8$ or phenyl (optionally substituted by —C(O)OR$^8$); and each R$^8$ and R$^9$ is independently hydrogen or methyl.

8. The compound of claim 7 selected from the group consisting of:

1-(4-amidinonaphth-1-yl)methyl-2-methyl-5-hydroxy-6-(N-(1-iminoethyl)piperidin-4-yloxy)benzimidazole;

1-(4-amidinonaphth-1-yl)methyl-2-methyl-5-(aminocarbonyl)methoxy-6-(N-(1-iminoethyl)piperidin-4-yloxy)benzimidazole;

1-(4-amidinonaphth-1-yl)methyl-2-methyl-5-(carboxy)methoxy-6-(N-(1-iminoethyl)piperidin-4-yloxy)benzimidazole;

1-(4-amidinonaphth-1-yl)methyl-2-methyl-5-(4-(methoxycarbonyl)benzyloxy)-6-(N-(1-iminoethyl)piperidin-4-yloxy)benzimidazole;

1-(4-amidinonaphth-1-yl)methyl-2-methyl-5-(4-(carboxy)benzyloxy)-6-(N-(1-iminoethyl)piperidin-4-yloxy)benzimidazole;

1-(4-amidinonaphth-1-yl)methyl-2-methyl-5-carboxy-6-(N-(1-iminoethyl)piperidin-4-yloxy)benzimidazole;

1-(4-amidinonaphth-1-yl)methyl-2-methyl-5-(aminocarbonyl)methoxy)-6-(N-(1-iminoethyl)piperidin-4-yloxy)benzimidazole;

1-(4-amidinonaphth-1-yl)methyl-2-methyl-5-(3-(methoxycarbonyl)benzyloxy)-6-(N-(1-iminoethyl)piperidin-4-yloxy)benzimidazole;

1-(4-amidinonaphth-1-yl)methyl-2-methyl-5-(3-(carboxy)benzyloxy)-6-(N-(1-iminoethyl)piperidin-4-yloxy)benzimidazole;

1-(4-amidinonaphth-1-yl)methyl-2-methyl-5-(methoxycarbonyl)methoxy-6-(N-(1-iminoethyl)piperidin-4-yloxy)benzimidazole;

1-(4-amidinonaphth-1-yl)methyl-2-methyl-5-(1-(aminocarbonyl)ethoxy)-6-(N-(1-iminoethyl)piperidin-4-yloxy)benzimidazole;

1-(4-amidinonaphth-1-yl)methyl-2-methyl-5-(1-(methoxycarbonyl)ethoxy)-6-(N-(1-iminoethyl)piperidin-4-yloxy)benzimidazole;

1-(4-amidinonaphth-1-yl)methyl-2-methyl-5-(1-(carboxy)ethoxy)-6-(N-(1-iminoethyl)piperidin-4-yloxy)benzimidazole;

1-(4-amidinonaphth-1-yl)methyl-2-isopropyl-4-methoxy-6-(piperidin-4-yloxy)benzimidazole;

1-(4-amidinonaphth-1-yl)methyl-2-isopropyl-7-methoxy-5-(piperidin-4-yloxy)benzimidazole;

1-(4-amidinonaphth-1-yl)methyl-2-isopropyl-4-methoxy-6-(N-(1-iminoethyl)piperidin-4-yloxy)benzimidazole;

1-(4-amidinonaphth-1-yl)methyl-2-isopropyl-7-methoxy-5-(N-(1-iminoethyl)piperidin-4-yloxy)benzimidazole;

1-(4-amidinonaphth-1-yl)methyl-2-methyl-5-(N-(4-carboxy)benzylamino)-6-(N-(1-iminoethyl)piperidin-4-yloxy)benzimidazole;

1-(4-amidinonaphth-1-yl)methyl-2-isopropyl-4-(4-carboxypiperidin-1-yl)-6-(N-(1-iminoethyl)piperidin-4-yloxy)benzimidazole;

1-(4-amidinonaphth-1-yl)methyl-2-isopropyl-4-(carboxy)methoxy-6-(N-(1-iminoethyl)piperidin-4-yloxy)benzimidazole;

1-(4-amidinonaphth-1-yl)methyl-2-isopropyl-7-nitro-6-(N-(1-iminoethyl)piperidin-4-yloxy)benzimidazole;

1-(4-amidinonaphth-1-yl)methyl-2-methyl-7-nitro-6-(N-(1-iminoethyl)piperidin-4-yloxy)benzimidazole;

1-(4-amidinonaphth-1-yl)methyl-2-isopropyl-5-(N-(2-carboxyprop-2-yl)amino)-6-(N-(1-iminoethyl)piperidin-4-yloxy)benzimidazole;

1-(4-amidinonaphth-1-yl)methyl-2-isopropyl-5-(N-(4-carboxy)benzylamino)-6-(N-(1-iminoethyl)piperidin-4-yloxy)benzimidazole;

1-(4-amidinonaphth-1-yl)methyl-2-isopropyl-5-(N-(2-carboxyethyl)amino)-6-(N-(1-iminoethyl)piperidin-4-yloxy)benzimidazole; and 1-(4-amidinonaphth-1-yl)methyl-2-methyl-5-(N-(carboxymethyl)piperidin-4-yloxy)-6-(N-(1-iminoethyl)piperidin-4-yloxy)benzimidazole.

9. The compound of claim 2 wherein:

n is 1;

A is methylene;

$R^1$ is —N($R^5$)$R^6$;

$R^2$ is —C(O)O$R^8$ or —C(O)N($R^8$)$R^9$;

$R^3$ is 1-isopropyl;

$R^4$ is —C(NH)NH$_2$;

$R^5$ is piperidinyl optionally substituted by 1-iminoethyl;

$R^6$ is hydrogen; and each $R^8$ and $R^9$ is independently hydrogen or methyl.

10. The compound of claim 9 selected from the group consisting of:

1-(4-amidinonaphth-1-yl)methyl-2-isopropyl-4-carboxy-6-(N-(1-iminoethyl)piperidin-4-ylamino)benzimidazole; and 1-(4-amidinonaphth-1-yl)methyl-2-isopropyl-4-aminocarbonyl-6-(N-(1-iminoethyl)piperidin-4-ylamino)benzimidazole.

11. A pharmaceutical composition useful in treating a human having a disease-state characterized by thrombotic activity, which composition comprises a therapeutically effective amount of a compound of formula (I):

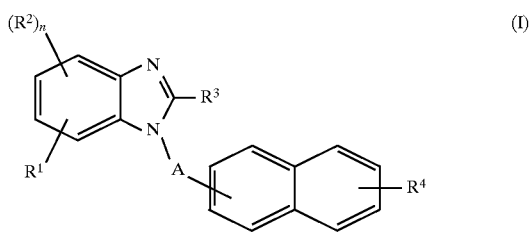

wherein:

n is 0 or 1;

A is alkylene;

$R^1$ is —O$R^5$ or —N($R^5$)$R^6$;

$R^2$ is independently nitro, alkyl (optionally substituted by —C(O)O$R^8$), —O$R^5$, —N($R^7$)$R^9$, —C(O)O$R^8$, —C(O)N($R^8$)$R^9$ or piperidinyl optionally substituted by —C(O)O$R^8$ or —$R^{10}$—C(O)O$R^8$;

$R^3$ is hydrogen or alkyl optionally substituted by one or more substituents selected from the group consisting of halo, —C(O)O$R^8$, or —C(O)N($R^8$)$R^9$;

$R^4$ is —C(NH)NH$_2$;

each $R^5$ is independently:

hydrogen; or alkyl optionally substituted by one or more substituents selected from the group consisting of —C(O)O$R^8$, —C(O)N($R^8$)$R^9$ and phenyl (optionally substituted by —C(O)O$R^8$); or piperidinyl or pyrrolidinyl, each optionally substituted by 1-iminoalkyl, —C(NH)N($R^8$)$R^9$, —$R^{10}$—C(O)O$R^8$ or —SO$_3$H;

$R^6$ is hydrogen, alkyl, benzyl (optionally substituted by —C(O)O$R^8$), —$R^{10}$—C(O)O$R^8$, —$R^{10}$—C(O)N($R^8$) $R^9$ or —C(O)$R^7$;

$R^7$ is a branched or straight chain alkylene substituted by one or more substituents selected from the group consisting of —C(O)O$R^8$ and aryl (optionally substituted by —C(O)O$R^8$);

each $R^8$ and $R^9$ is independently hydrogen or alkyl; and each $R^{10}$ is independently a branched or straight chain alkylene, or a pharmaceutically acceptable salt thereof, and a pharmaceutically acceptable excipient thereof.

12. A method of treating a human having a disease-state characterized by thrombotic activity, which method comprises administering to a human in need thereof a therapeutically effective amount of a compound of formula (I):

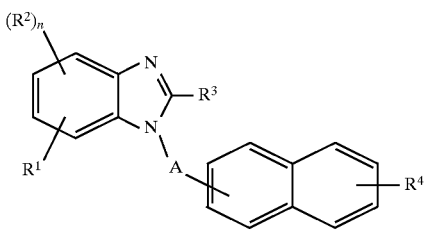

wherein:
n is 0 or 1;
A is alkylene;
$R^1$ is —$OR^5$ or —$N(R^5)R^6$;
$R^2$ is independently nitro, alkyl (optionally substituted by —$C(O)OR^8$), —$OR^5$, —$N(R^7)R^9$, —$C(O)OR^8$, —$C(O)N(R^8)R^9$ or piperidinyl optionally substituted by —$C(O)OR^8$ or —$R^{10}$—$C(O)OR^8$;
$R^3$ is hydrogen or alkyl optionally substituted by one or more substituents selected from the group consisting of halo, —$C(O)OR^8$, or —$C(O)N(R^8)R^9$;
$R^4$ is —$C(NH)NH_2$;
each $R^5$ is independently:
hydrogen; or
alkyl optionally substituted by one or more substituents selected from the group consisting of —$C(O)OR^8$, —$C(O)N(R^8)R^9$ and phenyl (optionally substituted by —$C(O)OR^8$); or
piperidinyl or pyrrolidinyl, each optionally substituted by 1-iminoalkyl, —$C(NH)N(R^8)R^9$, —$R^{10}$—$C(O)OR^8$ or —$SO_3H$;
$R^6$ is hydrogen, alkyl, benzyl (optionally substituted by —$C(O)OR^8$), —$R^{10}$—$C(O)OR^8$, —$R^{10}$—$C(O)N(R^8)R^9$ or —$C(O)R^7$;
$R^7$ is a branched or straight chain alkylene substituted by one or more substituents selected from the group consisting of —$C(O)OR^8$ and aryl (optionally substituted by —$C(O)OR^8$);
each $R^8$ and $R^9$ is independently hydrogen or alkyl; and
each $R^{10}$ is independently a branched or straight chain alkylene, or a pharmaceutically acceptable salt thereof.

13. A method of treating a human having a disease-state alleviated by the inhibition of factor Xa, which method comprises administering to a human in need thereof a therapeutically effective amount of a compound of formula (I):

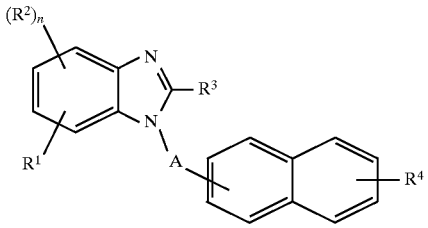

wherein:
n is 0 or 1;
A is alkylene;
$R^1$ is —$OR^5$ or —$N(R^5)R^6$;
$R^2$ is independently nitro, alkyl (optionally substituted by —$C(O)OR^8$), —$OR^5$, —$N(R^7)R^9$, —$C(O)OR^8$, —$C(O)N(R^8)R^9$ or piperidinyl optionally substituted by —$C(O)OR^8$ or —$R^{10}$—$C(O)OR^8$;
$R^3$ is hydrogen or alkyl optionally substituted by one or more substituents selected from the group consisting of halo, —$C(O)OR^8$, or —$C(O)N(R^8)R^9$;
$R^4$ is —$C(NH)NH_2$;
each $R^5$ is independently:
hydrogen; or
alkyl optionally substituted by one or more substituents selected from the group consisting of —$C(O)OR^8$, —$C(O)N(R^8)R^9$ and phenyl (optionally substituted by —$C(O)OR^8$); or
piperidinyl or pyrrolidinyl, each optionally substituted by 1-iminoalkyl, —$C(NH)N(R^8)R^9$, —$R^{10}$—$C(O)OR^8$ or —$SO_3H$;
$R^6$ is hydrogen, alkyl, benzyl (optionally substituted by —$C(O)OR^8$), —$R^{10}$—$C(O)OR^8$, —$R^{10}$—$C(O)N(R^8)R^9$ or —$C(O)R^7$;
$R^7$ is a branched or straight chain alkylene substituted by one or more substituents selected from the group consisting of —$C(O)OR^8$ and aryl (optionally substituted by —$C(O)OR^8$);
each $R^8$ and $R^9$ is independently hydrogen or alkyl; and
each $R^{10}$ is independently a branched or straight chain alkylene, or a pharmaceutically acceptable salt thereof.

14. A method of inhibiting human factor Xa in vitro by the administration of a compound of formula (I):

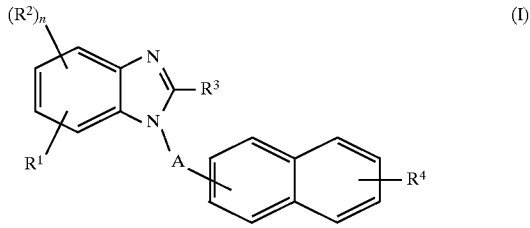

wherein:
n is 0 or 1;
A is alkylene;
$R^1$ is —$OR^5$ or —$N(R^5)R^6$;
$R^2$ is independently nitro, alkyl (optionally substituted by —$C(O)OR^8$), —$OR^5$, —$N(R^7)R^9$, —$C(O)OR^8$, —$C(O)N(R^8)R^9$ or piperidinyl optionally substituted by —$C(O)OR^8$ or —$R^{10}$—$C(O)OR^8$;
$R^3$ is hydrogen or alkyl optionally substituted by one or more substituents selected from the group consisting of halo, —$C(O)OR^8$, or —$C(O)N(R^8)R^9$;
$R^4$ is —$C(NH)NH_2$;
each $R^5$ is independently:
hydrogen; or
alkyl optionally substituted by one or more substituents selected from the group consisting of —$C(O)OR^8$, —$C(O)N(R^8)R^9$ and phenyl (optionally substituted by —$C(O)OR^8$); or
piperidinyl or pyrrolidinyl, each optionally substituted by 1-iminoalkyl, —$C(NH)N(R^8)R^9$, —$R^{10}$—$C(O)OR^8$ or —$SO_3H$;
$R^6$ is hydrogen, alkyl, benzyl (optionally substituted by —$C(O)OR^8$), —$R^{10}$—$C(O)OR^8$, —$R^{10}$—$C(O)N(R^8)R^9$ or —$C(O)R^7$;
$R^7$ is a branched or straight chain alkylene substituted by one or more substituents selected from the group consisting of —$C(O)OR^8$ and aryl (optionally substituted by —$C(O)OR^8$);
each $R^8$ and $R^9$ is independently hydrogen or alkyl; and
each $R^{10}$ is independently a branched or straight chain alkylene, or a pharmaceutically acceptable salt thereof.

* * * * *